US012478381B2

(12) United States Patent
Kuyler et al.

(10) Patent No.: US 12,478,381 B2
(45) Date of Patent: Nov. 25, 2025

(54) DEVICES AND TECHNIQUES FOR TREATING LESSER METATARSALS OF THE FOOT

(71) Applicant: Treace Medical Concepts, Inc., Ponte Vedra, FL (US)

(72) Inventors: Adriaan Kuyler, Ponte Vedra, FL (US); Sean F. Scanlan, Jacksonville, FL (US); Paul Dayton, Ankeny, IA (US); William T. DeCarbo, Pittsburgh, PA (US); Mark Erik Easley, Durham, NC (US); Daniel J. Hatch, Greeley, CO (US); Jody McAleer, Jefferson City, MO (US); Robert D. Santrock, Morgantown, WV (US); W. Bret Smith, Durango, CO (US)

(73) Assignee: Treace Medical Concepts, Inc, Ponte Vedra, FL (US)

( * ) Notice: Subject to any disclaimer, the term of this patent is extended or adjusted under 35 U.S.C. 154(b) by 352 days.

(21) Appl. No.: 18/174,596

(22) Filed: Feb. 24, 2023

(65) Prior Publication Data

US 2023/0263536 A1 Aug. 24, 2023

Related U.S. Application Data

(60) Provisional application No. 63/313,726, filed on Feb. 24, 2022, provisional application No. 63/406,486, filed on Sep. 14, 2022.

(51) Int. Cl.

| | |
|---|---|
| ***A61B 17/66*** | (2006.01) |
| ***A61B 17/15*** | (2006.01) |
| *A61B 17/17* | (2006.01) |

(52) U.S. Cl.

CPC .............. *A61B 17/15* (2013.01); *A61B 17/66* (2013.01); *A61B 17/1775* (2016.11)

(58) Field of Classification Search

CPC ..... A61B 17/15; A61B 17/88; A61B 17/8866; A61B 17/17; A61B 17/1775; A61B 17/66

See application file for complete search history.

(56) References Cited

U.S. PATENT DOCUMENTS

| | | | |
|---|---|---|---|
| 2,251,209 | A | 7/1941 | Stader |
| 2,432,695 | A | 12/1947 | Speas |

(Continued)

FOREIGN PATENT DOCUMENTS

| | | | |
|---|---|---|---|
| AU | 2009227957 B2 | 7/2014 | |
| CA | 2491824 A1 | 9/2005 | |

(Continued)

OTHER PUBLICATIONS

Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.

(Continued)

*Primary Examiner* — Christopher J Beccia

(74) *Attorney, Agent, or Firm* — Fredrikson & Byron, P.A.

(57) ABSTRACT

A variety of surgical procedures may be performed on the bones of the foot, such as on one or more lesser metatarsals of the foot positioned laterally of the first metatarsal. For example, a surgical procedure may involve cutting an end of one or both of a second metatarsal and an intermediate cuneiform and/or cutting an end of one or both of a third metatarsal and a lateral cuneiform. The tarsometatarsal joints defined be one or both sets of bones may be cut to treat an arthritic joint, metatarsus adductus, and/or other clinical condition. In any case, various surgical instruments can be utilized during a procedure to help increase the accuracy and repeatability of the procedure patient-to-patient, improving overall patient outcomes. For example, one or more cut (Continued)

guides, compressor-distractor devices, and/or other instruments designed to accommodate the specific anatomical conditions of the procedure being performed may be utilized during procedure.

14 Claims, 34 Drawing Sheets

(56) References Cited

U.S. PATENT DOCUMENTS

| | | | |
|---|---|---|---|
| 3,664,022 | A | 5/1972 | Small |
| 4,069,824 | A | 1/1978 | Weinstock |
| 4,159,716 | A | 7/1979 | Borchers |
| 4,187,840 | A | 2/1980 | Watanabe |
| 4,187,841 | A | 2/1980 | Knutson |
| 4,335,715 | A | 6/1982 | Kirkley |
| 4,338,927 | A | 7/1982 | Volkov et al. |
| 4,349,018 | A | 9/1982 | Chambers |
| 4,409,973 | A | 10/1983 | Neufeld |
| 4,440,168 | A | 4/1984 | Warren |
| 4,501,268 | A | 2/1985 | Comparetto |
| 4,502,474 | A | 3/1985 | Comparetto |
| 4,509,511 | A | 4/1985 | Neufeld |
| 4,565,191 | A | 1/1986 | Slocum |
| 4,570,624 | A | 2/1986 | Wu |
| 4,627,425 | A | 12/1986 | Reese |
| 4,628,919 | A | 12/1986 | Clyburn |
| 4,632,102 | A | 12/1986 | Comparetto |
| 4,664,102 | A | 5/1987 | Comparetto |
| 4,708,133 | A | 11/1987 | Comparetto |
| 4,730,608 | A | 3/1988 | Schlein |
| 4,736,737 | A | 4/1988 | Fargie et al. |
| 4,750,481 | A | 6/1988 | Reese |
| 4,754,746 | A | 7/1988 | Cox |
| 4,757,810 | A | 7/1988 | Reese |
| 4,895,141 | A | 1/1990 | Koeneman et al. |
| 4,952,214 | A | 8/1990 | Comparetto |
| 4,959,066 | A | 9/1990 | Dunn et al. |
| 4,978,347 | A | 12/1990 | Ilizarov |
| 4,988,349 | A | 1/1991 | Pennig |
| 4,995,875 | A | 2/1991 | Coes |
| 5,021,056 | A | 6/1991 | Hofmann et al. |
| 5,035,698 | A | 7/1991 | Comparetto |
| 5,042,983 | A | 8/1991 | Rayhack |
| 5,049,149 | A | 9/1991 | Schmidt |
| 5,053,039 | A | 10/1991 | Hofmann et al. |
| 5,078,719 | A | 1/1992 | Schreiber |
| 5,112,334 | A | 5/1992 | Alchermes et al. |
| 5,147,364 | A | 9/1992 | Comparetto |
| 5,176,685 | A | 1/1993 | Rayhack |
| 5,207,676 | A | 5/1993 | Canadell et al. |
| 5,246,444 | A | 9/1993 | Schreiber |
| 5,254,119 | A | 10/1993 | Schreiber |
| 5,304,177 | A | 4/1994 | Pennig |
| 5,312,412 | A | 5/1994 | Whipple |
| 5,358,504 | A | 10/1994 | Paley et al. |
| 5,364,402 | A | 11/1994 | Mumme et al. |
| 5,374,271 | A | 12/1994 | Hwang |
| 5,413,579 | A | 5/1995 | Tom Du Toit |
| 5,415,663 | A | 5/1995 | Luckman et al. |
| 5,417,694 | A | 5/1995 | Marik et al. |
| 5,449,360 | A | 9/1995 | Schreiber |
| 5,470,335 | A | 11/1995 | Du Toit |
| 5,490,854 | A | 2/1996 | Fisher et al. |
| 5,529,075 | A | 6/1996 | Clark |
| 5,540,695 | A | 7/1996 | Levy |
| 5,578,038 | A | 11/1996 | Slocum |
| 5,586,564 | A | 12/1996 | Barrett et al. |
| 5,601,565 | A | 2/1997 | Huebner |
| 5,611,802 | A | 3/1997 | Samuelson et al. |
| 5,613,969 | A | 3/1997 | Jenkins, Jr. |
| 5,620,442 | A | 4/1997 | Bailey et al. |
| 5,620,448 | A | 4/1997 | Puddu |
| D380,548 | S | 7/1997 | Koros et al. |
| 5,643,270 | A | 7/1997 | Combs |
| 5,667,510 | A | 9/1997 | Combs |
| 5,722,978 | A | 3/1998 | Jenkins, Jr. |
| 5,749,875 | A | 5/1998 | Puddu |
| 5,779,709 | A | 7/1998 | Harris, Jr. et al. |
| 5,788,695 | A | 8/1998 | Richardson |
| 5,792,159 | A | 8/1998 | Amin |
| 5,803,924 | A | 9/1998 | Oni et al. |
| 5,810,822 | A | 9/1998 | Mortier |
| D403,066 | S | 12/1998 | Defonzo |
| 5,843,085 | A | 12/1998 | Graser |
| 5,893,553 | A | 4/1999 | Pinkous |
| 5,911,724 | A | 6/1999 | Wehrli |
| 5,935,128 | A | 8/1999 | Carter et al. |
| 5,941,877 | A | 8/1999 | Viegas et al. |
| 5,951,556 | A | 9/1999 | Faccioli et al. |
| D417,276 | S | 11/1999 | Defonzo |
| 5,980,526 | A | 11/1999 | Johnson et al. |
| 5,984,931 | A | 11/1999 | Greenfield |
| 6,007,535 | A | 12/1999 | Rayhack et al. |
| 6,027,504 | A | 2/2000 | Mcguire |
| 6,030,391 | A | 2/2000 | Brainard et al. |
| 6,162,223 | A | 12/2000 | Orsak et al. |
| 6,171,309 | B1 | 1/2001 | Huebner |
| 6,203,545 | B1 | 3/2001 | Stoffella |
| 6,248,109 | B1 | 6/2001 | Stoffella |
| 6,391,031 | B1 | 5/2002 | Toomey |
| 6,416,465 | B2 | 7/2002 | Brau |
| 6,478,799 | B1 | 11/2002 | Williamson |
| 6,511,481 | B2 | 1/2003 | Von Hoffmann et al. |
| 6,547,793 | B1 | 4/2003 | Mcguire |
| 6,676,662 | B1 | 1/2004 | Bagga et al. |
| 6,719,773 | B1 | 4/2004 | Boucher et al. |
| 6,743,233 | B1 | 6/2004 | Baldwin et al. |
| 6,755,838 | B2 | 6/2004 | Trnka |
| 6,796,986 | B2 | 9/2004 | Duffner |
| 6,859,661 | B2 | 2/2005 | Tuke |
| 6,964,645 | B1 | 11/2005 | Smits |
| 7,018,383 | B2 | 3/2006 | Mcguire |
| 7,033,361 | B2 | 4/2006 | Collazo |
| 7,097,647 | B2 | 8/2006 | Segler |
| 7,112,204 | B2 | 9/2006 | Justin et al. |
| 7,153,310 | B2 | 12/2006 | Ralph et al. |
| 7,182,766 | B1 | 2/2007 | Mogul |
| 7,241,298 | B2 | 7/2007 | Nemec et al. |
| 7,282,054 | B2 | 10/2007 | Steffensmeier et al. |
| D566,271 | S | 4/2008 | Gao et al. |
| 7,377,924 | B2 | 5/2008 | Raistrick et al. |
| 7,465,303 | B2 | 12/2008 | Riccione et al. |
| 7,540,874 | B2 | 6/2009 | Trumble et al. |
| D597,666 | S | 8/2009 | George et al. |
| 7,572,258 | B2 | 8/2009 | Stiernborg |
| 7,578,822 | B2 | 8/2009 | Rezach et al. |
| 7,618,424 | B2 | 11/2009 | Wilcox et al. |
| 7,641,660 | B2 | 1/2010 | Lakin et al. |
| D610,257 | S | 2/2010 | Horton |
| 7,686,811 | B2 | 3/2010 | Byrd et al. |
| 7,691,108 | B2 | 4/2010 | Lavallee |
| 7,763,026 | B2 | 7/2010 | Egger et al. |
| D629,900 | S | 12/2010 | Fisher |
| 7,967,823 | B2 | 6/2011 | Ammann et al. |
| 7,972,338 | B2 | 7/2011 | O'Brien |
| D646,389 | S | 10/2011 | Claypool et al. |
| 8,057,478 | B2 | 11/2011 | Kuczynski et al. |
| 8,062,301 | B2 | 11/2011 | Ammann et al. |
| D651,315 | S | 12/2011 | Bertoni et al. |
| D651,316 | S | 12/2011 | May et al. |
| 8,080,010 | B2 | 12/2011 | Schulz et al. |
| 8,080,045 | B2 | 12/2011 | Wotton, III |
| 8,083,746 | B2 | 12/2011 | Novak |
| 8,123,753 | B2 | 2/2012 | Poncet |
| 8,137,406 | B2 | 3/2012 | Novak et al. |
| 8,147,530 | B2 | 4/2012 | Strnad et al. |
| 8,167,918 | B2 | 5/2012 | Strnad et al. |
| 8,172,848 | B2 | 5/2012 | Tomko et al. |
| 8,192,441 | B2 | 6/2012 | Collazo |
| 8,197,487 | B2 | 6/2012 | Poncet et al. |
| 8,231,623 | B1 | 7/2012 | Jordan |
| 8,231,663 | B2 | 7/2012 | Kay et al. |

(56) References Cited

U.S. PATENT DOCUMENTS

| | | | |
|---|---|---|---|
| 8,236,000 | B2 | 8/2012 | Ammann et al. |
| 8,246,561 | B1 | 8/2012 | Agee et al. |
| D666,721 | S | 9/2012 | Wright et al. |
| 8,262,664 | B2 | 9/2012 | Justin et al. |
| 8,277,459 | B2 | 10/2012 | Sand et al. |
| 8,282,644 | B2 | 10/2012 | Edwards |
| 8,282,645 | B2 | 10/2012 | Lawrence et al. |
| 8,292,966 | B2 | 10/2012 | Morton |
| 8,303,596 | B2 | 11/2012 | Plaky et al. |
| 8,313,492 | B2 | 11/2012 | Wong et al. |
| 8,323,289 | B2 | 12/2012 | Re |
| 8,337,503 | B2 | 12/2012 | Lian |
| 8,343,159 | B2 | 1/2013 | Bennett |
| 8,377,105 | B2 | 2/2013 | Bscher |
| D679,395 | S | 4/2013 | Wright et al. |
| 8,409,209 | B2 | 4/2013 | Ammann et al. |
| 8,435,246 | B2 | 5/2013 | Fisher et al. |
| 8,475,462 | B2 | 7/2013 | Thomas et al. |
| 8,496,662 | B2 | 7/2013 | Novak et al. |
| 8,518,045 | B2 | 8/2013 | Szanto |
| 8,523,870 | B2 | 9/2013 | Green, II et al. |
| 8,529,571 | B2 | 9/2013 | Horan et al. |
| 8,540,777 | B2 | 9/2013 | Ammann et al. |
| 8,545,508 | B2 | 10/2013 | Collazo |
| D694,884 | S | 12/2013 | Mooradian et al. |
| D695,402 | S | 12/2013 | Dacosta et al. |
| 8,652,142 | B2 | 2/2014 | Geissler |
| 8,657,820 | B2 | 2/2014 | Kubiak et al. |
| D701,303 | S | 3/2014 | Cook |
| 8,672,945 | B2 | 3/2014 | Lavallee et al. |
| 8,696,716 | B2 | 4/2014 | Kartalian et al. |
| 8,702,715 | B2 | 4/2014 | Ammann et al. |
| D705,929 | S | 5/2014 | Frey |
| 8,715,363 | B2 | 5/2014 | Ratron et al. |
| 8,728,084 | B2 | 5/2014 | Berelsman et al. |
| 8,758,354 | B2 | 6/2014 | Habegger et al. |
| 8,764,760 | B2 | 7/2014 | Metzger et al. |
| 8,764,763 | B2 | 7/2014 | Wong et al. |
| 8,771,279 | B2 | 7/2014 | Philippon et al. |
| 8,777,948 | B2 | 7/2014 | Bernsteiner |
| 8,784,427 | B2 | 7/2014 | Fallin et al. |
| 8,784,457 | B2 | 7/2014 | Graham |
| 8,795,286 | B2 | 8/2014 | Sand et al. |
| 8,801,727 | B2 | 8/2014 | Chan et al. |
| 8,808,303 | B2 | 8/2014 | Stemniski et al. |
| 8,828,012 | B2 | 9/2014 | May et al. |
| 8,858,602 | B2 | 10/2014 | Weiner et al. |
| 8,882,778 | B2 | 11/2014 | Ranft |
| 8,882,816 | B2 | 11/2014 | Kartalian et al. |
| 8,888,785 | B2 | 11/2014 | Ammann et al. |
| D720,456 | S | 12/2014 | Dacosta et al. |
| 8,900,247 | B2 | 12/2014 | Tseng et al. |
| 8,906,026 | B2 | 12/2014 | Ammann et al. |
| 8,945,132 | B2 | 2/2015 | Play et al. |
| 8,998,903 | B2 | 4/2015 | Price et al. |
| 8,998,904 | B2 | 4/2015 | Zeetser et al. |
| 9,023,052 | B2 | 5/2015 | Lietz et al. |
| 9,044,250 | B2 | 6/2015 | Olsen et al. |
| 9,060,822 | B2 | 6/2015 | Wright et al. |
| 9,078,710 | B2 | 7/2015 | Thoren et al. |
| 9,089,376 | B2 | 7/2015 | Medoff et al. |
| 9,101,421 | B2 | 8/2015 | Blacklidge |
| 9,107,715 | B2 | 8/2015 | Blitz et al. |
| 9,113,920 | B2 | 8/2015 | Ammann et al. |
| D740,424 | S | 10/2015 | Dacosta et al. |
| D765,844 | S | 9/2016 | Dacosta |
| D766,434 | S | 9/2016 | Dacosta |
| D766,437 | S | 9/2016 | Dacosta |
| D766,438 | S | 9/2016 | Dacosta |
| D766,439 | S | 9/2016 | Dacosta |
| 9,452,057 | B2 | 9/2016 | Dacosta et al. |
| 9,522,023 | B2 | 12/2016 | Haddad et al. |
| 9,592,084 | B2 | 3/2017 | Grant |
| 9,622,805 | B2 | 4/2017 | Santrock et al. |
| 9,750,538 | B2 | 9/2017 | Soffiatti et al. |
| 9,770,272 | B2 | 9/2017 | Thoren et al. |
| 9,785,747 | B2 | 10/2017 | Geebelen |
| 9,924,969 | B2 | 3/2018 | Triplett et al. |
| 9,936,994 | B2 | 4/2018 | Smith et al. |
| 9,980,760 | B2 | 5/2018 | Dacosta et al. |
| 10,028,750 | B2 | 7/2018 | Rose |
| 10,064,631 | B2 | 9/2018 | Dacosta et al. |
| 10,159,499 | B2 | 12/2018 | Dacosta et al. |
| 10,292,713 | B2 | 5/2019 | Fallin et al. |
| 10,327,829 | B2 | 6/2019 | Dacosta et al. |
| 10,376,268 | B2 | 8/2019 | Fallin et al. |
| D865,173 | S | 10/2019 | Hartson et al. |
| 10,470,779 | B2 | 11/2019 | Fallin et al. |
| 10,524,808 | B1 | 1/2020 | Hissong et al. |
| 10,779,867 | B2 | 9/2020 | Penzimer et al. |
| D904,609 | S | 12/2020 | Dacosta et al. |
| 10,939,939 | B1 | 3/2021 | Gil et al. |
| D915,588 | S | 4/2021 | Dacosta et al. |
| D931,449 | S | 9/2021 | Tanabe |
| D943,741 | S | 2/2022 | Hartson et al. |
| D945,610 | S | 3/2022 | Wilson et al. |
| 11,304,705 | B2 | 4/2022 | Fallin et al. |
| D956,227 | S | 6/2022 | Dacosta et al. |
| 11,839,383 | B2 * | 12/2023 | Boffeli .................. A61B 17/66 |
| 11,974,788 | B2 * | 5/2024 | Chan .................. A61B 17/685 |
| 2002/0099381 | A1 | 7/2002 | Maroney |
| 2002/0107519 | A1 | 8/2002 | Dixon et al. |
| 2002/0165552 | A1 | 11/2002 | Duffner |
| 2002/0198531 | A1 | 12/2002 | Millard et al. |
| 2004/0010259 | A1 | 1/2004 | Keller et al. |
| 2004/0039394 | A1 | 2/2004 | Conti et al. |
| 2004/0097946 | A1 | 5/2004 | Dietzel et al. |
| 2004/0138669 | A1 | 7/2004 | Horn |
| 2005/0004676 | A1 | 1/2005 | Schon et al. |
| 2005/0021040 | A1 | 1/2005 | Bertagnoli |
| 2005/0059978 | A1 | 3/2005 | Sherry et al. |
| 2005/0070909 | A1 | 3/2005 | Egger et al. |
| 2005/0075641 | A1 | 4/2005 | Singhatat et al. |
| 2005/0101961 | A1 | 5/2005 | Huebner et al. |
| 2005/0149042 | A1 | 7/2005 | Metzger |
| 2005/0203509 | A1 | 9/2005 | Chinnaian et al. |
| 2005/0228389 | A1 | 10/2005 | Stiernborg |
| 2005/0251147 | A1 | 11/2005 | Novak |
| 2005/0267482 | A1 | 12/2005 | Hyde |
| 2005/0273112 | A1 | 12/2005 | Mcnamara |
| 2006/0122597 | A1 | 6/2006 | Jones et al. |
| 2006/0129163 | A1 | 6/2006 | Mcguire |
| 2006/0206044 | A1 | 9/2006 | Simon |
| 2006/0217733 | A1 | 9/2006 | Plassky et al. |
| 2006/0229604 | A1 | 10/2006 | Olsen et al. |
| 2006/0229621 | A1 | 10/2006 | Cadmus |
| 2006/0235383 | A1 | 10/2006 | Hollawell |
| 2006/0241607 | A1 | 10/2006 | Myerson et al. |
| 2006/0241608 | A1 | 10/2006 | Myerson et al. |
| 2006/0247649 | A1 | 11/2006 | Rezach et al. |
| 2006/0264961 | A1 | 11/2006 | Murray-Brown |
| 2007/0010818 | A1 | 1/2007 | Stone et al. |
| 2007/0055233 | A1 | 3/2007 | Brinker |
| 2007/0123857 | A1 | 5/2007 | Deffenbaugh et al. |
| 2007/0233138 | A1 | 10/2007 | Figueroa et al. |
| 2007/0265634 | A1 | 11/2007 | Weinstein |
| 2007/0276383 | A1 | 11/2007 | Rayhack |
| 2008/0009863 | A1 | 1/2008 | Bond et al. |
| 2008/0015603 | A1 | 1/2008 | Collazo |
| 2008/0039850 | A1 | 2/2008 | Rowley et al. |
| 2008/0091197 | A1 | 4/2008 | Coughlin |
| 2008/0140081 | A1 | 6/2008 | Heavener et al. |
| 2008/0147073 | A1 | 6/2008 | Ammann et al. |
| 2008/0172054 | A1 | 7/2008 | Claypool et al. |
| 2008/0195215 | A1 | 8/2008 | Morton |
| 2008/0208252 | A1 | 8/2008 | Holmes |
| 2008/0262500 | A1 | 10/2008 | Collazo |
| 2008/0269908 | A1 | 10/2008 | Warburton |
| 2008/0288004 | A1 | 11/2008 | Schendel |
| 2009/0036893 | A1 | 2/2009 | Kartalian et al. |
| 2009/0036931 | A1 | 2/2009 | Pech et al. |
| 2009/0054899 | A1 | 2/2009 | Ammann et al. |
| 2009/0093849 | A1 | 4/2009 | Grabowski |
| 2009/0105767 | A1 | 4/2009 | Reiley |

(56) References Cited

U.S. PATENT DOCUMENTS

2009/0118733 A1 5/2009 Orsak et al.
2009/0187189 A1 7/2009 Mirza et al.
2009/0198244 A1 8/2009 Leibel
2009/0198279 A1 8/2009 Zhang et al.
2009/0216089 A1 8/2009 Davidson
2009/0222047 A1 9/2009 Graham
2009/0254092 A1 10/2009 Albiol Llorach
2009/0254126 A1 10/2009 Orbay et al.
2009/0287309 A1 11/2009 Walch et al.
2010/0030283 A1 2/2010 King et al.
2010/0069910 A1 3/2010 Hasselman
2010/0121334 A1 5/2010 Couture et al.
2010/0130981 A1 5/2010 Richards
2010/0152782 A1 6/2010 Stone et al.
2010/0168799 A1 7/2010 Schumer
2010/0185245 A1 7/2010 Paul et al.
2010/0249779 A1 9/2010 Hotchkiss et al.
2010/0256687 A1 10/2010 Neufeld et al.
2010/0318088 A1 12/2010 Warne et al.
2010/0324556 A1 12/2010 Tyber et al.
2011/0009865 A1 1/2011 Orfaly
2011/0093084 A1 4/2011 Morton
2011/0118739 A1 5/2011 Tyber et al.
2011/0172662 A1 7/2011 Keilen
2011/0178524 A1 7/2011 Lawrence et al.
2011/0245835 A1 10/2011 Dodds et al.
2011/0288550 A1 11/2011 Orbay et al.
2011/0301648 A1 12/2011 Lofthouse et al.
2012/0016426 A1 1/2012 Robinson
2012/0065689 A1 3/2012 Prasad et al.
2012/0078258 A1 3/2012 Lo et al.
2012/0123420 A1 5/2012 Honiball
2012/0123484 A1 5/2012 Lietz et al.
2012/0130376 A1 5/2012 Loring et al.
2012/0130382 A1 5/2012 Iannotti et al.
2012/0130383 A1 5/2012 Budoff
2012/0184961 A1 7/2012 Johannaber
2012/0185056 A1 7/2012 Warburton
2012/0191199 A1 7/2012 Raemisch
2012/0239045 A1 9/2012 Li
2012/0253350 A1 10/2012 Anthony et al.
2012/0265301 A1 10/2012 Demers et al.
2012/0277745 A1 11/2012 Lizee
2012/0303033 A1 11/2012 Weiner et al.
2012/0330135 A1 12/2012 Millahn et al.
2013/0012949 A1 1/2013 Fallin et al.
2013/0035694 A1 2/2013 Grimm et al.
2013/0085499 A1 4/2013 Lian
2013/0085502 A1 4/2013 Harrold
2013/0096563 A1 4/2013 Meade et al.
2013/0131821 A1 5/2013 Cachia
2013/0150900 A1 6/2013 Haddad et al.
2013/0150903 A1 6/2013 Vincent
2013/0158556 A1 6/2013 Jones et al.
2013/0165936 A1 6/2013 Myers
2013/0165938 A1 6/2013 Chow et al.
2013/0172942 A1 7/2013 Wright et al.
2013/0184714 A1 7/2013 Kaneyama et al.
2013/0190765 A1 7/2013 Harris et al.
2013/0190766 A1 7/2013 Harris et al.
2013/0204259 A1 8/2013 Zajac
2013/0226248 A1 8/2013 Hatch et al.
2013/0226252 A1 8/2013 Mayer
2013/0231668 A1 9/2013 Olsen et al.
2013/0237987 A1 9/2013 Graham
2013/0237989 A1 9/2013 Bonutti
2013/0267956 A1 10/2013 Terrill et al.
2013/0310836 A1 11/2013 Raub et al.
2013/0325019 A1 12/2013 Thomas et al.
2013/0325076 A1 12/2013 Palmer et al.
2013/0331845 A1 12/2013 Horan et al.
2013/0338785 A1 12/2013 Wong
2014/0005672 A1 1/2014 Edwards et al.
2014/0025127 A1 1/2014 Richter
2014/0039501 A1 2/2014 Schickendantz et al.
2014/0039561 A1 2/2014 Weiner et al.
2014/0046387 A1 2/2014 Waizenegger
2014/0074099 A1 3/2014 Vigneron et al.
2014/0074101 A1 3/2014 Collazo
2014/0094861 A1 4/2014 Fallin
2014/0094924 A1 4/2014 Hacking et al.
2014/0135775 A1 5/2014 Maxson et al.
2014/0163563 A1 6/2014 Reynolds et al.
2014/0171953 A1 6/2014 Gonzalvez et al.
2014/0180342 A1 6/2014 Lowery et al.
2014/0188139 A1 7/2014 Fallin et al.
2014/0194884 A1 7/2014 Martin et al.
2014/0194999 A1 7/2014 Orbay et al.
2014/0207144 A1 7/2014 Lee et al.
2014/0228899 A1 8/2014 Thoren et al.
2014/0243825 A1 8/2014 Yapp et al.
2014/0249537 A1 9/2014 Wong et al.
2014/0257308 A1 9/2014 Johannaber
2014/0257509 A1 9/2014 Dacosta et al.
2014/0276815 A1 9/2014 Riccione
2014/0276853 A1 9/2014 Long et al.
2014/0277176 A1 9/2014 Buchanan et al.
2014/0277214 A1 9/2014 Helenbolt et al.
2014/0288562 A1 9/2014 Von Zabern et al.
2014/0296995 A1 10/2014 Reiley et al.
2014/0303621 A1 10/2014 Gerold et al.
2014/0336658 A1 11/2014 Luna et al.
2014/0343555 A1 11/2014 Russi et al.
2014/0350561 A1 11/2014 Dacosta et al.
2015/0032168 A1 1/2015 Orsak et al.
2015/0045801 A1 2/2015 Axelson, Jr. et al.
2015/0045839 A1 2/2015 Dacosta et al.
2015/0051650 A1 2/2015 Verstreken et al.
2015/0057667 A1 2/2015 Ammann et al.
2015/0066088 A1 3/2015 Brinkman et al.
2015/0066094 A1 3/2015 Anderson et al.
2015/0112446 A1 4/2015 Melamed et al.
2015/0119944 A1 4/2015 Geldwert
2015/0142064 A1 5/2015 Perez et al.
2015/0150608 A1 6/2015 Sammarco
2015/0182273 A1 7/2015 Stemniski et al.
2015/0223851 A1 8/2015 Hill et al.
2015/0230843 A1 8/2015 Palmer et al.
2015/0245858 A1 9/2015 Weiner et al.
2016/0015426 A1 1/2016 Dayton
2016/0022315 A1 1/2016 Soffiatti et al.
2016/0135858 A1 5/2016 Dacosta et al.
2016/0151165 A1 6/2016 Fallin et al.
2016/0175089 A1 6/2016 Fallin et al.
2016/0192950 A1 7/2016 Dayton et al.
2016/0192970 A1 7/2016 Dayton et al.
2016/0199076 A1 7/2016 Fallin et al.
2016/0213384 A1 7/2016 Fallin et al.
2016/0235414 A1 8/2016 Hatch et al.
2016/0242791 A1 8/2016 Fallin et al.
2016/0256204 A1 9/2016 Patel et al.
2016/0270800 A1 9/2016 Sanders
2016/0324532 A1 11/2016 Montoya et al.
2016/0354127 A1 12/2016 Lundquist et al.
2017/0014143 A1 1/2017 Dayton et al.
2017/0014173 A1 1/2017 Smith et al.
2017/0042598 A1 2/2017 Santrock et al.
2017/0042599 A1 2/2017 Bays et al.
2017/0079669 A1 3/2017 Bays et al.
2017/0143511 A1 5/2017 Cachia
2017/0164989 A1 6/2017 Weiner et al.
2017/0290614 A1 10/2017 Weiner et al.
2018/0021145 A1 1/2018 Seavey et al.
2018/0132868 A1 5/2018 Dacosta et al.
2018/0235765 A1 8/2018 Welker et al.
2018/0344334 A1 12/2018 Kim et al.
2019/0099189 A1 4/2019 Fallin et al.
2019/0336140 A1 11/2019 Dacosta et al.
2019/0350598 A1 11/2019 Jacobson
2020/0015856 A1 1/2020 Treace et al.
2020/0060721 A1 2/2020 Cermak
2020/0253641 A1 8/2020 Treace et al.
2021/0077131 A1* 3/2021 Denham ................ A61B 17/15
2021/0236180 A1 8/2021 Decarbo et al.

(56) References Cited

U.S. PATENT DOCUMENTS

| | | | |
|---|---|---|---|
| 2021/0244443 | A1 | 8/2021 | Coyne et al. |
| 2021/0361330 | A1 | 11/2021 | Mcaleer et al. |
| 2022/0117611 | A1 | 4/2022 | Milella, Jr. et al. |
| 2022/0211387 | A1 | 7/2022 | Perler et al. |
| 2022/0257267 | A1 | 8/2022 | Decarbo et al. |
| 2022/0323085 | A1 | 10/2022 | Hales et al. |
| 2022/0370082 | A1 | 11/2022 | Kuyler et al. |
| 2023/0043129 | A1 | 2/2023 | Mcaleer et al. |
| 2023/0263536 | A1 | 8/2023 | Kuyler et al. |

FOREIGN PATENT DOCUMENTS

| | | | |
|---|---|---|---|
| CA | 2854997 | A1 | 5/2013 |
| CH | 695846 | A5 | 9/2006 |
| CN | 2930668 | Y | 8/2007 |
| CN | 201558162 | U | 8/2010 |
| CN | 201572172 | U | 9/2010 |
| CN | 201586060 | U | 9/2010 |
| CN | 201912210 | U | 8/2011 |
| CN | 101237835 | B | 11/2012 |
| CN | 202801773 | U | 3/2013 |
| CN | 103462675 | A | 12/2013 |
| CN | 103505276 | A | 1/2014 |
| CN | 203458450 | U | 3/2014 |
| CN | 102860860 | B | 5/2014 |
| CN | 203576647 | U | 5/2014 |
| CN | 104490460 | A | 4/2015 |
| CN | 104510523 | A | 4/2015 |
| CN | 104523327 | A | 4/2015 |
| CN | 104546102 | A | 4/2015 |
| CN | 204379413 | U | 6/2015 |
| CN | 204410951 | U | 6/2015 |
| CN | 204428143 | U | 7/2015 |
| CN | 204428144 | U | 7/2015 |
| CN | 204428145 | U | 7/2015 |
| CN | 204446081 | U | 7/2015 |
| DE | 202006010241 | U1 | 3/2007 |
| DE | 102007053058 | B3 | 4/2009 |
| EP | 685206 | B1 | 9/2000 |
| EP | 1508316 | B1 | 5/2007 |
| EP | 1897509 | B1 | 7/2009 |
| EP | 2124772 | A1 | 12/2009 |
| EP | 2124832 | B1 | 8/2012 |
| EP | 2632349 | A1 | 9/2013 |
| EP | 2665428 | A1 | 11/2013 |
| EP | 2742878 | A1 | 6/2014 |
| EP | 2750617 | A1 | 7/2014 |
| EP | 2849684 | A1 | 3/2015 |
| EP | 2932925 | A1 | 10/2015 |
| EP | 2624764 | B1 | 12/2015 |
| EP | 3023068 | A2 | 5/2016 |
| FR | 2362616 | A1 | 3/1978 |
| FR | 2764183 | B1 | 11/1999 |
| FR | 2953120 | B1 | 1/2012 |
| FR | 3030221 | A1 | 6/2016 |
| GB | 2154143 | A | 9/1985 |
| GB | 2154144 | A | 9/1985 |
| GB | 2334214 | B | 1/2003 |
| IN | 140/DELNP/2012 | A1 | 1/2013 |
| IN | 2004/KOLNP/2013 | A1 | 1/2013 |
| JP | 63005739 | A | 1/1988 |
| JP | 2004174265 | A | 6/2004 |
| JP | 2006158972 | A | 6/2006 |
| JP | 4134243 | B2 | 8/2008 |
| JP | 2011092405 | A | 5/2011 |
| JP | 2011523889 | A | 8/2011 |
| JP | 4796943 | B2 | 10/2011 |
| JP | 2014511207 | A | 5/2014 |
| JP | 2014521384 | A | 8/2014 |
| KR | 100904142 | B1 | 6/2009 |
| MD | 756 | C2 | 2/1998 |
| RU | 2098036 | C1 | 12/1997 |
| RU | 2195892 | C2 | 1/2003 |
| RU | 2320287 | C1 | 3/2008 |
| RU | 2321366 | C2 | 4/2008 |
| RU | 2321369 | C1 | 4/2008 |
| RU | 2346663 | C2 | 2/2009 |
| RU | 2412662 | C1 | 2/2011 |
| SU | 1333328 | A2 | 8/1987 |
| WO | 0166022 | A1 | 9/2001 |
| WO | 03075775 | A1 | 9/2003 |
| WO | 2004089227 | A2 | 10/2004 |
| WO | 2005009209 | A2 | 2/2005 |
| WO | 2005122923 | A1 | 12/2005 |
| WO | 2008051064 | A1 | 5/2008 |
| WO | 2009029798 | A1 | 3/2009 |
| WO | 2009032101 | A2 | 3/2009 |
| WO | 2011037885 | A1 | 3/2011 |
| WO | 2012029008 | A1 | 3/2012 |
| WO | 2013090392 | A1 | 6/2013 |
| WO | 2013134387 | A1 | 9/2013 |
| WO | 2013169475 | A1 | 11/2013 |
| WO | 2014020561 | A1 | 2/2014 |
| WO | 2014022055 | A1 | 2/2014 |
| WO | 2014035991 | A1 | 3/2014 |
| WO | 2014085882 | A1 | 6/2014 |
| WO | 2014147099 | A1 | 9/2014 |
| WO | 2014152219 | A2 | 9/2014 |
| WO | 2014152535 | A1 | 9/2014 |
| WO | 2014177783 | A1 | 11/2014 |
| WO | 2014200017 | A1 | 12/2014 |
| WO | 2015094409 | A1 | 6/2015 |
| WO | 2015105880 | A1 | 7/2015 |
| WO | 2015127515 | A2 | 9/2015 |
| WO | 2016134160 | A1 | 8/2016 |
| WO | 2017134486 | A1 | 8/2017 |

OTHER PUBLICATIONS

Bauer et al., "Offset-V Osteotomy of the First Metatarsal Shaft in Hallux Abducto Valgus," McGlamrys Comprehensive Textbook of Foot and Ankle Surgery, Fourth Edition, vol. 1, Chapter 29, 2013, 26 pages.

Collan et al., "The biomechanics of the first metatarsal bone in hallux valgus: A preliminary study utilizing a weight bearing extremity CT," Foot and Ankle Surgery, vol. 19, 2013, pp. 155-161.

Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.

Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.

Dayton et al., "Principles of Management of Growth Plate Fractures in the Foot and Ankle," Clinics in Podiatric Medicine and Surgery, Pediatric Foot Deformities, Oct. 2013, 17 pages.

Decarbo et al., "Resurfacing Interpositional Arthroplasty for Degenerative Joint Diseas of the First Metatarsalphalangeal Joint," Podiatry Management, Jan. 2013, pp. 137-142.

Aiyer et al., "Prevalence of Metatarsus Adductus in Patients Undergoing Hallux Valgus Surgery," Foot & Ankle International, vol. 35, No. 12, 2014, pp. 1292-1297.

"Acumed Osteotomiesystem Operationstechnik," Acumed, 2014, 19 pages (including 3 pages English translation).

Catanese et al., "Measuring Sesamoid Position in Hallux Valgus: When Is the Sesamoid Axial View Necessary," Foot and Ankle Specialist, 2014, 3 pages.

Crawford et al., "Metatarsus Adductus: Radiographic and Pathomechanical Analysis," Chapter 5, 2014, 6 pages.

Dayton et al., "Clarification of the Anatomic Definition of the Bunion Deformity," The Journal of Foot and Ankle Surgery, vol. 53, 2014, pp. 160-163.

Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.

Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.

(56) References Cited

OTHER PUBLICATIONS

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton, "Tarsal-Metatarsal Joint: Primary & Revision Arthrodesis," Apr. 2014, 38 pages.
Decarbo et al., "Locking Plates: Do They Prevent Complications?," Podiatry Today, Apr. 2014, 7 pages.
Decarbo et al., "The Weil Osteotomy: A Refresher," Techniques in Foot and Ankle Surgery, vol. 13, No. 4, Dec. 2014, pp. 191-198.
Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Dalat et al., "Does arthrodesis of the first metatarsophalangeal joint correct the intermetatarsal M1M2 angle? Analysis of a continuous series of 208 arthrodeses fixed with plates," Orthopaedics & Traumatology: Surgery & Research, vol. 101, 2015, pp. 709-714.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "Complications of Metatarsal Suture Techniques for Bunion Correction: A Systematic Review of the Literature," The Journal of Foot and Ankle Surgery, Article in Press, 2015, 3 pages.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
Chesser et al., "New Advances With The Tarsometatarsal Arthrodesis," Podiatry Today, vol. 30, No. 10, Sep. 27, 2017, 15 pages.
Dayton et al., "Comparison of Tibial Sesamoid Position on Anteroposterior and Axial Radiographs Before and After Triplane Tarsal Metatarsal Joint Arthrodesis," The Journal of Foot & Ankle Surgery, vol. 56, 2017, pp. 1041-1046.
Dayton et al., "Evidence-Based Bunion Surgery: A Critical Examination of Current and Emerging Concepts and Techniques," Springer International Publishing, 2017, 254 pages.
"Accu-Cut Osteotomy Guide System," BioPro, Brochure, Oct. 2018, 2 pages.
Buda et al., "Effect of Fixation Type and Bone Graft on Tarsometatarsal Fusion," Foot & Ankle International, vol. 39, No. 12, 2018, pp. 1394-1402.
Dayton et al., "Biomechanical Characteristics of Biplane Multiplanar Tension-Side Fixation for Lapidus Fusion," The Journal of Foot & Ankle Surgery, vol. 57, 2018, pp. 761-765.
Dayton et al., "Progression of Healing on Serial Radiographs Following First Ray Arthrodesis in the Foot Using a Biplanar Plating Technique Without Compression," The Journal of Foot & Ankle Surgery, 2018, 7 pages.
"Arthrodesis of the Tarsometatarsal Joint," Retrieved from https://musculoskeletalkey.com/arthrodesis-of-the-tarsometatarsal-joint/, posted Apr. 18, 2019, 11 pages.
Bennett et al., "Intraosseous Sliding Plate Fixation Used in Double Osteotomy Bunionectomy," Foot & Ankle International, vol. 40, No. 1, 2019, pp. 85-88.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
Chomej et al., "Lateralising Dmmo (Mis) for simultaneous correction of a pes adductus during surgical treatment of a hallux valgus," The Foot, vol. 45, Dec. 2020, 33 pages.
Conti et al., "Effect of the Modified Lapidus Procedure for Hallux Valgus on Foot Width," Foot & Ankle International, Feb. 1, 2020, published online: Oct. 30, 2019, 6 pages.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Dayton et al., "Comparison of Radiographic Measurements Before and After Triplane Tarsometatarsal Arthrodesis for Hallux Valgus," The Journal of Foot & Ankle Surgery, vol. 59, 2020, pp. 291-297.
Deheer et al., "Procedure-Specific Hardware Removal After Evans Osteotomy," Journal of the American Podiatric Medical Association, vol. 110, No. 2, Mar./Apr. 2020, 7 pages.
Cichero et al., "Different fixation constructs and the risk of nonunion following first metatarsophalangeal joint arthrodesis," Foot and Ankle Surgery, vol. 27, 2021, pp. 789-792.
Curran et al., "Functional Capabilities After First Metatarsal Phalangeal Joint Arthrodesis Using a Locking Plate and Compression Screw Construct," The Journal of Foot & Ankle Surgery, vol. 61, No. 1, Jan./Feb. 2022, pp. 79-83.
Boffeli et al., "Can We Abandon Saw Wedge Resection in Lapidus Fusion? A Comparative Study of Joint Preparation Techniques Regarding Correction of Deformity, Union Rate, and Preservation of First Ray Length," The Journal of Foot and Ankle Surgery, vol. 58, No. 6, Nov. 2019, published online: Sep. 25, 2019, pp. 1118-1124.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
TempFix Spanning the Ankle Joint Half Pin and Transfixing Pin Techniques, Biomet Orthopedics, Surgical Technique, 2012, 16 pages.
"Speed Continuous Active Compression Implant," BioMedical Enterprises, Inc., A120-029 Rev. 3, 2013, 4 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Otsuki et al., "Developing a novel custom cutting guide for curved per-acetabular osteotomy," International Orthopaedics (SICOT), vol. 37, 2013, pp. 1033-1038.
Peters et al., "Flexor Hallucis Longus Tendon Laceration as a Complication of Total Ankle Arthroplasty," Foot & Ankle International, vol. 34, No. 1, 2013, pp. 148-149.
Prophecy Inbone Preoperative Navigation Guides, Wright Medical Technology, Inc., Nov. 2013, 6 pages.

(56) References Cited

OTHER PUBLICATIONS

Rayhack Ulnar Shortening Generation II Low-Profile Locking System Surgical Technique, Wright Medical Technology, Inc., Dec. 2013, 20 pages.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Siddiqui et al. "Fixation Of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Williams et al., "Metatarsus adductus: Development of a non-surgical treatment pathway," Journal of Paediatrics and Child Health, vol. 49, 2013, pp. E428-433.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Pentikainen et al., "Preoperative Radiological Factors Correlated to Long-Term Recurrence of Hallux Valgus Following Distal Chevron Osteotomy," Foot & Ankle International, vol. 35, No. 12, 2014, pp. 1262-1267.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Rx-Fix Mini Rail External Fixator, Wright Medical Technology, Brochure, Aug. 15, 2014, 2 pages.
Small Bone External Fixation System, Acumed, Surgical Technique, Effective date Sep. 2014, 8 pages.
"Smith & Nephew scores a HAT-TRICK with its entry into the high-growth hammer toe repair market," Smith & Nephew, Jul. 31, 2014, 2 pages.
"Reconstructive Surgery of the Foot & Ankle," The Podiatry Institute, Update 2015, Conference Program, May 2015, 28 pages.
Simons et al., "Short-Term Clinical Outcome of Hemiarthroplasty Versus Arthrodesis for End-Stage Hallux Rigidus," The Journal of Foot & Ankle Surgery, vol. 54, 2015, pp. 848-851.
Stableloc External Fixation System, Acumed, Product Overview, Effective date Sep. 2015, 4 pages.
Yasuda et al., "Proximal Supination Osteotomy of the First Metatarsal for Hallux Valgus," Foot and Ankle International, vol. 36, No. 6, Jun. 2015, pp. 696-704.
Smith et al., "Intraoperative Multiplanar Alignment System to Guide Triplanar Correction of Hallux Valgus Deformity," Techniques in Foot & Ankle Surgery, 2017, 8 pages.
Santrock et al., "Hallux Valgus Deformity and Treatment: A Three-Dimensional Approach: Lapiplasty," Foot & Ankle Clinics, vol. 23, No. 2, 2018, pp. 281-295.
Smith et al., "Understanding Frontal Plane Correction in Hallux Valgus Repair," Clinics in Podiatric Medicine and Surgery, vol. 35, 2018, pp. 27-36.
Ray et al., "Hallux Valgus," Foot & Ankle Orthopaedics, vol. 4, No. 2, 2019, pp. 1-12.
Ray et al., "Multicenter Early Radiographic Outcomes of Triplanar Tarsometatarsal Arthrodesis With Early Weightbearing," Foot & Ankle International, vol. 40, No. 8, 2019, pp. 955-960.
Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.
Shima et al., "Operative Treatment for Hallux Valgus With Moderate to Severe Metatarsus Adductus," Foot & Ankle International, vol. 40, No. 6, 2019, pp. 641-647.
Walker et al., "The Role of First Ray Insufficiency in the Development of Metatarsalgia," Foot and Ankle Clinics, vol. 24, No. 4, Dec. 2019, published online: Sep. 5, 2019, pp. 641-648.
Park et al., "Comparative analysis of clinical outcomes of fixed-angle versus variable-angle locking compression plate for the treatment of Lisfranc injuries," Foot and Ankle Surgery, vol. 26, 2020, pp. 338-342.
Vaida et al., "Effect on Foot Width With Triplanar Tarsometatarsal Arthrodesis for Hallux Valgus," Foot & Ankle Orthopaedics, vol. 5, No. 3, 2020, pp. 1-5.
Weigelt et al., "Risk Factors for Nonunion After First Metatarsophalangeal Joint Arthrodesis With a Dorsal Locking Plate and Compression Screw Construct: Correction of Hallux Valgus Is Key," The Journal of Foot & Ankle Surgery, vol. 60, No. 6, Nov./Dec. 2021, pp. 1179-1183.
Defendant Fusion Orthopedics LLC's Invalidity Contentions, No. CV-22-00490-PHX-SRB, US District Court for the District of Arizona, Aug. 27, 2022, 41 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Stewart, "Use for BME Speed Nitinol Staple Fixation for the Lapidus Procedure,"date unknown, 1 page.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
International Searching Authority "International Search Report and Written Opinion" From Application No. PCT/US23/63299, mailed Oct. 6, 2023, pp. 15.
Lapidus, "The Author's Bunion Operation From 1931 to 1959," Clinical Orthopaedics, vol. 16, 1960, pp. 119-135.
Hardy et al., "Observations on Hallux Valgus," The Journal of Bone and Joint Surgery, vol. 33B, No. 3, Aug. 1951,pp. 376-391.
Mizuno et al., "Detorsion Osteotomy of the First Metatarsal Bone in Hallux Valgus," Japanese Orthopaedic Association, Tokyo, 1956; 30:813-819.
Carr et al., "Correctional Osteotomy for Metatarsus Primus Varus and Hallux Valgus," The Journal of Bone and Joint Surgery, vol. 50-A, No. 7, Oct. 1968, pp. 1353-1367.
D'Amico et al., "Motion of the First Ray: Clarification Through Investigation," Journal of the American Podiatry Association, vol. 69, No. 1, Jan. 1979, pp. 17-23.

(56) References Cited

OTHER PUBLICATIONS

Alvine et al., "Peg and Dowel Fusion of the Proximal Interphalangeal Joint," Foot & Ankle, vol. 1, No. 2, 1980, pp. 90-94.
Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.
Sokoloff, "Lapidus Procedure," Textbook of Bunion Surgery, Chapter 15, 1981, pp. 277-287.
Ghali et al., "The Management of Metatarsus Adductus et Supinatus," The Journal of Bone and Joint Surgery, vol. 66-B, No. 3, May 1984, pp. 376-380.
La Reaux et al., "Metatarsus adductus and hallux abducto valgus: their correlation," The Journal of Foot Surgery, vol. 26, No. 4, Jul. 1987, pp. 304-308, Abstract Only.
Dinapoli et al., "Metatarsal Osteotomy for the Correction of Metatarsus Adductus," Reconstructive Surgery of the Foot and Leg, 1989, pp. 242-250.
Odenbring et al., "A guide instrument for high tibial osteotomy," Acta Orthopaedica Scandinavica, vol. 60, No. 4, 1989, pp. 449-451.
Eustace et al., "Hallux valgus, first metatarsal pronation and collapse of the medial longitudinal arch—a radiological correlation," Skeletal Radiology, vol. 23, 1994, pp. 191-194.
Dayton et al., "Biwinged Excision for Round Pedal Lesions," The Journal of Foot and Ankle Surgery, vol. 35, No. 3, 1996, pp. 244-249.
Myerson, "Cuneiform-Metatarsal Arthrodesis," The Foot and Ankle, Chapter 9, 1997, pp. 107-117.
Talbot et al., "Assessing Sesamoid Subluxation: How Good is the AP Radiograph?," Foot and Ankle International, vol. 19, No. 8, Aug. 1998, pp. 547-554.
Coughlin, "Fixation of the Lapidus Arthrodesis with a Plantar Interfragmentary Screw and Medial Low Profile Locking Plate," Orthopaedics and Traumatology, vol. 7, 1999, pp. 133-143.
Bednarz et al., "Modified Lapidus Procedure for the Treatment of Hypermobile Hallux Valgus," Foot & Ankle International, vol. 21, No. 10, Oct. 2000, pp. 816-821.
Blomer, "Knieendoprothetik—Herstellerische Probleme und technologische Entwicklungen," Orthopade, vol. 29, 2000, pp. 688-696, including English Abstract on p. 689.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Gotte, "Entwicklung eines Assistenzrobotersystems fr die Knieendoprothetik," Forschungsberichte, Technische Universitat Munchen, 165, 2002, 11 pages, including partial English Translation.
Patient to Patient Precision, Accu-Cut, Osteotomy Guide System, BioPro, Foot & Ankle International Journal, vol. 23, No. 8, Aug. 2002, 2 pages.
Schon et al., "Cuneiform-Metatarsal Arthrodesis for Hallux Valgus," The Foot and Ankle, Second Edition, Chapter 8, 2002, pp. 99-117.
Wendl et al., "Navigation in der Knieendoprothetik," OP-Journal, vol. 17, 2002, pp. 22-27, including English Abstract.
Dayton et al., "Use of the Z Osteotomy for Tailor Bunionectomy," The Journal of Foot and Ankle Surgery, vol. 42, No. 3, May/Jun. 2003, pp. 167-169.
Ferrari et al., "A Radiographic Study of the Relationship Between Metatarsus Adductus and Hallux Valgus," The Journal of Foot and Ankle Surgery, vol. 42, No. 1, 2003, pp. 9-14.
Whipple et al., "Zimmer Herbert Whipple Bone Screw System: Surgical Techniques for Fixation of Scaphoid and Other Small Bone Fractures," Zimmer, 2003, 59 pages.
Anderson et al., "Uncemented STAR Total Ankle Prostheses," The Journal of Bone and Joint Surgery, vol. 86(1, Suppl 2), Sep. 2004, pp. 103-111, (Abstract Only).
Coetzee et al., "The Lapidus Procedure: A Prospective Cohort Outcome Study," Foot & Ankle International, vol. 25, No. 8, Aug. 2004, pp. 526-531.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
Flavin et al., "Arthrodesis of the First Metatarsophalangeal Joint Using a Dorsal Titanium Contoured Plate," Foot & Ankle International, vol. 25, No. 11, Nov. 2004, pp. 783-787.
Grondal et al., "A Guide Plate for Accurate Positioning of First Metatarsophalangeal Joint during Fusion," Operative Orthopdie Und Traumatologie, vol. 16, No. 2, 2004, pp. 167-178 (Abstract Only).
Lag Screw Target Bow, Stryker Leibinger GmbH & Co. KG, Germany 2004, 8 pages.
Machacek Jr. et al., "Salvage of a Failed Keller Resection Arthroplasty," The Journal of Bone and Joint Surgery, vol. 86A, No. 6, Jun. 2004, pp. 1131-1138.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
Weber et al., "A Simple System For Navigation Of Bone Alignment Osteotomies Of The Tibia," International Congress Series, vol. 1268, Jan. 2004, pp. 608-613, (Abstract Only).
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Garthwait, "Accu-Cut System Facilitates Enhanced Precision," Podiatry Today, vol. 18, No. 6, Jun. 2005, 6 pages.
Wukich et al., "Hypermobility of the First Tarsometatarsal Joint," Foot and Ankle Clinics, vol. 10, No. 1, Mar. 2005, pp. 157-166.
Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.
Hoffmann II Compact External Fixation System, Stryker, Brochure, Literature No. 5075-1-500, 2006, 12 pages.
Stahl et al., "Derotation Of Post-Traumatic Femoral Deformities By Closed Intramedullary Sawing," Injury, vol. 37, No. 2, Feb. 2006, pp. 145-151, (Abstract Only).
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Easley et al., "Current Concepts Review: Hallux Valgus Part II: Operative Treatment," Foot and Ankle International, vol. 28, No. 6, Jun. 2007, pp. 748-758.
Gregg et al., "Plantar plate repair and Weil osteotomy for metatarsophalangeal joint instability," Foot and Ankle Surgery, vol. 13, 2007, pp. 116-121.
Greiner, "The Jargon of Pedal Movements," Foot & Ankle International, vol. 28, No. 1, Jan. 2007, pp. 109-125.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.

(56) References Cited

OTHER PUBLICATIONS

Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Futura Forefoot Implant Arthroplasty Products, Tornier, Inc., 2008, 14 pages.
Gerard et al., "The Modified Lapidus Procedure," Orthopedics, vol. 31, No. 3, Mar. 2008, 7 pages.
Hetherington et al., "Evaluation of surgical experience and the use of an osteotomy guide on the apical angle of an Austin osteotomy," The Foot, vol. 18, 2008, pp. 159-164.
Hoffmann II Micro Lengthener, Stryker, Operative Technique, Literature No. 5075-2-002, 2008, 12 pages.
Okuda et al., "Proximal Metatarsal Osteotomy for Hallux Valgus: Comparison of Outcome for Moderate and Severe Deformities, Foot and Ankle International," vol. 29, No. 7, Jul. 2008, pp. 664-670.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Visionaire: Patient Matched Cutting Blocks Surgical Procedure," Smith & Nephew, Inc., 2009, 2 pages.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Easley et al., "What is the Best Treatment for Hallux Valgus?," Evidence-Based Orthopaedics—The Best Answers to Clinical Questions, Chapter 73, 2009, pp. 479-491.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Vitek, "Neue Techniken in der Fuchirurgie Das V-tek-System," ABW Wissenschaftsverlag GmbH, 2009, 11 pages, including English Abstract.
Dayton et al., "The Extended Knee Hemilithotomy Position for Gastrocnemius Recession," The Journal of Foot and Ankle Surgery, vol. 49, 2010, pp. 214-216.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Magin, "Computernavigierter Gelenkersatz am Knie mit dem Orthopilot," Operative Orthopdie und Traumatologie, vol. 22, No. 1, 2010, pp. 63-80, including English Abstract on p. 64.
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
MiniRail System, Small Bone Innovations, Surgical Technique, 2010, 24 pages.
Nix et al., "Prevalence of hallux valgus in the general population: a systematic review and meta-analysis," Journal of Foot and Ankle Research, vol. 3, No. 21, 2010, 9 pages.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Stamatis et al., "Mini Locking Plate as Medial Buttress for Oblique Osteotomy for Hallux Valgus," Foot & Ankle International, vol. 31, No. 10, Oct. 2010, pp. 920-922.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Bouaicha et al., "Fixation of Maximal Shift Scarf Osteotomy with Inside-Out Plating: Technique Tip," Foot & Ankle International, vol. 32, No. 5, May 2011, pp. 567-569.
Coetzee et al., "Revision Hallux Valgus Correction," Operative Techniques in Foot and Ankle Surgery, Section I, Chapter 15, 2011, pp. 84-96.
Dayton et al., "A User-Friendly Method of Pin Site Management for External Fixators," Foot and Ankle Specialist, Sep. 16, 2011, 4 pages.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Hunt et al., "Locked Versus Nonlocked Plate Fixation For Hallux MTP Arthrodesis," Foot and Ankle International, vol. 32, No. 7, Jul. 2011, pp. 704-709.
Le et al., "Tarsometatarsal Arthrodesis," Operative Techniques in Foot and Ankle Surgery, Section II, Chapter 40, 2011, pp. 281-285.
Shurnas et al., "Proximal Metatarsal Opening Wedge Osteotomy," Operative Techniques in Foot and Ankle Surgery, Section I, Chapter 13, 2011, pp. 73-78.
Weil et al., "Anatomic Plantar Plate Repair Using the Weil Metatarsal Osteotomy Approach," Foot & Ankle Specialist, vol. 4, No. 3, 2011, pp. 145-150.
Wienke et al., "Bone Stimulation For Nonunions: What the Evidence Reveals," Podiatry Today, vol. 24, No. 9, Sep. 2011, pp. 52-57.
Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Giannoudis et al., "Hallux Valgus Correction," Practical Procedures in Elective Orthopaedic Surgery, Pelvis and Lower Extremity, Chapter 38, 2012, 22 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Integra, "Integra Large Qwix Positioning and Fixation Screw, Surgical Technique," 2012, 16 pages.
Kim et al., "A Multicenter Retrospective Review of Outcomes for Arthrodesis, Hemi-Metallic Joint Implant, and Resectional Arthroplasty

(56) References Cited

OTHER PUBLICATIONS in the Surgical Treatment of End-Stage Hallux Rigidus," The Journal of Foot and Ankle Surgery, vol. 51, 2012, pp. 50-56.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Mortier et al., "Axial Rotation of the First Metatarsal Head in a Normal Population and Hallux Valgus Patients," Orthopaedics and Traumatology: Surgery and Research, vol. 98, 2012, pp. 677-683.
Tricot et al., "3D-corrective osteotomy using surgical guides for posttraumatic distal humeral deformity," Acta Orthopaedica Belgica, vol. 78, No. 4, 2012, pp. 538-542.
"Foot and Ankle Instrument Set," Smith & Nephew, 2013, 2 pages.
Didomenico et al., "Lapidus Bunionectomy: First Metatarsal-Cuneiform Arthrodesis," McGlamrys Comprehensive Textbook of Foot and Ankle Surgery, Fourth Edition, vol. 1, Chapter 31, 2013, 24 pages.
Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
Fishco, "A Straightforward Guide To The Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.
Gutteck et al., "Comparative study of Lapidus bunionectomy using different osteosynthesis methods," Foot and Ankle Surgery, vol. 19, 2013, pp. 218-221.
Gutteck et al., "Is it feasible to rely on intraoperative X ray in correcting hallux valgus?," Archives of Orthopaedic and Trauma Surgery, vol. 133, 2013, pp. 753-755.
Klos et al., "Modified Lapidus arthrodesis with plantar plate and compression screw for treatment of hallux valgus with hypermobility of the first ray: A preliminary report," Foot and Ankle Surgery, vol. 19, 2013, pp. 239-244.
Modular Rail System: External Fixator, Smith & Nephew, Surgical Technique, 2013, 44 pages.
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Fishco, "Making the Lapidus Easy," The Podiatry Institute, Update 2014, Chapter 14, 2014, pp. 91-93.
Groves, "Operative Report," St. Tammany Parish Hospital, Date of Procedure, Mar. 26, 2014, 2 pages.
HAT-TRICK Lesser Toe Repair System, Foot and Ankle Technique Guide, Metatarsal Shortening Osteotomy Surgical Technique, Smith & Nephew, 2014, 16 pages.
HAT-TRICK Lesser Toe Repair System, Smith & Nephew, Brochure, Aug. 2014, 12 pages.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
Hoffmann Small System External Fixator Orthopedic Instruments, Stryker, retrieved Dec. 19, 2014, from the Internet: <http://www.alibaba.com/product-detail/Stryker-Hoffmann-Small-System-External-Fixator_1438850129.html>, 3 pages.
Lieske et al., "Implantation einer Sprunggelenktotalendo-prothese vom Typ Salto 2," Operative Orthopdie und Traumatologie, vol. 26, No. 4, 2014, pp. 401-413, including English Abstract on p. 403.
Little, "Joint Arthrodesis For Hallux Valgus," Clinics in Podiatric Medicine and Surgery, Hallux Abducto Valgus Surgery, updated Apr. 19, 2014, retrieved online from < https://www.footankleinstitute.com/first-metatarsophalangeal-joint-arthrodesis-in-the-treatment-of-hallux-valgus>, 7 pages.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Magin, "Die belastungsstabile Lapidus-Arthrodese bei Hallux-valgus-Deformitt mittels IVP-Plattenfixateur (V-TEK-System)," Operative Orthopdie und Traumatologie, vol. 26, No. 2, 2014, pp. 184-195, including English Abstract on p. 186.
Mini Joint Distractor, Arthrex, retrieved Dec. 19, 2014, from the Internet: <http://www.arthrex.com/foot-ankle/mini-joint-distractor/products>, 2 pages.
Nagy et al., "The AO Ulnar Shortening Osteotomy System Indications and Surgical Technique," Journal of Wrist Surgery, vol. 3, No. 2, 2014, pp. 91-97.
Fallin et al., US Provisional Application Entitled Indexed Tri-Planar Osteotomy Guide and Method, U.S. Appl. No. 62/118,378, filed Feb. 19, 2015, 62 pages.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.
Groves, "Functional Position Joint Sectioning: Pre-Load Method for Lapidus Arthrodesis," The Podiatry Institute, Update 2015, Chapter 6, 2015, pp. 23-29.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
Fraissler et al., "Treatment of hallux valgus deformity," Efort Open Reviews, vol. 1, Aug. 2016, pp. 295-302.
Jeuken et al., "Long-term Follow-up of a Randomized Controlled Trial Comparing Scarf to Chevron Osteotomy in Hallux Valgus Correction," Foot & Ankle International, vol. 37, No. 7, 2016, pp. 687-695.
Ho et al., "Hallux rigidus," Efort Open Reviews, vol. 2, Jan. 2017, pp. 13-20.
Fazal et al., "First metatarsophalangeal joint arthrodesis with two orthogonal two hole plates," Acta Orthopaedica et Traumatologica Turcica, vol. 52, 2018, pp. 363-366.
Hatch et al., "Triplane Hallux Abducto Valgus Classification," The Journal of Foot & Ankle Surgery, vol. 57, No. 5, Sep./Oct. 2018, published online: May 18, 2018, pp. 972-981.
Marshall et al., "The identification and appraisal of assessment tools used to evaluate metatarsus adductus: a systematic review of their measurement properties," Journal of Foot and Ankle Research, vol. 11, No. 25, 2018, 10 pages.
Latif et al., "First metatarsophalangeal fusion using joint specific dorsal plate with interfragmentary screw augmentation: Clinical and radiological outcomes," Foot and Ankle Surgery, vol. 25, 2019, pp. 132-136.
Lopez et al., "Metatarsalgia: Assessment Algorithm and Decision Making," Foot and Ankle Clinics, vol. 24, No. 4, Dec. 2019, published online: Sep. 25, 2019, pp. 561-569.
Miller et al., "Variable Angle Locking Compression Plate as Alternative Fixation for Jones Fractures: A Case Series," Kansas Journal of Medicine, vol. 12, No. 2, May 2019, pp. 28-32.
Hatch et al., "Analysis of Shortening and Elevation of the First Ray With Instrumented Triplane First Tarsometatarsal Arthrodesis," Foot & Ankle Orthopaedics, vol. 5, No. 4, 2020, pp. 1-8.
Kurup et al., "Midfoot arthritis—current concepts review," Journal of Clinical Orthopaedics and Trauma, vol. 11, 2020, pp. 399-405.
Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.

(56) References Cited

OTHER PUBLICATIONS

Li et al., "Evolution of Thinking of the Lapidus Procedure and Fixation," Foot and Ankle Clinics, vol. 25, No. 1, Mar. 2020, published online: Dec. 16, 2019, pp. 18 pages.
Gould et al., "A Prospective Evaluation of First Metatarsophalangeal Fusion Using an Innovative Dorsal Compression Plating System," The Journal of Foot & Ankle Surgery, vol. 60, 2021, pp. 891-896.
Jackson III et al., "The Surgical Learning Curve for Modified Lapidus Procedure for Hallux Valgus Deformity," Foot & Ankle Specialist, Jul. 2021, 5 pages.
Mcaleer et al., "A systematic approach to the surgical correction of combined hallux valgus and metatarsus adductus deformities," The Journal of Foot & Ankle Surgery, May 21, 2021, 6 pages.
Mccabe et al., "Anatomical reconstruction of first ray instability hallux valgus with a medial anatomical TMTJ1 plate," Foot and Ankle Surgery, vol. 27, No. 8, Dec. 2021, pp. 869-873.
Mehtar et al., "Outcomes of bilateral simultaneous hallux MTPJ fusion," Foot and Ankle Surgery, vol. 27, 2021, pp. 213-216.
Ferreyra et al., "Can we correct first metatarsal rotation and sesamoid position with the 3D Lapidus procedure?," Foot and Ankle Surgery, vol. 28, No. 3, Apr. 2022, pp. 313-318.
Mcaleer et al., "Radiographic Outcomes Following Triplanar Correction of Combined Hallux Valgus and Metatarsus Adductus Deformities," ACFAS Scientific Conference, Poster, Feb. 2022, 1 page.
Michelangelo Bunion System, Surgical Technique, Instratek Incorporated, publication date unknown, 4 pages.

* cited by examiner

DEVICES AND TECHNIQUES FOR TREATING LESSER METATARSALS OF THE FOOT

CROSS-REFERENCE

This application claims the benefit of U.S. Provisional Patent Application No. 63/406,486, filed Sep. 14, 2022, and U.S. Provisional Patent Application No. 63/313,726, filed Feb. 24, 2022, the entire contents of each of which are incorporated herein by reference.

TECHNICAL FIELD

This disclosure relates to devices and techniques for treating bones of the foot, such as one or more lesser metatarsals of the foot.

BACKGROUND

Metatarsus adductus (MTA) is a deformity of the foot in which the metatarsals are angulated into adduction. MTA is typically characterized by a medial deviation of the metatarsals in the transverse plane. For example, MTA is often described as a structural deformity occurring at the Lisfranc joint (tarsometatarsal joints), with the metatarsals being deviated medially with reference to the lesser tarsus.

In some patients, MTA presents with hallux valgus, also referred to as hallux abducto valgus. Hallux valgus is a complex progressive condition that is characterized by lateral deviation (valgus, abduction) of the hallux and medial deviation of the first metatarsophalangeal joint. Hallux valgus typically results in an increase in the hallux adductus angle, which is the angle between the long axes of the first metatarsal and proximal phalanx in the transverse plane.

In some cases, surgical intervention is needed to address MTA, hallux valgus, and/or other conditions of the foot. Surgical instruments that can facilitate efficient, accurate, and reproducible clinical results are useful for practitioners performing orthopedic surgical procedures techniques.

SUMMARY

In general, this disclosure is directed to devices and techniques involving realignment and/or fusion of one or more bones in the foot. For example, various devices and techniques may be utilized to treat metatarsus adductus (MTA), hallux valgus, arthritis, and/or other conditions of the foot. In some implementations, the devices and techniques are configured for use on one or more lesser metatarsals and/or lesser tarsometatarsal (TMT) joint, such as one or more of the second, third, fourth, and/or fifth metatarsals and/or one or more of the intermediate cuneiform, lateral cuneiform, and/or cuboid. For example, one or more cut guides, compressor-distractor devices, and/or other instruments may be designed to accommodate the specific anatomical conditions of one or more lesser metatarsals and/or TMT joints of the foot.

In some examples, surgical devices and/or techniques described herein may be implemented on a second and/or third TMT joint. For example, a clinician may surgically access the second and/or third tarsometatarsal joints of the foot to prepare the joints for realignment and fusion. The clinician may make an incision, e.g., providing dorsolateral and dorsomedial access, to the second and/or third tarsometatarsal joints. With the joints exposed, the clinician may prepare the end faces of the second and/or third metatarsals and opposed intermediate and/or lateral cuneiforms, respectively. Before or after preparing the one or more joints, the clinician may realign one or more lesser metatarsals in the transverse plane, frontal plane, and/or sagittal plane to realign the metatarsal. Additionally or alternatively, the clinician may compress the prepared end faces of the bones together. After suitable preparation and repositioning, the clinician can fixate one or more of the joins to promote fusion across the joints.

In some implementations, the second and third tarsometatarsal joints are prepared and the second and third metatarsals independently moved from each other in one or more planes, such as the transverse plane. In other implementations, the second and third tarsometatarsal joints can be prepared and the second and third metatarsals moved together to address the angular misalignment of the metatarsals. For example, when accessing and preparing the second and third tarsometatarsal joints, the plantar tarsometatarsal ligaments and the ligaments between the second and third metatarsals may be preserved (e.g., remain uncut or unbroken). This can maintain the connective tissue between the second and third metatarsals, allowing the second and third metatarsals to be manipulated as an interconnected block or group during angular realignment. In addition to realigning the second and third metatarsals, the fourth and fifth metatarsals may or may not also be realigned to help correct a bone deformity, such as metatarsus adductus.

While a surgical technique according to the disclosure may involve surgically accessing and preparing multiple lesser tarsometatarsal joints of the foot, such as the second and third tarsometatarsal joints, in some implementations a technique can be performed on a single lesser tarsometatarsal joint (e.g., the second tarsometatarsal joint, the third tarsometatarsal joint, the fourth tarsometatarsal joint, and/or the fifth tarsometatarsal joint). This procedure on the single lesser tarsometatarsal joint may be performed either alone or in combination with treatment of hallux valgus on the first metatarsal. For example, a MTA deformity or other bone deformity may be corrected by operating on a single lesser tarsometatarsal joint (e.g., the second tarsometatarsal joint, the third tarsometatarsal joint) without operating on other lesser tarsometatarsal joints, again optionally with alignment correction of the first metatarsal through a procedure performed on the first tarsometatarsal joint. In yet other examples, a clinician may utilize instruments and/or techniques according to the disclosure on the first metatarsal and/or first TMT joint without performing a surgical procedure on a lesser metatarsal and/or lesser TMT joint.

Independent of the specific surgical technique performed during a treatment procedure, a variety of different instruments may be provided to help facilitate bone preparation and/or realignment techniques. The instruments may be utilized as part of a metatarsal adductus treatment procedure or yet other treatment procedure (e.g., fusion of an arthritic joint, realignment of a bone other than a metatarsal). For example, a bone cutting guide may be used to help cut an end face of a metatarsal and/or cuneiform to facilitate realignment and/or fusion between bones. In general, the bone cutting guide may be sized and shaped to be positioned over one or more bones to be cut. The bone cutting guide may define at least one guide surface along which a cutting instrument can be guided to cut a bone in a plane parallel to the guide surface. For example, the bone cutting guide may define a pair of guide surfaces defining a cutting slot there between through which a cutting instrument can be inserted.

In some examples, a compressor-distractor is utilized during a surgical procedure to control repositioning of one or more lesser metatarsals and/or compress the end face of a prepared lesser metatarsal against an end face of an opposed cuneiform. The compressor-distractor may be configured with engagement arms having a straight portion and an angled portion. The compressor-distractor can be positioned extending dorsally and laterally via the straight arm portions and then turn to extend plantarly and laterally via the angled arm portions. This can follow the anatomical curvature of the lateral portion of the foot, positioning an actuator of the compressor-distractor on a lateral side of the foot and out of interference with the lesser metatarsal joint(s) being worked on during the surgical procedure.

In some examples, a bone cutting guide configured for a surgical procedure (e.g., metatarsal adductus procedure, fusion of an arthritic joint) may have a guide surface for guiding cutting of a single bone or may be configured to guide a cutting instrument to cut multiple different bones. For example, the bone cutting guide may include at least one guide surface (e.g., at least one cutting slot) to guide a cutting instrument to cut an end of a metatarsal and at least one additional guide surface (e.g., at least one additional cutting slot) to guide a cutting instrument to cut an end of an opposed cuneiform. The guide surfaces may be parallel to each other to provide parallel cuts across the end faces of the metatarsal and opposed cuneiform. This configuration may be useful, for example, when performing supplemental cutting on a joint and/or when preparing an arthritic joint for fusion.

In some implementations, a bone cutting guide configured for a surgical procedure (e.g., metatarsal adductus procedure, fusion of an arthritic joint) may have a body extending lengthwise from a medial side to a lateral side. The bone cutting guide may include at least one guide surface (e.g., at least one cutting slot) to guide a cutting instrument to cut an end of a metatarsal and/or at least one additional guide surface (e.g., at least one cutting slot) to guide a cutting instrument to cut an end of a cuneiform. In either case, one or both of the medial side and lateral side of the of the bone cutting guide body may define a tissue retraction cavity. The tissue retraction cavity can form a space in which retracted tissue is retained, helping to prevent the retracted tissue from closing over the cutting guide while the cutting guide is positioned over one or more bones to be cut.

For example, to position the bone cutting guide over one or more bones to be cut, the clinician can make an incision through the skin of the patient, retract the skin to enlarge the opening through the skin, and then position the bone cutting guide over one or more bones accessed through the incision. The skin may have a tendency to draw back to its original position along the incision line, potentially causing the skin to overlap the top surface of the bone cutting guide and thereby inhibit cutting performed using the bone cutting guide. Configuring the bone cutting guide with a tissue retraction cavity can help prevent the retracted skin from overlapping and interfering with use of the bone cutting guide.

Independent of whether the bone cutting guide is configured with a tissue retraction space, in some configurations, the bone cutting guide may include a cutout on a lower portion of a sidewall bounding a guide surface of the cutting guide. For example, the bone cutting guide may include a cutout on a lower portion of a medial sidewall bounding a medial extent of a guide surface of the cutting guide. In use, the clinician can advance a cutting instrument along a guide surface, e.g., between a medial sidewall and a lateral sidewall, to cut one or more bones. Upon reaching a sidewall with a lower cutout, the clinician may rotate the cutting instrument through the cutout and under an upper portion of the sidewall bounding the cutout. This can allow the clinician to optionally extend the range of cutting beyond the sidewall(s) of the bone cutting guide. This may be useful, e.g., if the sidewall of the bone cutting guide is positioned slightly offset to an underlying bone and the clinician desires to cut under the sidewall of the bone cutting guide to complete cutting through underlying bone.

In one example, a compressor-distractor is described that includes a first engagement arm, a second engagement arm, and an actuator. The first engagement arm includes a first straight portion and a first angled portion. The first straight portion defines a first pin-receiving hole for receiving a first pin inserted therethrough into a first bone portion. The first angled portion extends at a first acute angle relative to a longitudinal axis defined by the first pin-receiving hole. The second engagement arm includes a second straight portion and a second angled portion. The second straight portion defines a second pin-receiving hole for receiving a second pin inserted therethrough into a second bone portion. The second angled portion extends at a second acute angle relative to a longitudinal axis defined by the second pin-receiving hole. The actuator is operatively coupled to the first engagement arm and the second engagement arm. The actuator is configured to move the first and second engagement arms away from each other to move the first bone portion away from the second bone portion and also being configured to move the first and second engagement arms toward each other to move the first bone portion toward the second bone portion. According to the example, the first straight portion defines a length extending from a first end to a second end, the first angled portion defines a length extending from a first end to a second end, and a ratio of the length of the first straight portion divided by the length of the first angled portion ranges from 0.5 to 1.0.

In another example, a method is described that includes positioning a first pin-receiving hole of a first engagement arm of a compressor-distractor over a first bone portion that is one of an intermediate cuneiform, a lateral cuneiform, and a cuboid. The first engagement arm has a first straight portion defining the first pin-receiving hole and extending dorsally and laterally from the first bone portion and a first angled portion extending plantarly and laterally from the first straight portion. The method also includes positioning a second pin-receiving hole of a second engagement arm of the compressor-distractor over at second bone portion that is one of second metatarsal, a third metatarsal, a fourth metatarsal, or a fifth metatarsal. The second engagement arm has a second straight portion defining the second pin-receiving hole and extending dorsally and laterally from the second bone portion and a second angled portion extending plantarly and laterally from the second straight portion. The method further includes inserting a first pin through the first pin-receiving hole and into the underlying first bone portion, inserting a second pin through the second pin-receiving hole and into the underlying second bone portion, and actuating the compressor-distractor to adjust a separation distance between the first bone portion and the second bone portion.

In another example, a bone cutting guide is described that includes a body extending lengthwise from a medial side to a lateral side and defining a cuneiform-side guide surface and a metatarsal-side guide surface. The cuneiform-side guide surface is configured to be positioned over at least one cuneiform of a foot and to guide a cutting instrument to cut the at least one of cuneiform. The metatarsal-side guide surface is configured to be positioned over at least one metatarsal and to guide the cutting instrument to cut the at least one metatarsal. The example specifies that the medial side of the body defines a tissue retraction cavity.

The details of one or more examples are set forth in the accompanying drawings and the description below. Other features, objects, and advantages will be apparent from the description and drawings, and from the claims.

DETAILED DESCRIPTION

Figure 1B:
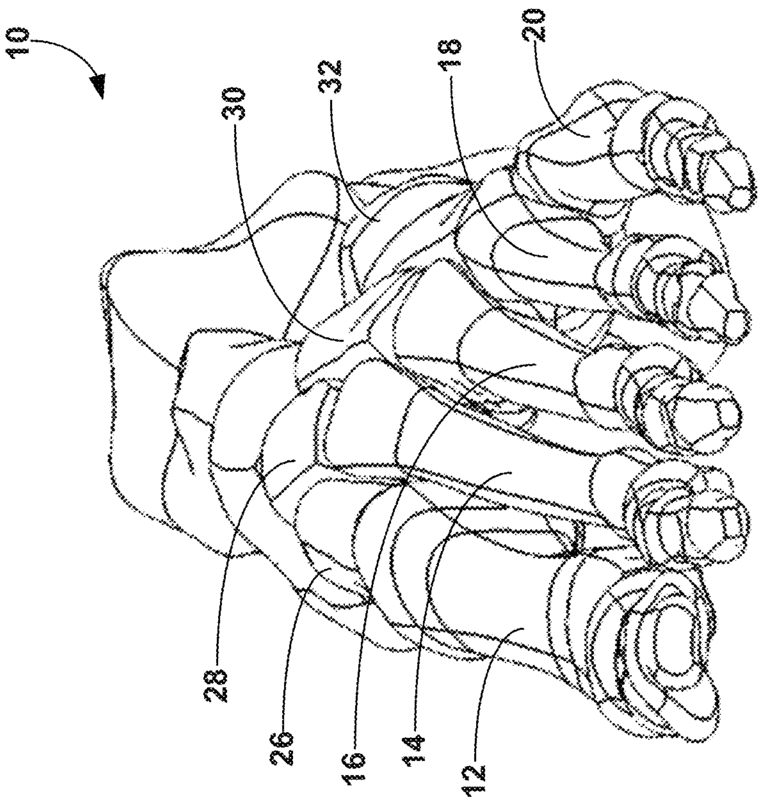
FIGS. 1A and 1B are top and front views, respectively, of a foot showing normal metatarsal alignment positions.

In general, the present disclosure is directed to devices and techniques for preparing one or more tarsometatarsal joints ("TMT joint") for fusion and realigning one or more metatarsals separated from an opposed bone by the tarsometatarsal joint. While a technique according to disclosure can be performed on any TMT joint, in some implementations, a surgical technique is performed on at least the second TMT joint and the third TMT joint. During the procedure, the clinician may cut an end of one or both of the second metatarsal and opposed intermediate cuneiform. Additionally or alternatively, the clinician may cut an end of one or both of the third metatarsal and opposed lateral cuneiform. In some examples the clinician advances a cutting instrument along a path (e.g., a linear path and/or a curved path) to cut one metatarsal end followed by another metatarsal end and/or to cut one cuneiform end followed by another cuneiform end. In either case, a bone portion may be removed from the TMT joint space, such as between both the second TMT joint space and the third TMT joint space. The bone portion and/or space from which the bone portion is removed may be shaped to facilitate subsequent repositioning of the metatarsal relative to the opposed cuneiform, e.g., by moving the metatarsal to partially or fully close the space created upon removal of the bone portion.

Independent of how one or more TMT joints are prepared, the clinician can apply a force to one or more metatarsals, such as the second and/or third metatarsals, to rotate the one or more metatarsals in at least one plane (e.g., one or more of the transverse plane, frontal plane, and/or sagittal plane). When repositioning both the second and third metatarsals, the second and third metatarsals may or may not remain interconnected through ligamentous attachments, such as the plantar ligaments and/or second-to-third intermetatarsal ligaments. When remaining interconnected, the second and third metatarsals may be pivoted together as a block (e.g., in at least one plane, such as the transverse plane). For example, the second and third metatarsals may pivot generally about a medial aspect (e.g., side) of the second TMT joint in the transverse plane, closing a larger opening on the lateral side of the joint. In some implementations, the second and/or third metatarsals may be pivoted in at least the transverse plane with the second metatarsal base being attached to the Lisfranc ligament to serve as a pivot point about which the bone block can rotate. The clinician can pivot the second and third metatarsals by hand and/or with the aid of a bone positioner that engages with at least one of the second and third metatarsals and a bone other than that with which the bone positioner is engaged.

The fourth and fifth metatarsals may also pivot in one or more planes (e.g., at least the transverse plane), such as concurrent with the second and/or third metatarsals being pivoted in one or more planes. The fourth and fifth metatarsals may realign without accessing or preparing the fourth or fifth TMT joints. That being said, in some examples, the fourth and/or fifth metatarsals may be surgically accessed and prepared by preparing an end of the fourth metatarsal and/or opposed cuboid bone and/or an end of the fifth metatarsal and/or opposed cuboid bone. After suitably realigning one or more of the second, third, fourth and/or fifth metatarsals, the moved position of the one or more metatarsals may be fixated. In some examples, a provisional fixation step is performed in which one or more temporary fixation pins are deployed to hold the moved position of one or more metatarsals (e.g., by inserting the fixation pin through one or more moved metatarsal(s) and into one or more adjacent bones). A permanent fixation device can be used to hold a moved position of a bone for subsequent fusion. Example permanent fixation devices include, but are not limited to, pins (e.g., intramedullary nail, K-wire, Steinmann pin), plates, screws, staples, and combinations.

Before, after, or concurrent with preparing and moving one or more lesser metatarsals (e.g., one or more of the second, third, fourth, and/or fifth metatarsals), the clinician may prepare and move the first metatarsal. The clinician may prepare the end of the first metatarsal and also prepare the opposed end of the medial cuneiform. Before or after preparing one or both bone ends, the clinician can move the first metatarsal in one or more planes. For example the clinician may pivot the distal end of the first metatarsal in the transverse plane to close an intermetatarsal angle between the first and second metatarsals. Additionally or alternatively, the clinician may rotate the first metatarsal in the frontal plane and/or adjust the angular alignment of the first metatarsal in the sagittal plane. With the first metatarsal suitably realigned, the clinician can fixate the moved position of the first metatarsal.

Details on example realignment instruments and techniques that can be used in conjunction with the present disclosure are described in U.S. Pat. No. 9,622,805, issued Apr. 18, 2017 and entitled "BONE POSITIONING AND PREPARING GUIDE SYSTEMS AND METHODS," U.S. Pat. No. 10,245,088, issued Apr. 2, 2019 and entitled "BONE PLATING SYSTEM AND METHOD," US Patent Publication No. 2020/0015856, published Jan. 16, 2020 and entitled "COMPRESSOR-DISTRACTOR FOR ANGULARLY REALIGNING BONE PORTIONS," US Patent Publication No. 2020/0015870, published Jan. 16, 2020 and entitled "MULTI-DIAMETER BONE PIN FOR INSTALLING AND ALIGNING BONE FIXATION PLATE WHILE MINIMIZING BONE DAMAGE" and US Patent Publication No. 2021/0361330, published Nov. 25, 2021 and entitled "DEVICES AND TECHNIQUES FOR TREATING METATARSUS ADDUCTUS." The entire contents of each of these patent documents are incorporated herein by reference.

Preparation and fusion of one or more TMT joints may be performed according to the disclosure for a variety of clinical reasons and indications. Preparation and fusion of a TMT joint may be performed to treat metatarsus adductus, hallux valgus, arthritis, and/or other bone and/or joint conditions.

Metatarsus adductus is a deformity of the foot characterized by a transverse plane deformity where the metatarsals are adducted at the Lisfranc joint. The extent of a metatarsus adductus deformity can be characterized by a metatarsus adductus angle. The metatarsus adductus angle can be defined as the angle between the longitudinal axis of the second metatarsal (representing the longitudinal axis of the metatarsus) and the longitudinal axis of the lesser tarsus. The measurement of the longitudinal axis of the lesser tarsus can be characterized by a line perpendicular to the transverse axis of the lesser tarsus using the lateral joint of the fourth metatarsal with the cuboid as a reference.

Hallux valgus, also referred to as hallux abducto valgus, is a complex progressive condition that is characterized by lateral deviation (valgus, abduction) of the hallux and medial deviation of the first metatarsophalangeal joint. Hallux valgus typically results in a progressive increase in the hallux adductus angle, the angle between the long axes of the first metatarsal and proximal phalanx in the transverse plane. An increase in the hallux adductus angle may tend to laterally displace the plantar aponeurosis and tendons of the intrinsic and extrinsic muscles that cross over the first metatarsophalangeal joint from the metatarsal to the hallux. Consequently, the sesamoid bones may also be displaced, e.g., laterally relative to the first metatarsophalangeal joint, resulting in subluxation of the joints between the sesamoid bones and the head of the first metatarsal. This can increase the pressure between the medial sesamoid and the *crista* of the first metatarsal head.

While techniques and devices are described herein particularly in connection with TMT joints of the foot, the techniques and/or devices may be used on other similar bones separated by a joint in the hand or foot. For example, the techniques and devices may be performed on the carpometacarpal joints of the hand. As another example, one or more techniques and/or devices may be used on a metatarsal and/or phalanx, e.g., across a metatarsophalangeal joint. In various implementations, the devices and/or techniques can be used as part of a bone alignment, osteotomy, fusion, fracture repair, and/or other procedure where one or more bones are to be prepared and/or moved to a desired position. For example, the devices and/or techniques may be utilized during an osteotomy procedure in which one bone (e.g., a metatarsal) is cut into a first bone portion and a second bone portion. Accordingly, reference to a metatarsal and an opposed cuneiform herein may be replaced with other bone pairs as described herein.

Further, while the techniques and devices described herein are generally discussed in connection with preparation and fusion of the second and/or third TMT joints, the devices and techniques are not limited to these specific anatomical locations or being performed together. In various examples, devices and/or techniques of the disclosure may be utilized to prepare and promote fusion across a single TMT joint (e.g., the first TMT joint the second TMT joint, the third TMT joint, the fourth TMT joint, the fifth TMT joint) and/or any combination of TMT joints (e.g., the first and second TMT joints; the second and third TMT joints; the first and third TMT joints; the first, second, and third TMT joints; the first and fourth TMT joints; the first, second, and fourth TMT joints, etc.).

To further understand example techniques of the disclosure, the anatomy of the foot will first be described with respect to FIGS. 1-3 along with example misalignments that may occur and be corrected according to the present disclosure. As noted, a bone misalignment may be caused by metatarsus adductus, hallux valgus (bunion), arthritis, and/or other condition. The condition may present with a misalignment of one or more bones in the foot.

Figure 1A:
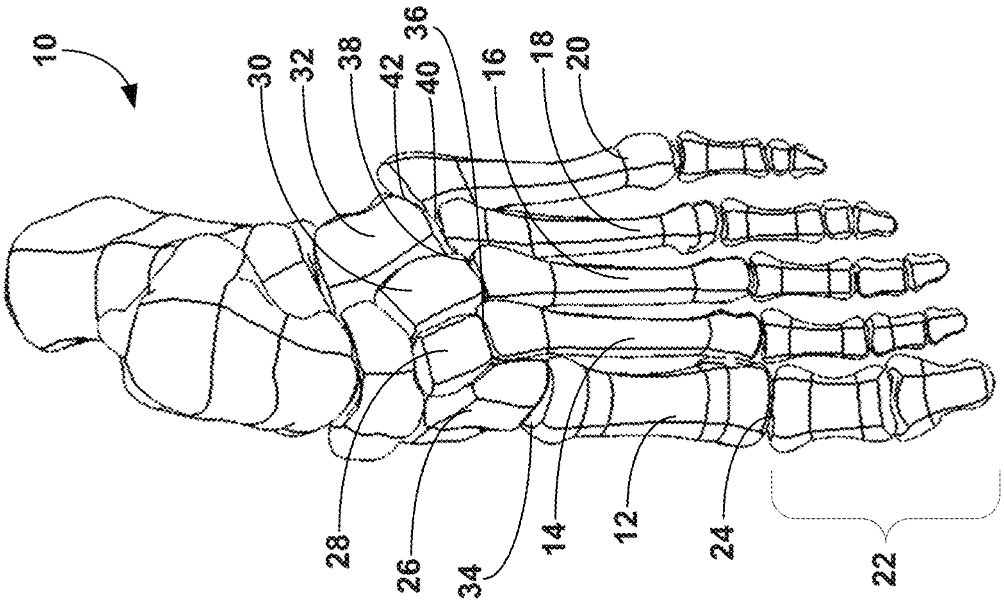

FIGS. 1A and 1B are top and front views, respectively, of a foot 10 showing normal metatarsal alignment positions. Foot 10 is composed of multiple bones including a first metatarsal 12, a second metatarsal 14, a third metatarsal 16, a fourth metatarsal 18, and a fifth metatarsal 20. First metatarsal 12 is on a medial-most side of the foot while fifth metatarsal 20 is on a lateral-most side of the foot. The metatarsals are connected distally to phalanges 22 and, more particularly, each to a respective proximal phalanx. The joint 24 between a metatarsal and a corresponding opposed proximal phalanx is referred to as a metatarsophalangeal ("MTP") joint. The first MTP joint is labeled as joint 24 in FIG. 1A, although second, third, fourth, and fifth MTP joints are also illustrated in series adjacent to the first MTP joint.

The first metatarsal 12 is connected proximally to a medial cuneiform 26, while the second metatarsal 14 is connected proximally to an intermediate cuneiform 28, and the third metatarsal 16 is connected proximally to lateral cuneiform 30. The fourth and fifth metatarsals 18, 20 are connected proximally to the cuboid bone 32. The joint between a metatarsal and opposed bone (cuneiform, cuboid) is referred to as the tarsometatarsal ("TMT") joint. FIG. 1A designates a first TMT joint 34, a second TMT joint 36, a third TMT joint 38, a fourth TMT joint 40, and a fifth TMT joint 42. The angle between adjacent metatarsals is referred to as the intermetatarsal angle ("IMA").

In the example of FIGS. 1A and 1B, foot 10 is illustrates as having generally normally aligned metatarsals. Normal metatarsal alignment may be characterized, among other attributes, by a low intermetatarsal angle (e.g., 9 degrees or less, such as 5 degrees or less) between the first metatarsal and the second metatarsal. In addition, the lesser metatarsals may be generally parallel to a longitudinal axis bisecting the foot proximally to distally.

Figure 3A:
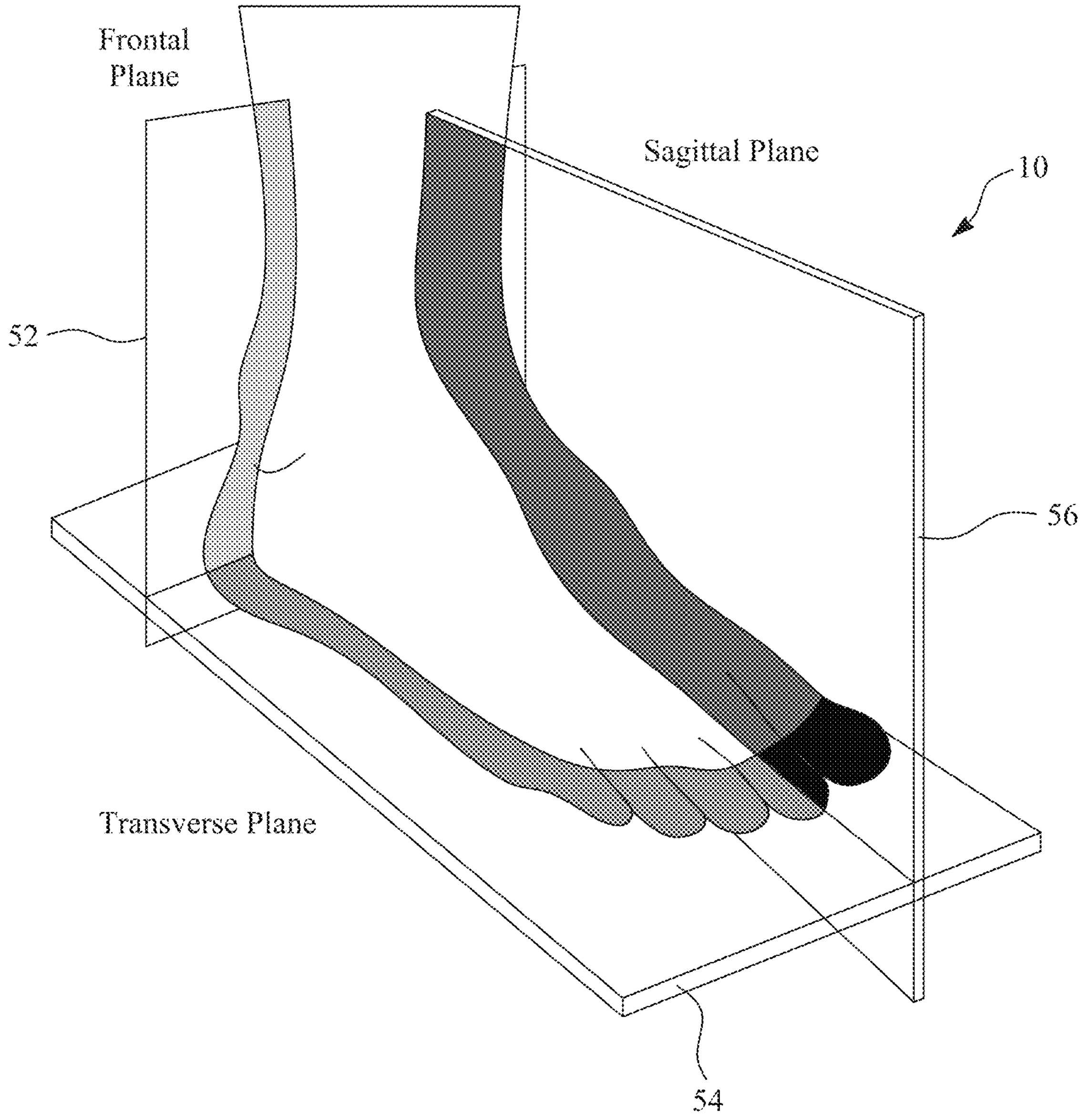
FIG. 3A illustrates the different anatomical planes of a foot.

FIG. 3A illustrates the different anatomical planes of foot 10, including frontal plane 52, transverse plane 54, and sagittal plane 56. The frontal plane 52, which is also known as the coronal plane, is generally considered any vertical plane that divides the body into anterior and posterior sections. On foot 10, the frontal plane 52 is a plane that extends vertically and is perpendicular to an axis extending proximally to distally along the length of the foot. The transverse plane 54, which is also known as the horizontal plane, axial plane, or transaxial plane, is considered any plane that divides the body into superior and inferior parts. On foot 10, the transverse plane 54 is a plane that extends horizontally and is perpendicular to an axis extending dorsally to plantarly (top to bottom) across the foot. Further, the sagittal plane 56 is a plane parallel to the sagittal suture which divides the body into right and left halves. On foot 10, the sagittal plane 56 is a plane that extends vertically and intersects an axis extending proximally to distally along the length of the foot.

Figure 2B:
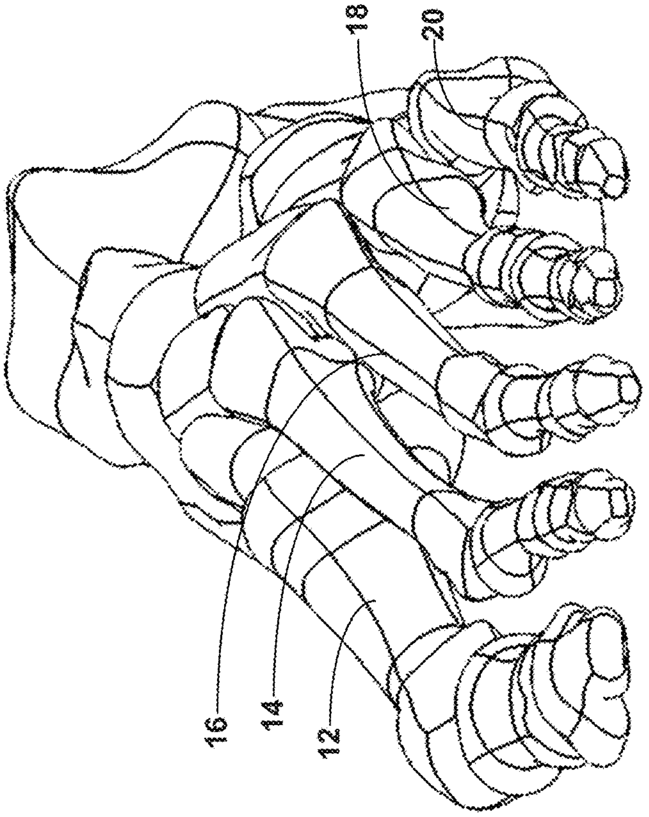
FIGS. 2A and 2B are top and front views, respectively, of a foot showing an example metatarsal adductus bone misalignment.
Figure 2A:
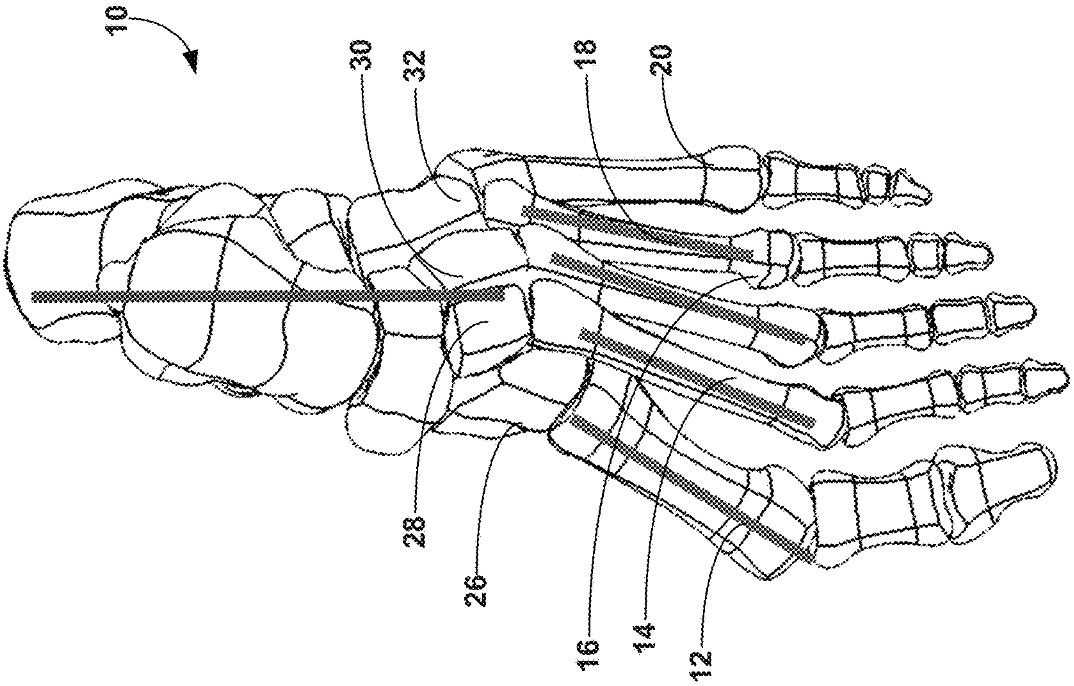
Figure 3B:
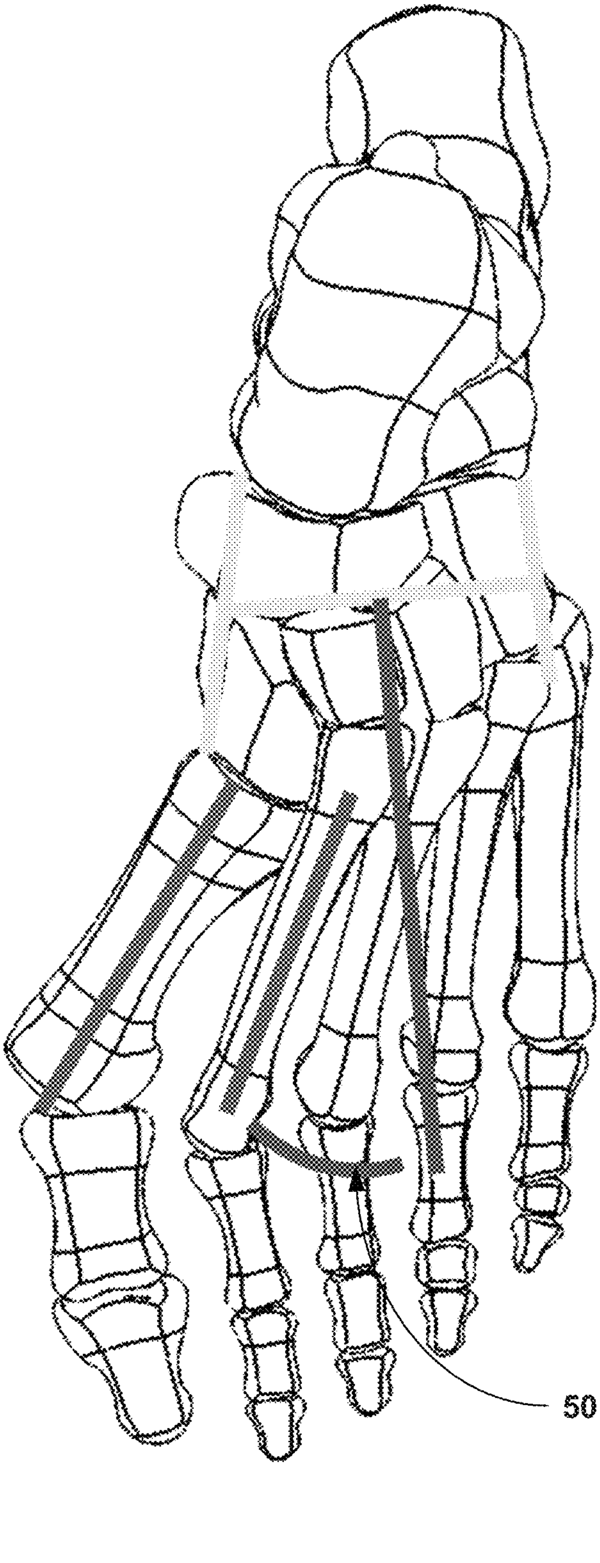
FIG. 3B illustrates the metatarsus adductus of the foot from FIGS. 2A and 2B characterized by a metatarsus adductus angle.

For patients afflicted with metatarsal adductus, at least one or more of the lesser metatarsals (the second through fifth metatarsals) may be deviated medially in the transverse plane (e.g., in addition to or in lieu of being rotated in the frontal plane and/or being deviated in the sagittal plane relative to clinically defined normal anatomical alignment for a standard patient population). FIGS. 2A and 2B are top and front views, respectively, of foot 10 showing an example metatarsal adductus bone misalignment. As shown in this example, the metatarsals are deviated medially relative to an axis bisecting the foot. This can result in an abnormal biomechanical structure benefiting from surgical intervention. FIG. 3B illustrates the metatarsus adductus of foot 10 from FIGS. 2A and 2B being characterized by a metatarsus adductus angle 50.

Figure 4:
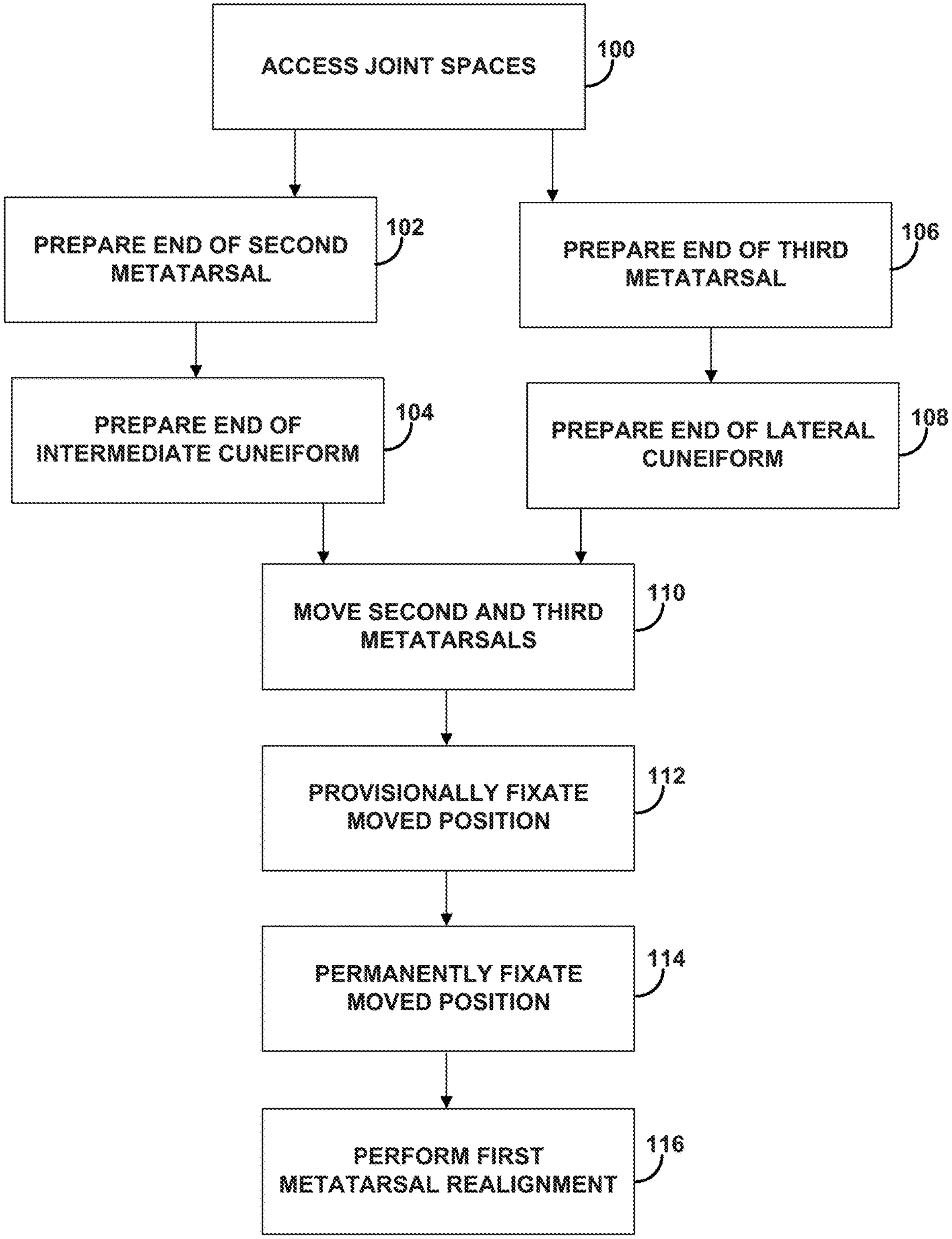
FIG. 4 is a flow diagram illustrating an example technique for preparing TMT joints for fusion and realigning multiple metatarsals to treat a metatarsus adductus deformity.

Bone positioning techniques and instruments can be useful to correct a misalignment of one or more bones, such as a metatarsal adductus and/or hallux valgus metatarsal misalignment, and/or to promote fusion across a joint (e.g., such as an arthritis joint fusion procedure). FIG. 4 is a flow diagram illustrating an example technique for preparing TMT joints for fusion and realigning one or more (e.g., multiple) metatarsals to treat at least a metatarsus adductus deformity. The technique will be described with respect to the bone numbering introduced with respect to FIGS. 1A and 1B, although may be performed on other bones. For purposes of discussion, the technique of FIG. 4 will be discussed with respect to different example images, although may be performed without such instrumentation or with different instrumentation, as discussed herein.

With reference to FIG. 4, the example technique includes surgically accessing at least the second TMT and third TMT joints (100). To surgically access the joints, the clinician may make one or more incisions (e.g., on a dorsal side of the foot) exposing the second and third TMT joints. The clinician may dissect through the skin, subcutaneous tissue, and fascia. The clinician may mobilize the extensor digitorum *brevis* muscle belly from the extensor hallucis *brevis* and retract the muscle. Soft tissue and/or bone overgrowth may be removed to facilitate joint visualization.

In instances where the clinician is also performing a first metatarsal correction, the clinician may also surgically access the first TMT joint. Although the clinician may make a single incision spanning the first, second, and third TMT joints, a dual incision approach can avoid unnecessary cutting and scarring. With the dual incision approach, the clinician may make one incision providing dorsal (e.g., dorsolateral and dorsomedial) access (and/or, in other examples, medial access) to the first TMT joint and a second incision providing dorsal (e.g., dorsolateral and dorsomedial) to the second and third TMT joints, resulting in an intermediate portion of skin between the first and second incisions. When making a dual incision, the surgeon may surgically access the first TMT joint before, after, or concurrent with surgically accessing the second and third TMT joints.

With access to the TMT joint spaces, the technique of FIG. 4 involves preparing the end faces of the bones forming the second TMT joint 36 in the third TMT joint 38. In particular, the clinician can prepare the end of the second metatarsal 14 facing the second TMT joint (102), prepare the end of the third metatarsal 16 facing the third TMT joint (104), prepare the end of the intermediate cuneiform 28 facing the second TMT joint (106), and/or also prepare the end of the lateral cuneiform 30 facing the third TMT joint (108). While FIG. 4 schematically illustrates an example order in which the bones defining the second and third TMT joints can be prepared, it should be appreciated that the surgical technique is not limited to any particular order of preparation. For example, the clinician can prepare one or both cuneiforms before preparing one or more metatarsals, can prepare one or both metatarsals before preparing one or more cuneiforms, can prepare the ends of one metatarsal and one cuneiform defining one TMT joint before preparing the bone ends of the other TMT joint, or perform bone preparation in yet another order.

In general, the clinician can prepare the end of each bone forming a TMT joint so as to promote fusion of the bone ends across the TMT joint following realignment. Bone preparation may involve using a tissue removing instrument, which may also be referred to as a cutting instrument, to apply a force to the end face of the bone so as to create a bleeding bone face to promote subsequent fusion. Example tissue removing instruments that can be used include, but are not limited to, a saw, a rotary bur, a rongeur, a reamer, an osteotome, a curette, and the like. The tissue removing instrument can be applied to the end face of the bone being prepared to remove cartilage and/or bone. For example, the tissue removing instrument may be applied to the end face to remove cartilage (e.g., all cartilage) down to subchondral bone. Additionally or alternatively, the tissue removing instrument may be applied to cut, fenestrate, morselize, and/or otherwise reshape the end face of the bone and/or form a bleeding bone face to promote fusion. In instances where a cutting operation is performed to remove an end portion of a bone, the cutting may be performed freehand, with the aid of a cutting guide having a guide surface positionable over the portion of bone to be cut, and/or with the aid of a bone preparation template. When using a cutting guide, a cutting instrument can be inserted against the guide surface (e.g., between a slot defined between two guide surfaces) to guide the cutting instrument for bone removal.

In some examples, the clinician cuts at least one bone defining the second TMT joint (e.g., one or both of second metatarsal 14 and intermediate cuneiform 28) and also cuts at least one bone defining the third TMT joint (e.g., one or both of third metatarsal 16 and the lateral cuneiform 30). The clinician may cut both bones defining the second TMT joint or may cut only one bone defining the joint and perform a different preparation technique on the other bone. Similarly, the clinician may cut both bones defining the third TMT joint or may cut only one bone defining the joint and perform a different preparation technique on the other bone.

Where the clinician cuts at least one bone forming a TMT joint, each such cut may be parallel or non-parallel to the end of the bone being cut in one or more of the frontal, transverse, and sagittal planes. For example, the cut may be angled in the transverse plane relative to the end face of the bone and parallel to the end face of the bone in the frontal plane. As other examples, the cut may be curved, arced, spherical, zig-zag, or may define other desired cut shape to facilitate realignment and fusion of one bone relative to another bone portion. In some examples, the end faces of the two bones defining the TMT joint are each prepared by cutting an end portion of each bone to create a shaped opening between the end faces. The opening may have a shape that allows the bones to be repositioned relative to each other (e.g., partially or fully closing the opening created in the process of realignment) to facilitate realignment and subsequent fusion.

Figure 5A:
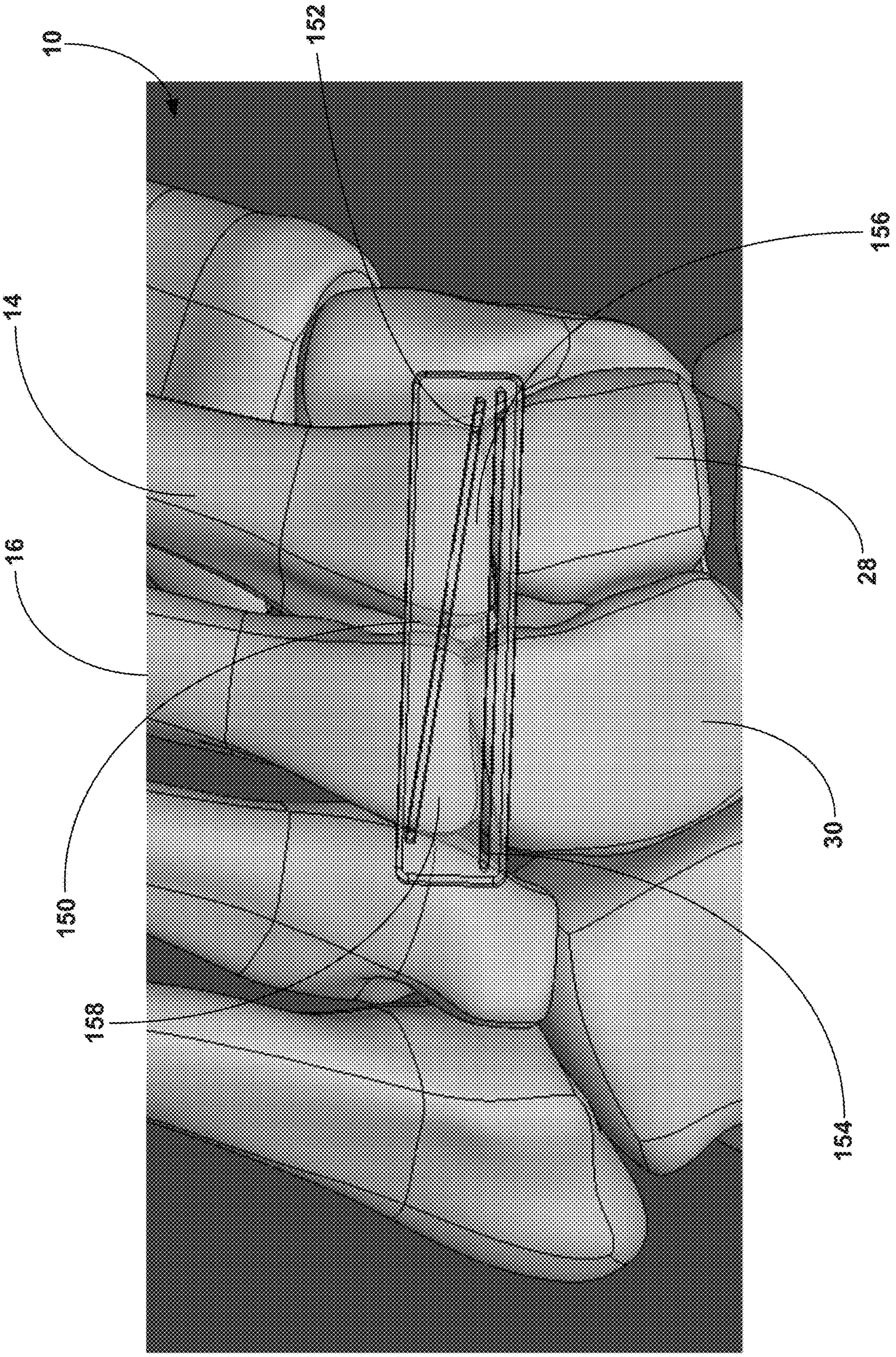
FIG. 5A is a top view of a foot showing an example cut guide positioned over the second and third TMT joints to illustrate example bone wedges that may be cut during joint preparation.

FIG. 5A is a top view of foot 10 showing an example cut guide 150 positioned over the second and third TMT joints to illustrate example bone wedges that may be cut during joint preparation. In this example, cut guide 150 is shown defining a first guide surface 152 (which is illustrated as a cutting slot) positioned over a portion of a second metatarsal 14 and a portion of a third metatarsal 16 to be cut. Cut guide 150 is also shown as defining a second guide surface 154 (which is illustrated as a cutting slot) positioned over a portion of an intermediate cuneiform 28 and a lateral cuneiform 30 to be cut. The clinician can advance a cutting instrument parallel to first guide surface 152 to cut an end of second metatarsal 14 and also to cut an end of third metatarsal 16. The clinician can also advance the cutting instrument parallel to second guide surface 154 to cut an end of intermediate cuneiform 28 and lateral cuneiform 30. In different implementations, a guide surface of cut guide 150 may be linear, curved, and/or define yet other shapes. According, the step of guiding a cutting instrument parallel to the guide surface may result in a linear cut, a curved cut, or yet other shaped cut across the bone.

In the example of FIG. 5A, first guide surface 152 is illustrated as being angled in the transverse plane across the second and third metatarsals 14, 16. The first guide surface 152 is illustrated as being angled from a medial-proximal side of second metatarsal 14 toward a lateral-distal side of third metatarsal 16. The lateral-distal side of third metatarsal 16 may still be on the proximal half of the metatarsal, albeit comparatively distal to the proximal location on the second metatarsal. By preforming an angled cut relative to the end faces of the bones being cut, a wedge-shaped bone portion may be released from the bone. In FIG. 5A, a wedge-shaped section 156 of second metatarsal 14 is released upon cutting the second metatarsal. Further, a wedge-shaped section 158 of third metatarsal 16 is released upon cutting the third metatarsal. Each wedge-shaped section of bone removed via cutting may have a narrow width (e.g., apex) on a medial side of the bone being cut and a wider width (e.g., base) on a lateral side of the bone being cut. The degree of angulation in the specific dimensions of the bone wedge formed during cutting may vary depending on the anatomy of the patient and the extent of the deformity being corrected. In either case, the bone wedges so cut can be removed from the TMT joint spaces to define a wedge-shaped opening relative to an opposed bone.

In the example of FIG. 5A, the clinician can use second guide surface 154 to guide the cutting instrument to cut an end of intermediate cuneiform 28 and lateral cuneiform 30 to promote fusion following realignment of the metatarsals. The cuts performed on the intermediate cuneiform 28 and lateral cuneiform 30 may be generally parallel to the end face of a bone being cut (e.g., in the transverse plane) or may be angled relative to an end face of the bone being cut. In still other examples, the end faces of one or both of intermediate cuneiform 28 and lateral cuneiform 30 may not be cut but may be prepared using a different technique as discussed above (e.g., fenestrated).

In some examples in which the second metatarsal 14 and the third metatarsal 16 are prepared by cutting, the metatarsals may be cut using a single continuous cut across both metatarsals. For example, the clinician may guide a cutting instrument linearly from a medial side of the second metatarsal 14 toward the lateral side of the third metatarsal 16 or from the lateral side of the third metatarsal to the medial side of the second metatarsal. In either case, the clinician may form a continuous cut line transecting the ends of the second and third metatarsals. Such a continuous cut across the bases of the second and third metatarsals may be useful to promote reliable reduction of the metatarsus adductus angle during subsequent bone realignment. In applications where the intermediate cuneiform 28 and the lateral cuneiform 30 are cut in addition to or in lieu of the ends of the metatarsals, the two cuneiforms may or may not be cut using such a continuous cut across the ends of the two metatarsals.

In other applications of the surgical technique, the ends of the second metatarsal 14 and third metatarsal 16 may be cut independently (e.g., without moving the cutting instrument in a continuous cutting line across the two metatarsals). For example, when the patient exhibits a significant step off (e.g., distal offset) between the end of the intermediate cuneiform 28 and the end of the lateral cuneiform 30, the ends of the opposed second and third metatarsals 14, 16 may be prepared independently (e.g., through two separate cuts) in lieu of forming a continuous cut across the ends of the two metatarsals. The ends of the opposed second and third metatarsals 14, 16 may be prepared independently for other reasons as well, such as to provide independent control/adjustability over the cut angles on the second and third metatarsals.

In instances where the clinician cuts the end face of the bone, the clinician may or may not perform one or more additional preparation steps on the end face prior to or after cutting the end face. In some examples, the clinician fenestrates the newly-formed end face of the bone after cutting the bone. The clinician may use a drill to fenestrate the end newly-formed end face of the bone being cut, which can help promote subsequent fusion of the bone following realignment. The clinician may fenestrate a bone face by making multiple openings (e.g., drill holes) in the bone face, providing multiple bleeding points in the end of the bone face. Each drill hole may be comparatively small relative to the cross-sectional area of the end face, such as less than 10% of the cross-sectional area of the end face, less than 5% of the cross-sectional area of the end face, or less than 1% of the cross-sectional area of the end face. The multiple openings can be arrayed at different locations across the end face to provide locations for promoting fusion across the end face. The number of holes formed during fenestration may vary and, in some examples, is greater than 5, such as greater than 10.

Figure 5B:
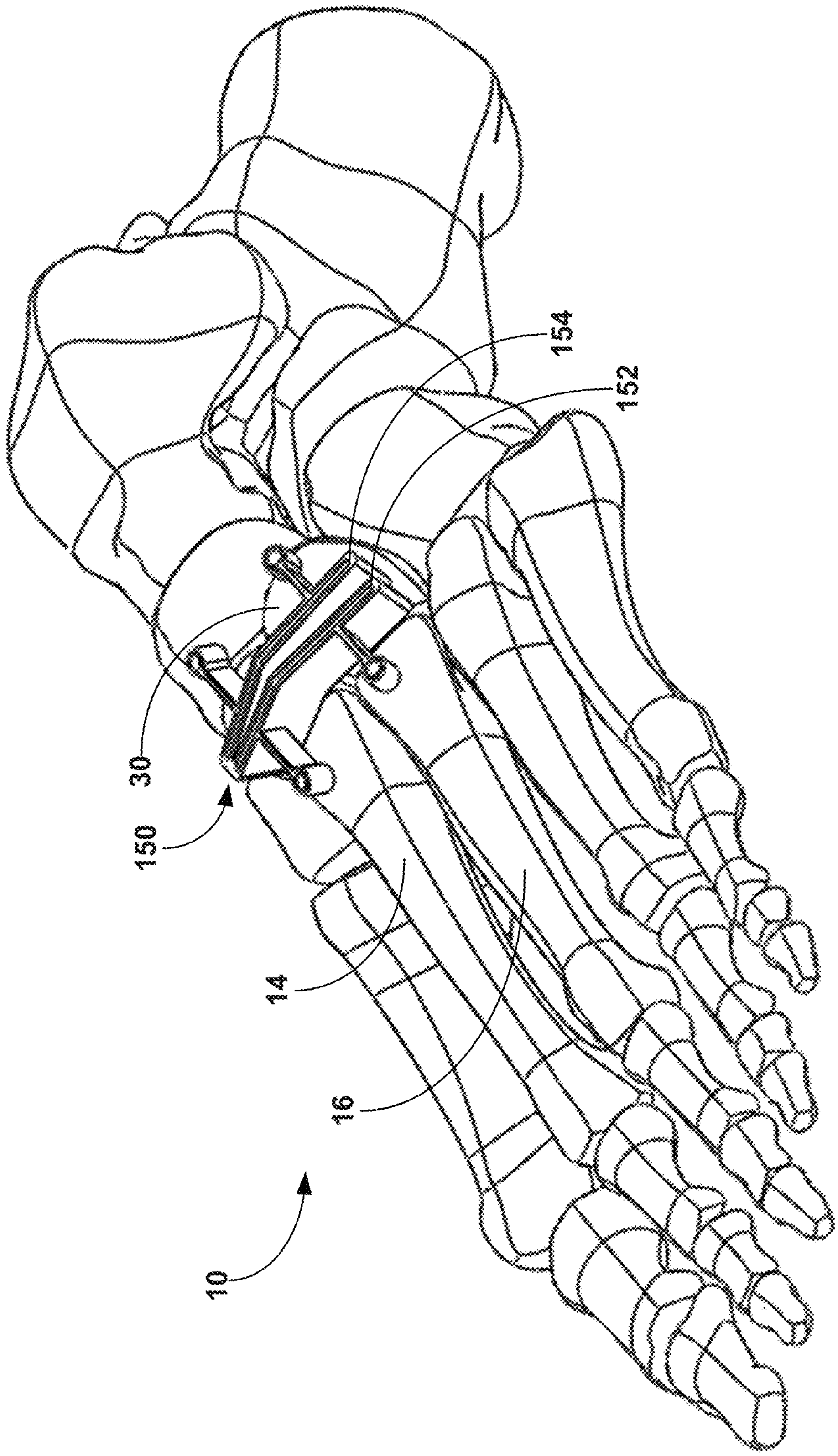
FIGS. 5B-5E illustrate example bone preparation steps that may be performed on a foot using an example cutting guide.
Figure 5C:
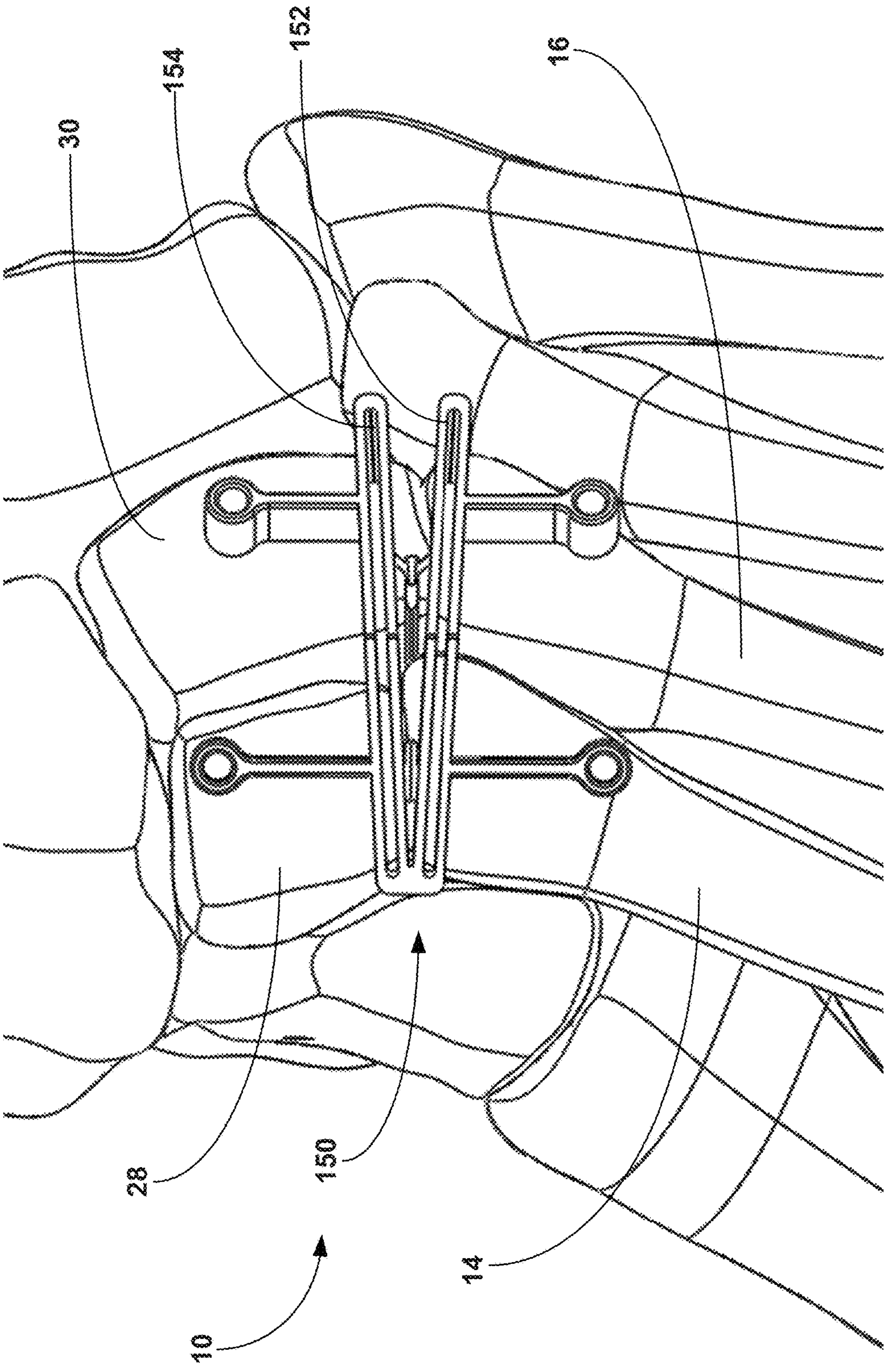

FIGS. 5B-5E illustrate example bone preparation steps that may be performed on foot 10 using an example configuration of cutting guide 150 according to a technique of the disclosure. In particular, FIGS. 5B and 5C are perspective and top (dorsal) view illustrations of foot 10 showing cut guide 150 positioned over a dorsal side of the foot. Specifically, cut guide 150 is shown with first guide surface 152 positioned over a portion of second metatarsal 14 and a portion of third metatarsal 16 to be cut, and second guide surface 154 is positioned over a portion of intermediate cuneiform 28 and lateral cuneiform 30 to be cut. In this example, cut guide 150 defines at least one fixation aperture positionable over each of second metatarsal 14, third metatarsal 16, intermediate cuneiform 28, and lateral cuneiform 30. A clinician can insert fixation pins through one or more (e.g., all) of the fixation apertures to secure the cut guide to underlying bone.

Figure 5D:
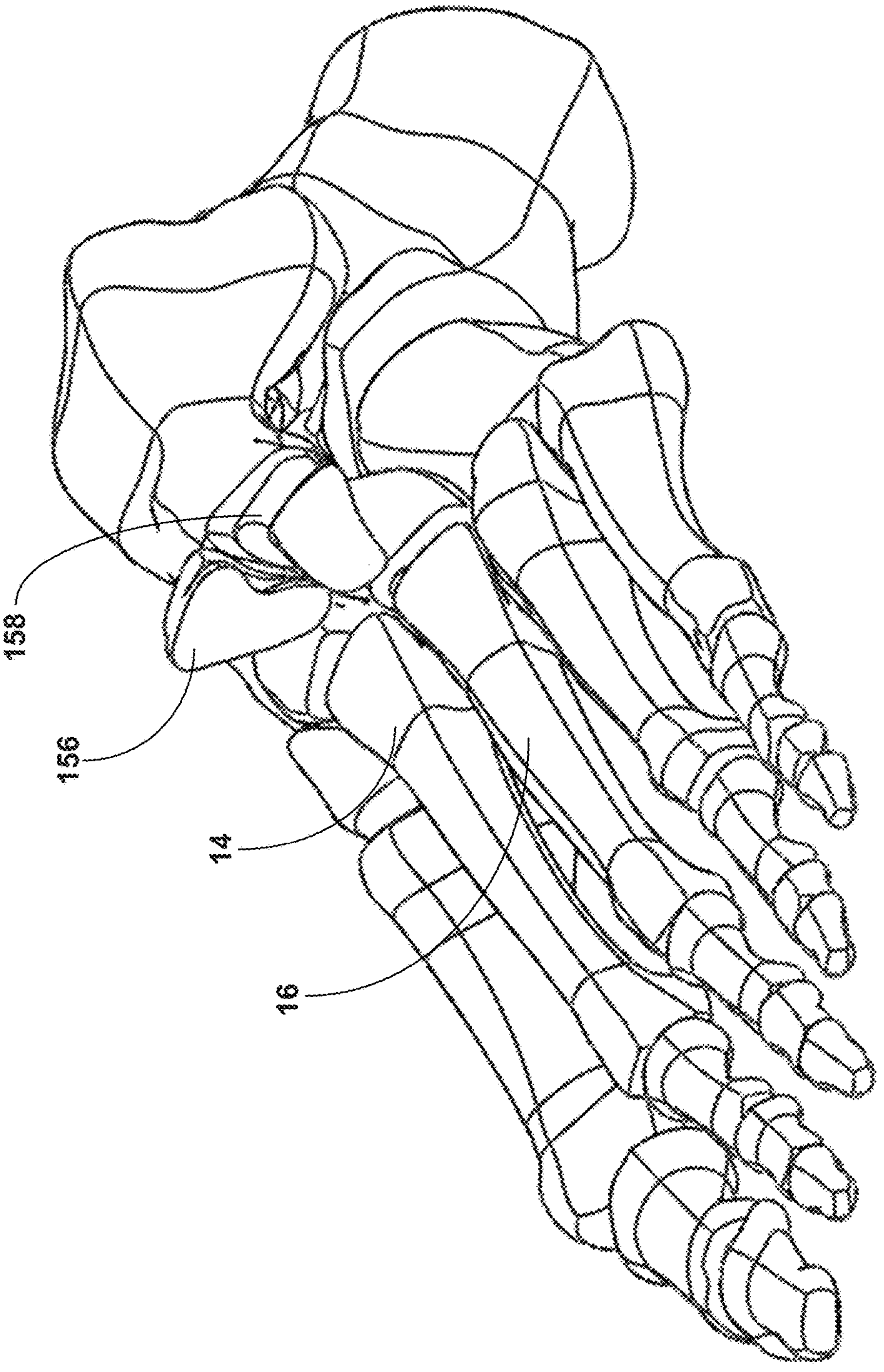
Figure 5E:
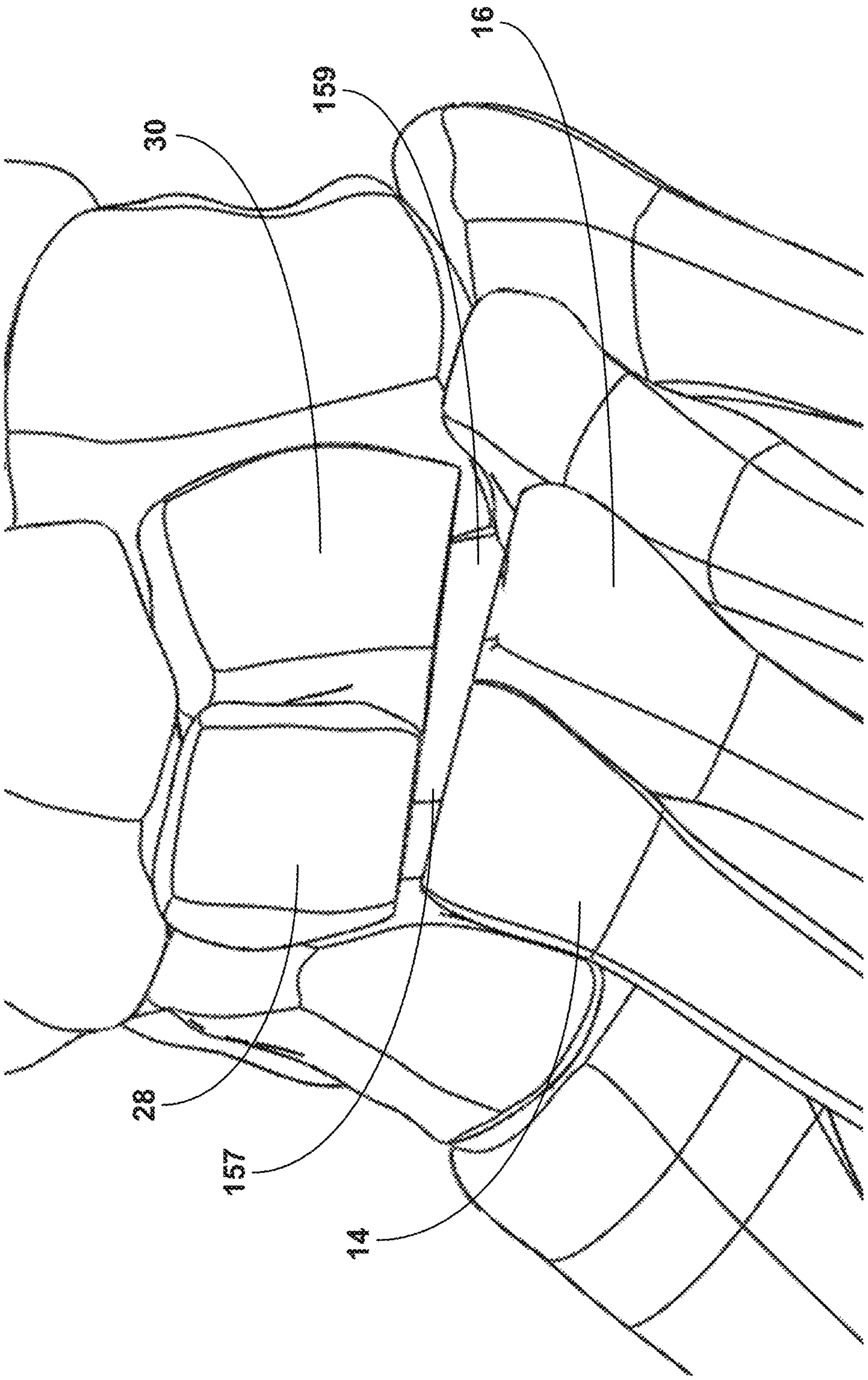

In use, the clinician can guide a cutting instrument along first guide surface 152 to cut an end of second metatarsal 14 and also to cut an end of third metatarsal 16. The clinician can also guide the cutting instrument along second guide surface 154 to cut an end of intermediate cuneiform 28 and lateral cuneiform 30. FIG. 5D is a perspective view of the foot showing example bone portions that can be removed after cutting, specifically illustrating an example wedge-shaped section 156 removed from second metatarsal 14 and an example wedge-shaped section 158 removed from third metatarsal 16. Additional bone sections may be removed from intermediate cuneiform 28 and lateral cuneiform 30. FIG. 5E illustrates an example opening 157 formed between second metatarsal 14 and intermediate cuneiform 28 upon removal of one or more bone portions and an example opening 159 formed between third metatarsal 16 and lateral cuneiform 30 upon removal of one or more bone portions.

With further reference to FIG. 4, the example technique involves moving the second metatarsal 14 and the third metatarsal 16 in at least one plane (110). While FIG. 4 schematically illustrates an example order in which the second and third metatarsals 14, 16 are moved after preparing the end faces of metatarsals 14, 16 and opposed intermediate and lateral cuneiforms 28, 30, other orders of bone preparation and movement may be performed. For example, the clinician can move the second and/or third metatarsals 14, 16 before preparing one or more metatarsals and/or one or more cuneiforms (e.g., before preparing the end faces of all of the bones). For instance, the clinician may move the second and third metatarsals 14, 16 and then prepare the end faces of metatarsals 14, 16 and opposed intermediate and lateral cuneiforms 28, 30. In these implementations, the clinician may or may not further move the second and/or third metatarsals 14, 16 after preparing the end faces of the metatarsals and cuneiforms. As another example, the clinician may prepare the end face of one or more bones (e.g., one or more metatarsals and/or cuneiforms), move one or both of second metatarsal 14 and third metatarsal 16, and then prepare the end face of one or more other bones (e.g., one or more metatarsals and/or cuneiforms).

Independent of the order of movement and bone preparation, the clinician may move the second and third metatarsals 14, 16 in one or more planes, such as the transverse plane, e.g., by pivoting the metatarsals about their proximal ends, causing a distal end of the metatarsals to move laterally in the transverse plane. In instances where a wedge-shaped opening was formed at the second and/or third TMT joints during bone preparation, lateral rotation of the distal ends of the second and third metatarsals may close the wedge-shaped opening(s) (or close another shaped opening, in instances in which a non-wedge-shaped opening was created). For example, translation of the distal ends of the second and third metatarsals 14, 16 laterally in the transverse plane may bring the ends of the second metatarsal 14 and opposed intermediate cuneiform 28 as well as the ends of the third metatarsal 16 and opposed lateral cuneiform 30 in generally parallel alignment. The clinician may move the second and/or third metatarsal in the frontal plane and/or sagittal plane in addition to or in lieu of moving one or both bones in the transverse plane. For example, the clinician may rotate one or both bones in the frontal plane and/or translate one or both bones (e.g., dorsally) in the sagittal plane.

In general, movement of second metatarsal 14 and third metatarsal 16 in the transverse plane can close the metatarsus adductus angle. The metatarsus adductus angle may be the angular measurement formed between the line bisecting the second metatarsal and the longitudinal line bisecting the lesser tarsus on a dorsoplantar radiograph. In some examples, the second and third metatarsals 14, 16 are moved until the metatarsus adductus angle for each metatarsal is 15° or less, such as 12° or less, 10° or less, 7° or less, 5° or less, or 3° or less.

The second metatarsal 14 and third metatarsal 16 may be moved individually or jointly (e.g., as a bone block). Moving the second and third metatarsals 14, 16 as a joined group may be helpful to achieve a more natural realignment of the metatarsals and correction of the metatarsus adductus deformity. To help move the second and third metatarsals 14, 16 as a joined group, the ligaments between the two metatarsals may be preserved during preparation of the second and third TMT joints. For example, the plantar TMT ligaments and ligaments between the second and third metatarsals 14, 16 may be preserved (e.g., remain uncut or unbroken) during preparation and movement of the second and third metatarsals. Preserving the ligament structure can help avoid destabilization of the second and third TMT joints during deformity reduction, which may improve the anatomical realignment of the bone structure.

To move the second and third metatarsals 14, 16, either alone or in combination, the bones may be pivoted about their proximal base, causing the distal ends of the bones to translate laterally in the transverse plane. When moving the second and third metatarsals 14, 16 as a group, the clinician may pivot the second and third metatarsal bone block about the proximal medial portion of second metatarsal 14. The clinician may move the second and third metatarsals 14, 16 as a combined group in the transverse plane, with or without simultaneously rotating both bones in the frontal plane and/or adjusting the sagittal plane position of the bones. In some implementations, the clinician moves the second and third metatarsals 14, 16 as a group about the Lisfranc ligament while the second metatarsal remains attached to the Lisfranc ligament. Accordingly, the Lisfranc ligament may act as a hinge or pivot point about which the second and third metatarsal bone group can rotate in the transverse plane.

In other examples, the clinician may substantially independently move the second and third metatarsals 14, 16 (e.g., by applying a separate movement force to each metatarsal). For example, the clinician may apply a force to move third metatarsal 16 in one or more planes and subsequently apply a force to move the second metatarsal 14 in one or more planes (or, instead, move the second metatarsal 14 followed by the third metatarsal), such as in two or more, or all three planes. The clinician may or may not cut or otherwise release one or more ligamentous attachments interconnecting the second and third metatarsals 14, 16 to help facilitate independent repositioning of the two bones.

Independent of whether the clinician moves the second and third metatarsals 14, 16 together or independently, the intermetatarsal angle between second and third metatarsals may or may not change during metatarsus adductus correction. In other words, the intermetatarsal angle between second metatarsal 14 and third metatarsal 16 may or may not compress from a pre-corrected intermetatarsal angle to the intermetatarsal angle exhibited after correction. In some implementations, the second and third metatarsals 14, 16 are pivoted as a group within the transverse plane without substantially changing the intermetatarsal angle between the second and third metatarsals. For example, the intermetatarsal angle between the second and third metatarsals may change (e.g., reduce) less than 5°, such as less than 2°, or less than 1° from the angle exhibited before metatarsus adductus correction to the angle exhibited after the correction technique is performed.

To help facilitate movement of the second and third metatarsals in the transverse plane, the clinician may perform a soft tissue release between third metatarsal 16 and fourth metatarsal 18. The soft tissue release may mobilize the third metatarsal relative to the adjacent fourth metatarsal, allowing the joined second-third metatarsal bone block to be pivoted in the transverse plane.

In addition to moving the second metatarsal and the third metatarsal in the transverse plane, the clinician can also move fourth metatarsal 18 and fifth metatarsal 20 in one or more planes (e.g., one or more of the transverse plane, the frontal plane, and the sagittal plane), e.g., to close the metatarsus adductus angle exhibited by those lesser metatarsals. In practice, movement of second metatarsal 14 and third metatarsal 16 in one or more planes (e.g., the transverse plane) may cause the fourth and fifth metatarsals to naturally correct in same one or more planes (e.g., the transverse plane) without requiring separate surgical intervention on the fourth and fifth metatarsals 18, 20. For example, as the clinician rotates the distal end of second metatarsal 14 and third metatarsal 16, either alone or in combination, the distal ends of fourth metatarsal 18 and fifth metatarsal 20 may also move laterally. The proximal base of fourth metatarsal 18 and the proximal base of fifth metatarsal 20 may reorient relative to the cuboid bone 32, closing the metatarsus adductus angle of the fourth and fifth metatarsals. Without wishing to be bound by any particular theory, it is believed that force applied to the second and/or third metatarsal during movement may translate through the tissue and ligament structure interconnecting such metatarsal(s) to the fourth and fifth metatarsals, pulling the lesser metatarsals into realignment.

The position of fourth metatarsal 18 and fifth metatarsal 20 may correct without surgically accessing and preparing the metatarsal (in response to correction of second metatarsal 14 and/or third metatarsal 16). In other applications, however, the clinician may surgically access and prepare the bones defining fourth TMT joint 40 and/or fifth TMT joint 42 in addition to or in lieu of preparing one or more other TMT joints. For example, before or after moving the fourth metatarsal 18 and/or fifth metatarsal 20 in one or more planes (e.g., separate from or in combination with movement of the second metatarsal 14 and/or third metatarsal 16), the clinician can surgically access and prepare the bones defining fourth TMT joint 40 and/or fifth TMT joint 42. The clinician may decide whether to access and prepare the bones defining fourth TMT joint 40 and/or fifth TMT joint 42 depending, for example, on the nature of the deformity being corrected and the perceived need prepare the joints for bone realignment and/or fusion With typical metatarsus adductus deformities, the metatarsals may exhibit a substantially uniplanar misalignment in the transverse plane (although may be misaligned in the frontal plane and/or sagittal plane). For this reason, the example technique of FIG. 4 has generally been described as correcting the second and third metatarsals 14, 16 (and, optionally, fourth and fifth metatarsals 18, 20) in the transverse plane. The clinician may move the metatarsals in only the transverse plane to correct the generally uniplanar misalignment. Alternatively, the clinician may move one or more of the metatarsals being realigned (e.g., multiple or all of the metatarsals been realigned) in more than one plane. For example, in addition to or in lieu of realigning the metatarsal(s) in the transverse plane, the clinician may adjust the rotational angle of the metatarsal(s) in the frontal plane and/or adjust the angle of the metatarsal(s) in the sagittal plane.

Where the clinician performs a multi-planar realignment, the clinician may move one or more metatarsals in multiple planes simultaneously through a single movement, e.g., by moving the metatarsal in an arc or other movement pathway to adjust the position of the metatarsal in multiple planes. The clinician may optionally perform further fine adjustment of the moved position of the one or more metatarsals, e.g., with the aid of a bone positioning device and/or by grasping the metatarsal by hand (e.g., with the aid of a pin inserted into the metatarsal) to finalize the position of the metatarsal prior to fixation.

In other examples, the clinician may perform different movement steps to move the one or more metatarsals in different planes. For example, the clinician may initially move the one or more metatarsals in one or two planes (e.g., transverse plane, frontal plane, sagittal plane) then move the one or more metatarsals in one or two other planes (e.g., the other of the transverse plane, frontal plane, sagittal plane), optionally followed by movement of the one or more metatarsals in a third plane. In other words, the clinician may perform different actions to move the one or more metatarsals in different planes. Each movement step may be performed with the aid of a bone positioning device (which may be the same or different device for different movement steps) and/or by grasping the metatarsal by hand (e.g., with the aid of a pin inserted into the metatarsal).

In some examples, the clinician may move one or more of the metatarsals being realigned (e.g., second metatarsal 14 and/or third metatarsal 16) proximally in the transverse plane toward the opposed bone in addition to or in lieu of moving the metatarsal(s) laterally. For example, the clinician may simultaneously move the metatarsal being realigned (e.g., second metatarsal 14 and/or third metatarsal 16) laterally and proximally in an arc (e.g., parabola) to establish a moved position of one or both metatarsals. As another example, the clinician may move one or more of the metatarsals being realigned (e.g., second metatarsal 14 and/or third metatarsal 16) proximally in the transverse plane toward the opposed bone without moving the one or more of the metatarsals in any other planes. For example, during an arthritic joint fusion procedure, the clinician may prepare the end face of a metatarsal and opposed cuneiform and move the prepared end face of the metatarsal proximally against the prepared end face of the opposed cuneiform (e.g., during a compression step) without otherwise realigning the metatarsal.

The clinician can move the one or more metatarsals being realigned (e.g., second metatarsal 14 and/or third metatarsal 16) by hand and/or with the aid of one or more instruments. For example, the clinician can grasp the second and/or third metatarsal and advance the distal end of the metatarsal laterally to reduce the metatarsus adductus angle. The clinician may insert one or more pins into the metatarsal being moved (e.g., second and/or third metatarsal) to provide a joystick or structure that can be grasped to manipulate movement of the bones. Additionally or alternatively, the clinician may utilize a tenaculum or tong to grasp one or both of the second and third metatarsals to facilitate realignment.

In some examples, the clinician may use a bone positioning guide (also referred to as a bone positioning device) to help apply a force to a metatarsal (e.g., second metatarsal 14 and/or third metatarsal 16) to facilitate realignment. The bone positioning guide may include one end that engages with (e.g., contacts, with or without being provisionally fixated to) the metatarsal to which the force is being applied and another end that engages with (e.g., contacts, with or without being provisionally fixated to) a different bone.

Embodiments of any instrument described herein (e.g., cutting guide, bone preparation template, bone positioning device) may include or be fabricated from any suitable materials (e.g., metal, plastic). In certain embodiments, an instrument is fabricated at least partially from a radiolucent material such that it is relatively penetrable by X-rays and other forms of radiation, such as thermoplastics and carbon-fiber materials. Such materials are useful for not obstructing visualization of bones using an imaging device when the instrument is positioned on bones.

One type of bone positioning guide that may be used to move a metatarsal in one or more planes, such as used to move second metatarsal 14 and third metatarsal 16, is a compressor instrument. For example, when an opening (e.g., wedge-shaped opening) is created at the second and third TMT joints during preparation of the bone ends, a compressor may be attached to the second and/or third metatarsal and another bone, such as the intermediate cuneiform and/or lateral cuneiform, respectively. The compressor may apply a distal-to-proximal force across the second and/or third TMT joints, causing the opening created across the joint to close. When the opening is wedge-shaped, causing the wedge-shaped opening to close can cause the distal end of second metatarsal 14 and/or third metatarsal 16 to pivot in the transverse plane. When used, the compressor may additionally or alternatively be used to compress the ends of the bone faces together, e.g., by compressing intermediate cuneiform 28 and second metatarsal 14 together and/or compressing lateral cuneiform 30 and third metatarsal 16 together, to facilitate subsequent fixation and fusion.

A variety of different compressor designs can be used to move one or more bones according to disclosure. In general, a compression instrument can provide compression functionality (e.g., moving bones towards each other) when actuated in one direction and distraction functionality (e.g., moving bones away from each other) when actuated in the opposite direction. For this reason, a compressor may also be referred to as a compressor-distractor. While compressor-distractor devices having a variety of configurations can be used to perform the techniques of the disclosure, in some examples, a compressor-distractor is configured relative to the anatomical profile of the foot to facilitate compression and/or distraction of one or more lesser metatarsals/TMT joints while positioning the compressor-distractor at a location that is unobtrusive to the incision site(s) where the clinician is working.

Figure 6A:
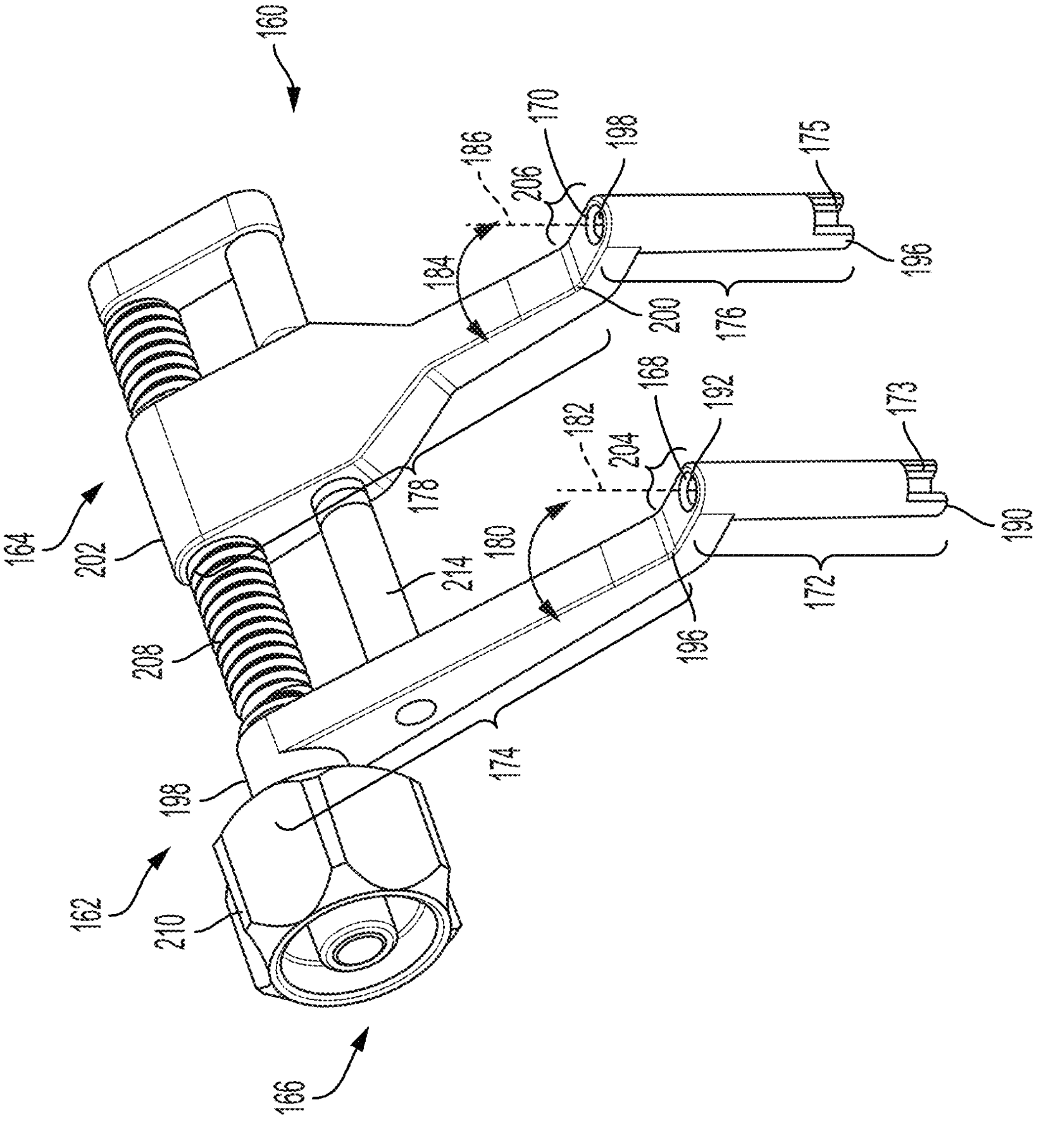
FIG. 6A is a perspective view of an example compressor-distractor that can be used in systems and techniques according to disclosure.

FIG. 6A is a perspective view of an example compressor-distractor 160 that can be used in systems and techniques according to disclosure. Compressor-distractor 160 is illustrated as having a first engagement arm 162 and a second engagement arm 164. Compressor-distractor 160 also includes an actuator 166 that is operably coupled to the first engagement arm 162 and the second engagement arm 164. Actuator 166 can be actuated to move the two engagement arms toward each other and away from each other to adjust a separation distance between the two arms. Further, as will be discussed in greater detail, each engagement arm may include a straight portion and an angled portion to offset actuator 166 relative to pin-receiving holes that each receive a pin inserted into a bone.

First engagement arm 162 may include a first pin-receiving hole 168 and second engagement arm 164 may include a second pin-receiving hole 170. The first pin-receiving hole 168 can receive a first pin, while the second pin-receiving hole 170 can receive a second pin. The first pin and the second pin can be inserted into different bones or bone portions being worked upon. For example, the first pin can be inserted through first pin-receiving hole 168 and into an underlying first bone portion, such as a bone on a proximal side of a TMT joint (e.g., a cuneiform or cuboid). In some implementations, the first bone is on the proximal side of a TMT joint of a lesser metatarsal and is one or more of intermediate cuneiform 28, lateral cuneiform 30, and cuboid 32. The second pin can be inserted through second pin-receiving hole 170 and into an underlying second bone portion, such as a bone on a distal side of a TMT joint (e.g., a metatarsal). In some implementations, the bone is on the distal side of a TMT joint of a lesser metatarsal and is one or more of second metatarsal 14, third metatarsal 16, fourth metatarsal 18, and fifth metatarsal 20. The pin-receiving holes can anchor compressor-distractor 160 to the bones being compressed and/or distracted via the pins inserted through the holes and into the underlying bones.

In FIG. 6A, first engagement arm 162 is illustrated as including a first straight portion 172 and a first angled portion 174. In addition, second engagement arm 164 is illustrated as including a second straight portion 176 and a second angled portion 178. First angled portion 174 extends at a first acute angle 180 relative to a longitudinal axis 182 defined by the first pin-receiving hole 168. Second angled portion 178 extends at a second acute angle 184 relative to a longitudinal axis 186. First and second angled portions 174, 178 may be straight or linear segments of the first and second engagement arms, respectively, but are referred to as angled portions because the portions extend at an angle relative to the straight portions. In certain implementations, regions of compressor-distractor 160 described as being straight or angled may have an extent of curvature or other region of nonlinearity while still performing the functions attributed to a straight portion and/or an angled portion as described herein. For example, first and/or second angled portions define a radius of curvature and/or the angular intersection between an angled portion and a straight portion may not be defined by a sharply defined angle but instead can be defined by a radius of curvature resulting in the angular offset.

The different portions forming first engagement arm 162 and second engagement arm 164 may be configured (e.g., size and/or shaped) relative to the anatomy of the foot over which compressor-distractor 160 is intended to be positioned. For example, as will be discussed with respect to FIG. 6C, first engagement arm 162 and second engagement arm 164 may be configured to position pins received by the pin-receiving holes of compressor-distractor 160 offset from a vertical axis (e.g., sagittal plane) of the foot and/or to position actuator 166 over a lateral side of foot 10. This configuration can be useful, for instance, to position compressor-distractor 160 and/or pins extending therethrough offset from the surgical site (e.g., one or more incisions) where bones are exposed and the clinician is performing the surgical procedure (e.g., bone preparation, fixation).

Figure 6B:
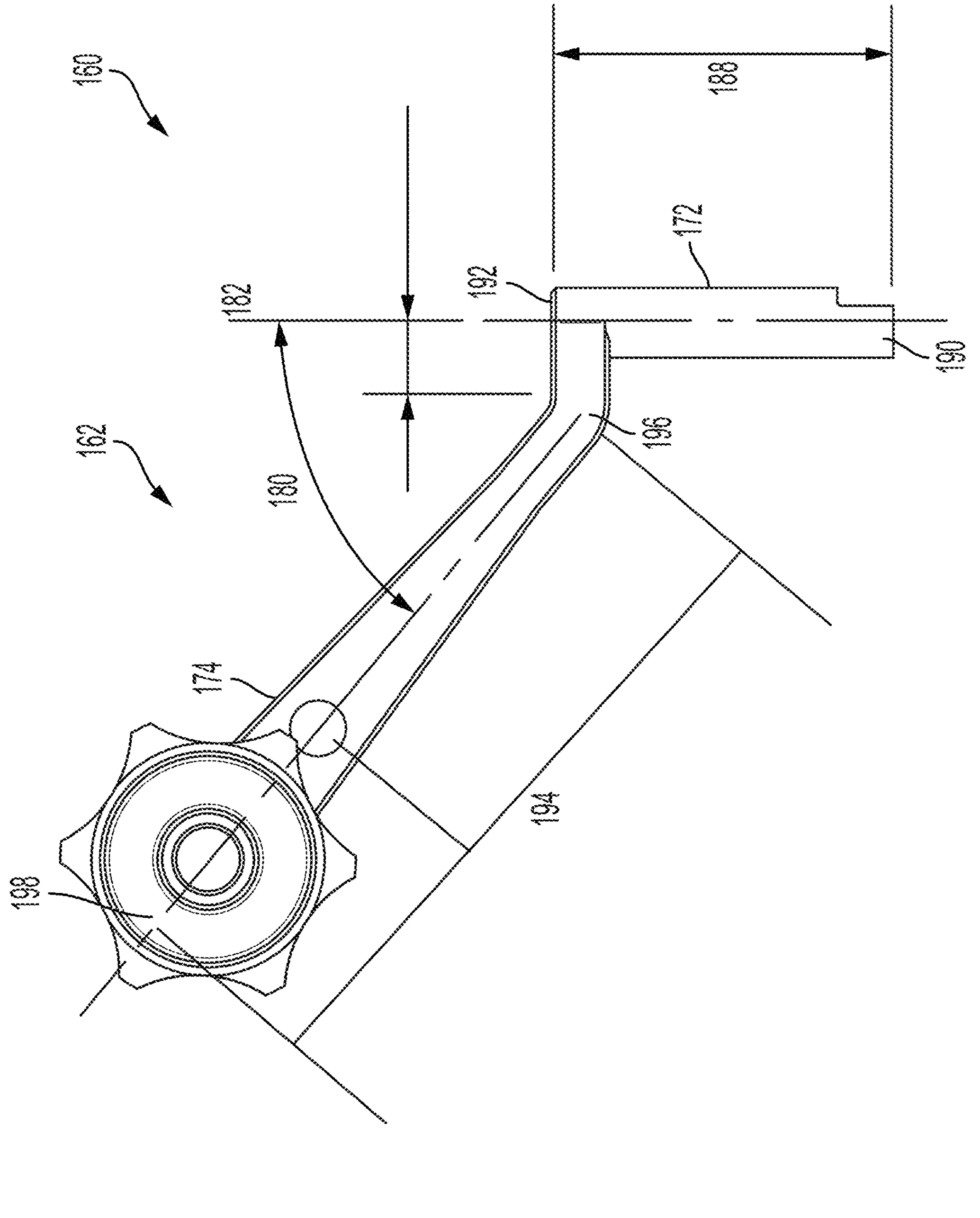
FIG. 6B is a side view of the compressor-distractor from FIG. 6A.

FIG. 6B is a side view of compressor-distractor 160 from FIG. 6A. As illustrated, first straight portion 172 of first engagement arm 162 can define a length 188 extending from a first end 190 to a second end 192. First angled portion 174 of first engagement arm 162 can define a length 194 extending from a first end 196 to a second end 198. The length 188 and the length 194 of first straight portion 172 and first angled portion 174, respectively, may be controlled to control the location and positioning of compressor-distractor 160 once pinned to underlying bones.

While the specific dimensions of first engagement arm 162 can vary, in some implementations, first length 188 of first straight portion 172 may be greater than 10 mm, such as greater than 15 mm, greater than 20 mm, greater than 25 mm, or greater than 30 mm. The first length 188 of first straight portion 172 may be less than a certain value, such as less than 50 mm, less than 40 mm, less than 30 mm, or less than 25 mm. In some implementations, first length 188 of first straight portion 172 ranges from 10 mm to 40 mm, such as from 15 mm to 35 mm, from 20 mm to 30 mm, or from 20 mm to 25 mm.

First length 194 of first angled portion 174 is illustrated in FIG. 6B as being greater than first length 188 of first straight portion 172. Configuring the length of the angled portion to be longer than the length of the straight portion may be useful to offset compressor-distractor 160 to the side when attached to underlying bones (which may typically be the lateral side of the foot although may also be the medial side of the foot). Accordingly, in some configurations, a ratio calculated by dividing the length 188 of first straight portion 172 by the length 194 of first angled portion 174 may be less than or equal to 1.0, such as less than 0.9, less than 0.8, or less than 0.7. That being said, first straight portion 172 may have a sufficient length to offset first angled portion 174 above the anatomy over which the first straight portion is pinned. Accordingly, the ratio of length 188 of first straight portion 172 divided by length 194 of first angled portion 174 may be greater than 0.2, such as greater than 0.3, greater than 0.4, where then 0.5, greater than 0.6, or greater than 0.7. For example, the ratio may range from 0.5 to 1.0, such as from 0.6 to 0.9, or from 0.7 to 0.8. While first angled portion 174 may be sized longer than first straight portion 172, in other appropriate implementations, length 188 of first straight portion 172 may be greater than length 194 of first angled portion 174.

With further reference to FIG. 6A, second straight portion 176 of second engagement arm 164 can also define a length extending from a first end 196 to a second end 198. Second angled portion 178 of second engagement arm 164 can also define a length extending from a first end 200 to a second end 202. Second engagement arm 164 (e.g., the individual portions forming the engagement arm) can have any of the lengths, ratios, and configurations discussed above with respect to first engagement arm 162. For example, the length of second straight portion 176 may fall within any of the values discussed with respect to length 188 of first straight portion 172. Similarly, the length of second angled portion 178 can fall within any of the values discussed above with respect to length 194 of first angled portion 174. The lengths of first engagement arm 162 and second engagement arm 164 (and individual portions thereof) may be fixed (e.g., nonadjustable) as illustrated to provide a purpose configured arrangement for a target anatomical application. In other configurations, one or more arm portions may include a sliding connection or other adjustable interconnection allowing the length of the arm portion to be adjusted by the clinician.

In the illustrated configuration, first engagement arm 162 (e.g., the individual portions forming the arm) and second engagement arm 164 (e.g., the individual portions forming the arm) are symmetrically sized with substantially identical lengths. In alternative configurations, one engagement arm (e.g., any and/or all portions forming the arm) may have a different size (larger and/or smaller) than the other engagement arm (e.g., the corresponding portions thereof forming the arm) without departing from the scope of disclosure.

As introduced above, first angled portion 174 extends at a first acute angle 180 relative to a longitudinal axis 182 defined by the first pin-receiving hole 168 and second angled portion 178 extends at a second acute angle 184 relative to a longitudinal axis 186. As shown, first acute angle 180 and second acute angle 184 are measured from a longitudinal axis bisecting the geometric center of first angled portion 174 and second angled portion 178, respectively, to a location along longitudinal axes 182 and 186, respectively, extending out of the corresponding pin-receiving hole. Configuring first and second angled portions 174, 178 to extend at an angle relative to the corresponding straight portions can be useful to generally conform the profile of compressor-distractor 160 to the portion of foot over which the compressor-distractor is positioned. For example, configuring first and second angled portions 174, 178 to extend at acute angles relative to the corresponding straight portions can be useful to generally follow the sagittal plane curvature of the foot from the bones to which the compressor-distractor is attached. While configuring first and second angled portions 174, 178 to extend at acute angles relative to the corresponding straight portions can be beneficial for this anatomical contouring, in other applications, first and second angled portions 174, 178 may extend at an obtuse angle (or even a 90 degree angle) relative to the corresponding straight portions.

In the illustrated configuration, first acute angle 180 and second acute angle 184 are shown as defining a same value or degree of angulation. This can be useful to provide a symmetrical profile for first engagement arm 162 and second engagement arm 164. In other configurations, however, first acute angle 180 may be different than second acute angle 184 (larger or smaller). In general, first acute angle 180 and second acute angle 184 may each be less than 90°, for example, within a range from 25 degrees to 80 degrees, such as from 35 degrees to 65 degrees, or from 45 degrees to 50 degrees. In alternative implementations, compressor-distractor 160 may be configured with different arm portions that intersect at an approximately 90° angle in lieu of an acute angle.

In the illustrated configuration, first acute angle 180 and second acute angle 184 are fixed angles. In other words, first angled portion 174 extends at a permanent, nonadjustable angle relative to first straight portion 172, and second angled portion 178 extends at a permanent, nonadjustable angle relative to second straight portion 176. This arrangement can be useful to have compressor-distractor 160 purpose configured for a desired anatomical application without necessitating reconfiguration of the compressor-distractor by the clinician during surgery. If desired, first angled portion 174 and/or second angled portion 178 may be connectively attached to first straight portion 172 and second straight portion 176, respectively, via a hinged or other adjustable angle interconnections.

First straight portion 172 of first engagement arm 162 is operatively connected to first angled portion 174 of the first engagement arm. Similarly, second straight portion 176 of second engagement arm 164 is operatively connected to second angled portion 178. Each respective angled portion can be directly connected to a corresponding straight portion, or there may be one or more intermediate portions separating a straight portion from an angled portion.

In the illustrated example of FIG. 6A, first engagement arm 162 also includes a first transverse portion 204 connecting first straight portion 172 to first angled portion 174. Also, second engagement arm 164 includes a second transverse portion 206 connecting second straight portion 176 to second angled portion 178. Configuring first and/or second engagement arms 162, 164 with respective transverse portions may be useful to help the clinician more easily insert pins into the pin-receiving holes defined by the straight portions 172, 176. In practice, a clinician may typically use a powered driver to drive a pin through a pin-receiving hole of the compressor-distractor and into the underlying bone. A powered driver may typically include a collet defining an outer face of the driver from which the pin extends. Depending on the configuration of compressor-distractor 160, direct connection between the angled arm portion and the straight arm portion may cause interference between the angled arm portion and the collet of the driver as the clinician is attempting to drive the pin to a desired depth. Accordingly, offsetting the angled arm portion relative to the straight arm portion may be beneficial to provide clearance for the collet of the driver, e.g., as the collect is driven close to and/or in contact with the end face of the straight portion, facilitating easier use of the compressor-distractor by the clinician.

In the illustrated configuration, first transverse portion 204 extends at an approximately 90° angle (e.g., ±10%) relative to longitudinal axis 182 defined by first pin-receiving hole 168. Second transverse portion 206 is also illustrated as extending at an approximately 90° angle (e.g., ±10%) relative to longitudinal axis 186 defined by second pin-receiving hole 170. One or both transverse portions may extend at different angles to connect a straight portion to a corresponding angled portion without departing from the scope of disclosure. In addition, while the length of first transverse portion 204 and second transverse portion 206 may vary, in some configurations, each portion may have a length ranging from 1 mm to 10 mm, such as from 2 mm to 8 mm, or from 3 mm to 6 mm. First transverse portion 204 and second transverse portion 206 may have the same length, or one may be a different length than the other transverse portion.

In general, features described as pin-receiving holes may be void spaces extending linearly through a portion of compressor-distractor 160 and configured (e.g., sized and/or shaped) to pass a pin inserted therethrough into an underlying bone portion. While the pin-receiving holes may have any polygonal (e.g., square, rectangle) or arcuate (e.g., curved, elliptical) shape, the pin-receiving holes may typically have a circular cross-sectional shape. In some examples, the pin-receiving holes have a diameter ranging from 0.1 mm to 10 mm, such as from 0.5 mm to 4 mm.

In the illustrated configuration, first linear portion 172 and second linear portion 176 define first and second pin-receiving holes 168 and 170, respectively. First and second linear portions 172, 176 each extend from a first terminal end 190, 196, respectively, which can be placed in contact with underlying bone portions when using compressor-distractor 160. In some implementations, one or both of the first ends of the linear portions include cut outs 173, 175, which may be characterized by removal of part but not all of the sidewall adjacent the first end. For example, a cut out may be formed by a region of first linear portion 172 and/or second linear portion 176 adjacent first end 190, 196, respectively, that is devoid of material over some but not all of the cross-section of the linear portion. The cut out may be positioned to be visible from a side (e.g., dorsal or topside) of foot 10, when compressor-distractor 160 is attached to the foot. This may provide visualization to the clinician showing when a pin has crossed through the cut out into the underlying bone portion. The region of the linear portion of the arm opposite the cut out may be defined by a region material that can be placed in contact with the underlying bone portion. In other applications, compressor-distractor 160 does not include such cutouts.

Compressor-distractor 160 can have any suitable number of pin-receiving holes. In some configurations, one or both of first engagement arm 162 and second engagement arm 164 includes multiple pin-receiving hole. The longitudinal axis of one or more pin-receiving holes defined by first engagement arm 162 may be parallel to the longitudinal axis of one or more pin-receiving holes defined by second engagement arm 164. This can allow compressor-distractor 160 to be removed off of the parallel pins while leaving the pins in place, if desired. Additionally or alternatively, the longitudinal axis of one or more pin-receiving holes defined by first engagement arm 162 may be skewed or angled relative to one or more pin-receiving holes defined by second engagement arm 164. This can allow the clinician to insert one or more crossing pins to fixate compressor-distractor 160 to one or both underlying bone portions.

As briefly discussed above, compressor-distractor 160 can open and close to compress and distract the bones to which to the compressor-distractor is secured. To facilitate movement, compressor-distractor 160 is illustrated as having an actuator 166. Actuator 166 is configured to control movement of first engagement arm 162 relative to second engagement arm 164. Actuator 166 may be implemented using any feature that provides controllable relative movement between the two engagement arms, such as rotary movement, sliding movement, or other relative translation. In some configurations, actuator 166 is configured to move first and second engagement arms 162, 164 at least 1 mm away from each other, such as a distance ranging from 1 mm to 45 mm, a distance ranging from 1 mm to 5 mm, or a distance ranging from 1 mm to 2.5 mm during distraction and/or compression. Actuator 166 may be actuated during compression until the faces of the bones to which compressor-distractor 160 is attached are suitably compressed and/or the sidewall faces of first and second engagement arms 162, 164 contact each other.

In the example of FIG. 6A, actuator 166 is illustrated as including a rail 208, which may also be referred to as a shaft, connected to first engagement arm 162 and second engagement arm 164. Shaft 208 may be threaded and actuator 166 may further include a knob 210 coupled to the shaft. Rotation of knob 210 in one direction may cause first engagement arm 162 to move closer to second engagement arm 164, while rotation of the knob in the opposite direction can cause the first engagement arm to move away from the second engagement arm. In other configurations, shaft may have notches or grooves (e.g., forming a rack and pinion) or other configuration to allow one engagement arm to translate relative to the other engagement arm. Shaft 208 can have any suitable cross-sectional shape (e.g., circular, square, rectangular).

To secure actuator 166 to compressor-distractor 160, the actuator may be fixedly connected to one of the arms. For example, shaft 208 of actuator 166 may be fixedly attached along its length to first engagement arm 162 and rotatable relative to the arm. As a result, when knob 210 is rotated, second engagement arm 164 may move along the length of shaft 208 towards and/or away from first engagement arm 162. This provides relative movement between the two arms while first engagement arm 162 remains in a fixed position relative to actuator 166.

In the illustrated configuration, first engagement arm 162 is implemented as a stationary arm that does not move relative to the length of shaft 208, while second engagement arm 164 is a movable arm that moves along the length of the shaft. When compressor-distractor 160 is configured with at least one movable arm, the movable arm may be sized wider in the region through which shaft 208 extends then the adjacent non-movable arm. For example, second engagement arm 164 is illustrated as including a region of maximum width 212 that is greater than the maximum width of the corresponding first engagement arm 162. Enlarging the width of the movable engagement arm at least over the region through which shaft 208 extends can be beneficial to increase the amount of surface area contact between the shaft and engagement arm. This can increase the stability of the movable engagement arm. In other configurations, both engagement arms may be movable along the length of shaft 208 without departing from the scope of the disclosure.

To help stabilize first engagement arm 162 relative to second engagement arm 164 during movement along shaft 208, compressor-distractor 160 may also include one or more secondary shafts extending parallel to a first shaft 208. For example, compressor-distractor 160 may include one or more secondary shafts that do not have actuation features (e.g., threading, grooves) extending parallel to one or more shafts that do have actuation features. In FIG. 6A, for example, actuator 166 has an unthreaded shaft 214. Unthreaded shaft 214 extends parallel to threaded shaft 208 and helps stabilize second engagement arm 164 as it moves along the shaft towards and away from first engagement arm 162. Shaft 208 is illustrated as a threaded shaft extending through a threaded aperture in the sidewall of second engagement arm 164, while unthreaded shaft 214 is illustrated as extending through an unthreaded aperture in the sidewall of the engagement arm.

In use, a clinician can position compressor-distractor 160 adjacent to and/or in contact with underlying bone portions and insert first and second pins through the first and second pin-receiving holes, 168, 170, into the underlying bone portions. The configuration of compressor-distractor 160 as described herein may provide conformance to the general anatomical curvature of the lateral portion of foot 10, helping to position the compressor-distractor at an offset location away from the surgical site being worked on by the clinician.

For example, in use, a clinician can position first pin-receiving hole 168 of first engagement arm 162 over a first bone portion, such as a medial cuneiform, an intermediate cuneiform, a lateral cuneiform, and/or a cuboid. First engagement arm 162 can include first straight portion 172 (defining the first pin-receiving hole 168) that extends dorsally and laterally from the first bone portion, when installed on the underlying bone. First engagement 162 can also have first angled portion 174 extending plantarly and laterally from the first straight portion, when installed on the underlying bone.

Concurrent with or separate from positioning first pin-receiving hole 168 over the first bone portion, the clinician can position second pin-receiving hole 170 of second engagement arm 164 over a second bone portion, such as a first metatarsal, a second metatarsal, a third metatarsal, a fourth metatarsal, and/or a fifth metatarsal. Second engagement arm 164 can have second straight portion 176 (defining the second pin-receiving hole 170) that extends dorsally and laterally from the second bone portion, when installed on the underlying bone. Second engagement arm 164 can also have second angled portion 178 extending plantarly and laterally from the second straight portion, when installed on the underlying bone.

Figure 6C:
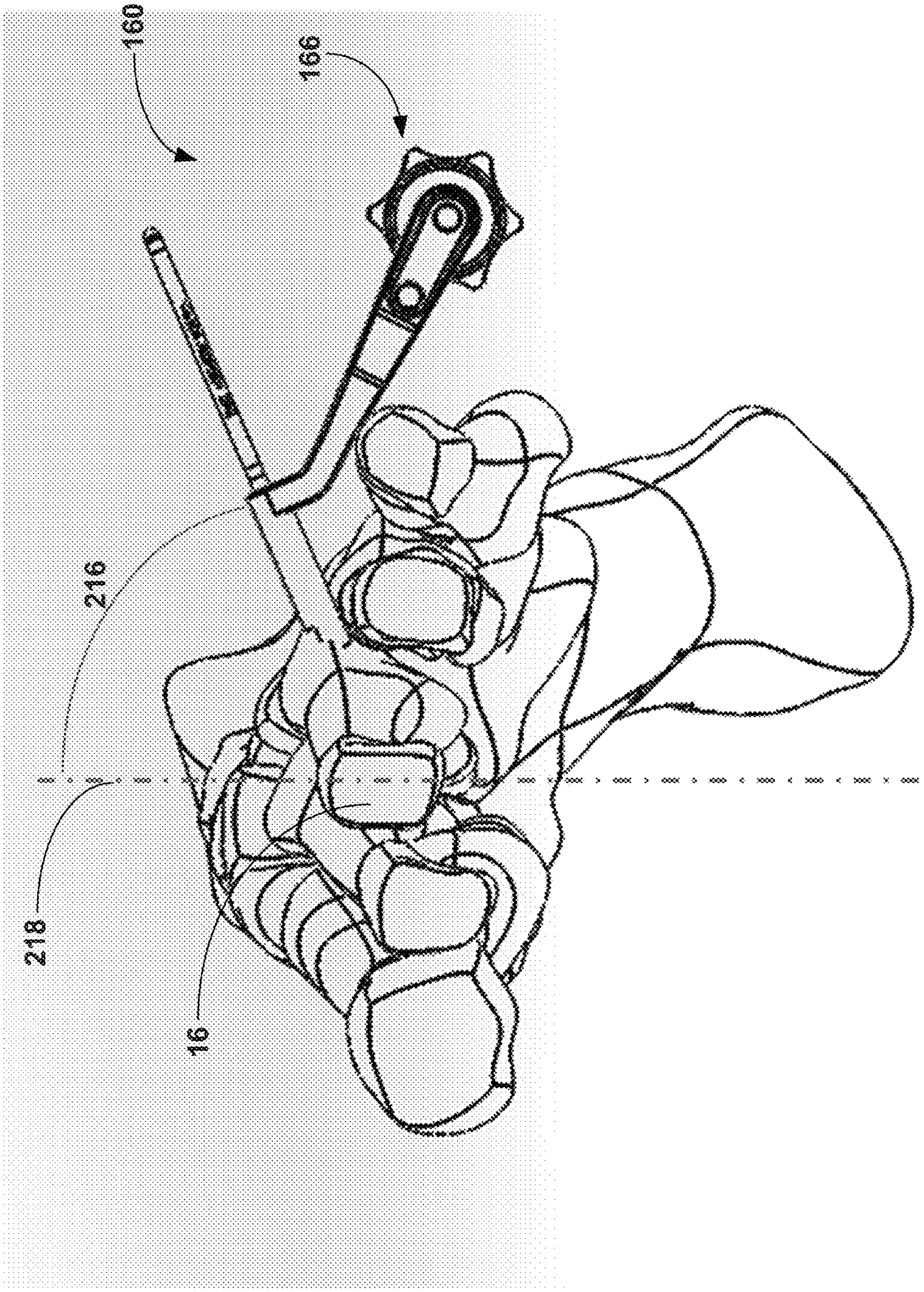
FIG. 6C is a frontal view of a foot illustrating an example configuration of a compressor-distractor positioned on the foot.

FIG. 6C is a frontal view of foot 10 illustrating an example configuration of compressor-distractor 160 positioned on the foot. FIG. 6C illustrates compressor-distractor 160 extending laterally away from an attachment site to underlying bone portions. In particular, in the illustrated configuration, compressor-distractor 160 is positioned extending at a dorsal-lateral angle away from the attachment site until a curved or angled region of the compressor-distractor 160 changes the direction of the compressor-distractor engagement arms to a plantar-lateral direction. In some configurations, compressor-distractor 160 is configured to position actuator 166 of the device off the lateral-most side of the fifth metatarsal of the foot, e.g., with at least a portion of the actuator above, below, and/or substantially co-planar with the sagittal plane in which the fifth metatarsal resides.

Independent of the specific configuration of compressor-distractor 160, the clinician can insert a first pin through first pin-receiving hole 168 and into the underlying first bone portion and also insert a second pin through second pin-receiving 170 hole and into the underlying second bone portion. The clinician can insert the first pin before the second pin or the second pin before the first pin as reference to first and second pins do not imply in order of operation. The clinician can insert any one or more additional pins desired, in configurations in which compressor-distractor 160 includes more than two pin holes.

As a result of the configuration of compressor-distractor 160, first straight portion 172 and second straight portion 176, and first and second pins inserted therethrough, may extend at an angle 216 relative to the sagittal plane 218 defining a vertical axis of the foot. For example, first straight portion 172 and second straight portion 176, and first and second pins inserted therethrough, may extend at an angle 216 ranging from 50 degrees to 85 degrees with respect to sagittal plane 218, such as an angle ranging from 60 degrees to 75 degrees.

In either case, once suitably attached, the clinician can actuate actuator 166 of compressor-distractor 160 to adjust a separation distance between the two bone portions to which first engagement arm 162 and second engagement arm 164, respectively, are attached. The clinician may move the arms away from each other (e.g., to open the joint space to help prepare the end faces of one or both bones, for cleanup and removal of bone or tissue, or other reasons). The clinician may move the arms towards each other (e.g., to apply a compressive force to close the joint space in preparation for fixation and fusion). For example, the clinician may actuate actuator 166 at least until the end faces of the bone portions to which first engagement arm 162 and second engagement arm 164 are attached are in contact with each other. The clinician may optionally apply hand pressure to bones being realigned prior to, concurrent with, and/or after use of compressor-distractor 160 to further compress and/or realigned a bone portion.

In some implementations, the clinician attaches one engagement arm of compressor-distractor 160 to one bone portion and then manipulates (e.g., repositions) the other bone portion before attaching the second engagement arm of the compressor-distractor to the other bone portion. FIGS. 7A-7E illustrate an example bone realignment technique that can be performed using a compressor-distractor, such as compressor-distractor 160 described herein.

Figure 7A:
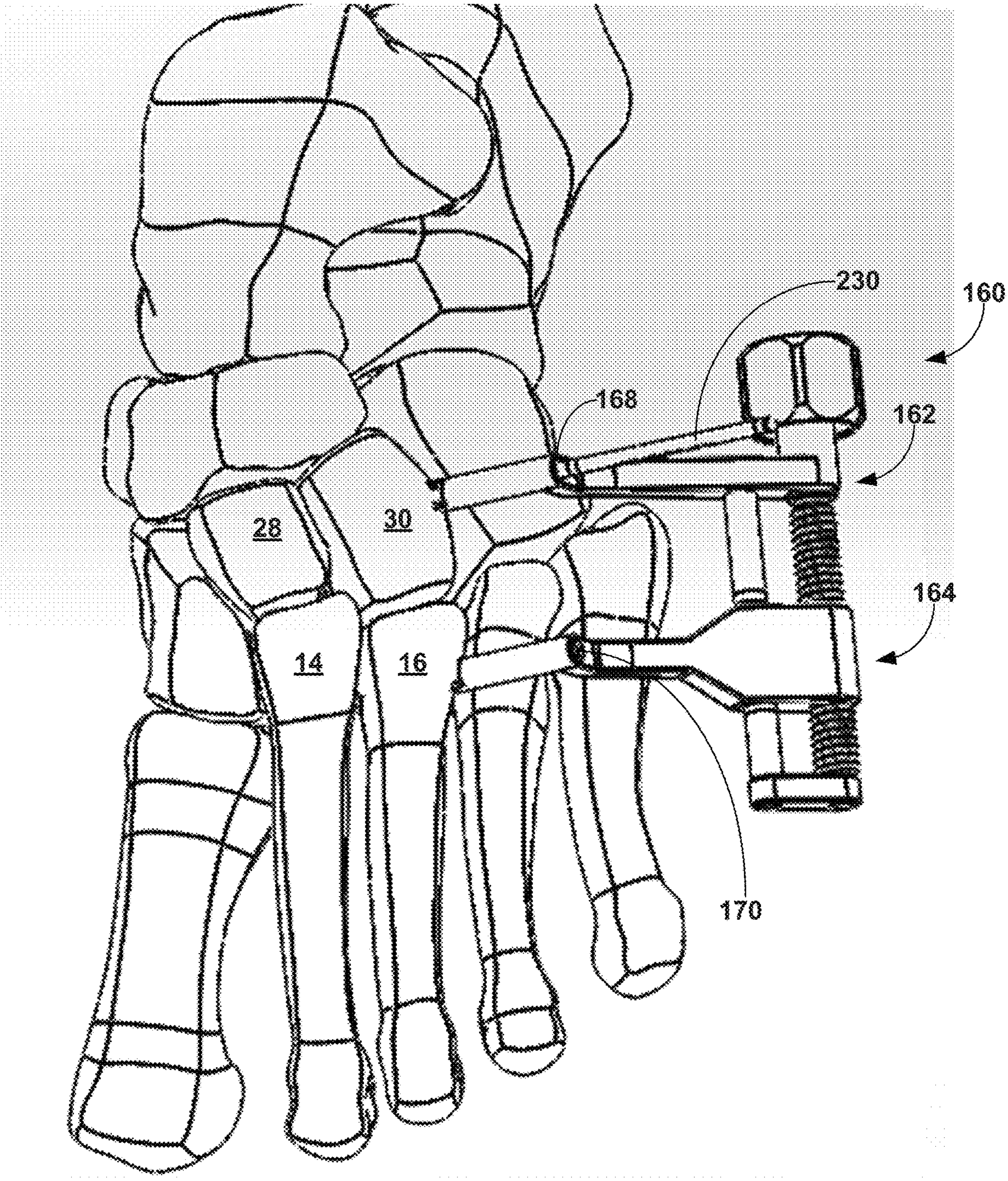
FIGS. 7A-7E illustrate an example bone realignment technique that can be performed using a compressor-distractor.

FIG. 7A is a dorsal view of foot 10 illustrating an example positioning step of compressor-distractor 160. In this example, first engagement arm 162 of compressor-distractor 160 is positioned over lateral cuneiform 30 and second engagement arm 164 of the compressor-distractor is positioned over third metatarsal 16. The engagement arms of compressor-distractor 160 may be positioned so pins subsequently inserted through the engagement arms are inserted into a dorsal-lateral quadrant of the bone portions and extend in a dorsal-lateral direction away from the bone portions. As shown in FIG. 7A, the clinician may initially insert a first pin 230 through first pin-receiving hole 168 into the underlying cuneiform (e.g., lateral cuneiform 30).

Prior to inserting a second pin through second pin-receiving hole, the clinician may reposition manually reposition second metatarsal 14 and/or third metatarsal 16 (optionally with the use of a separate surgical instrument, such as a tenaculum). For example, the clinician may manually reposition and/or compress second metatarsal 14 and/or third metatarsal 16 applying a transverse force and a frontal plane force to close a gap in the second and third metatarsals.

Figure 7B:
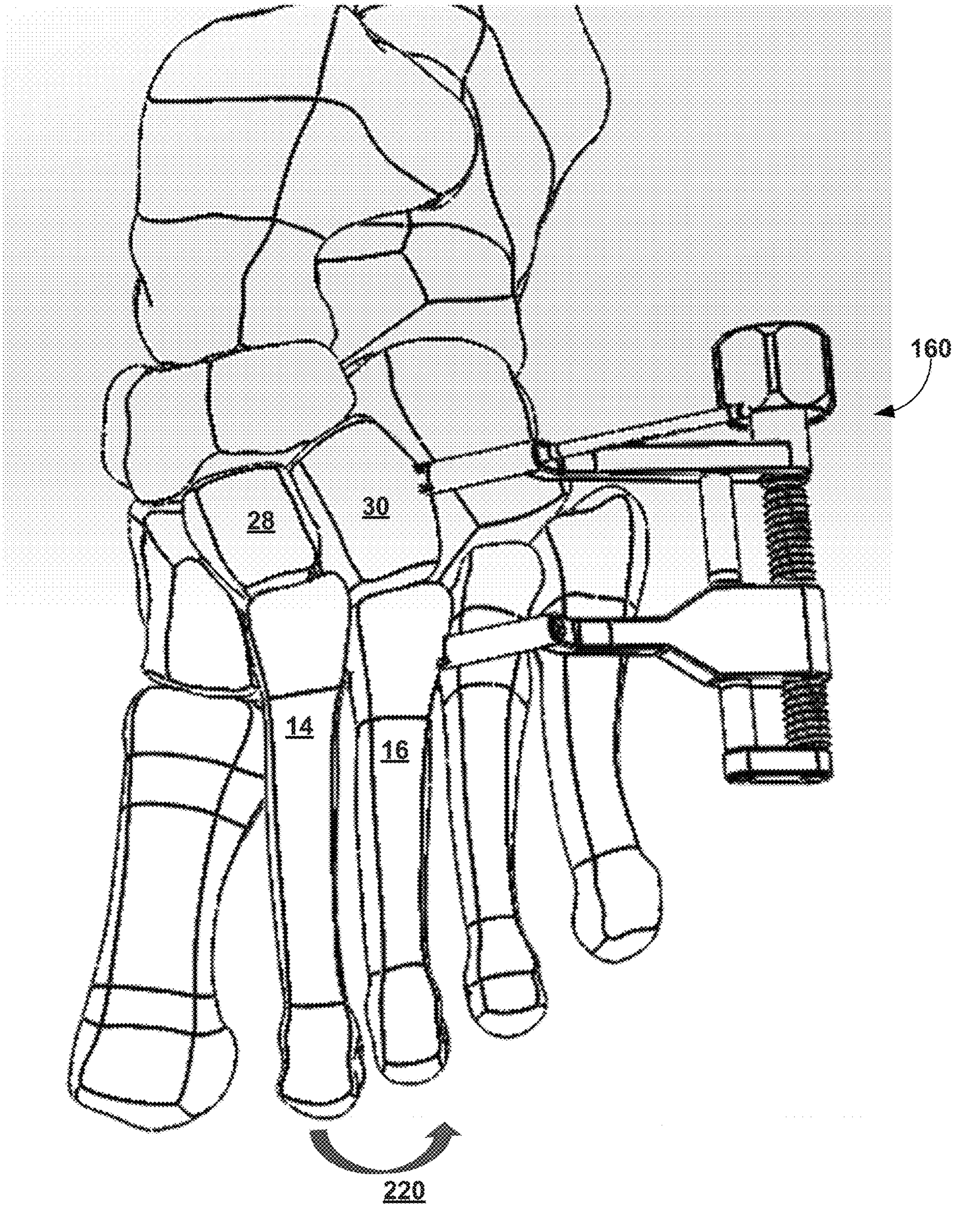
Figure 7C:
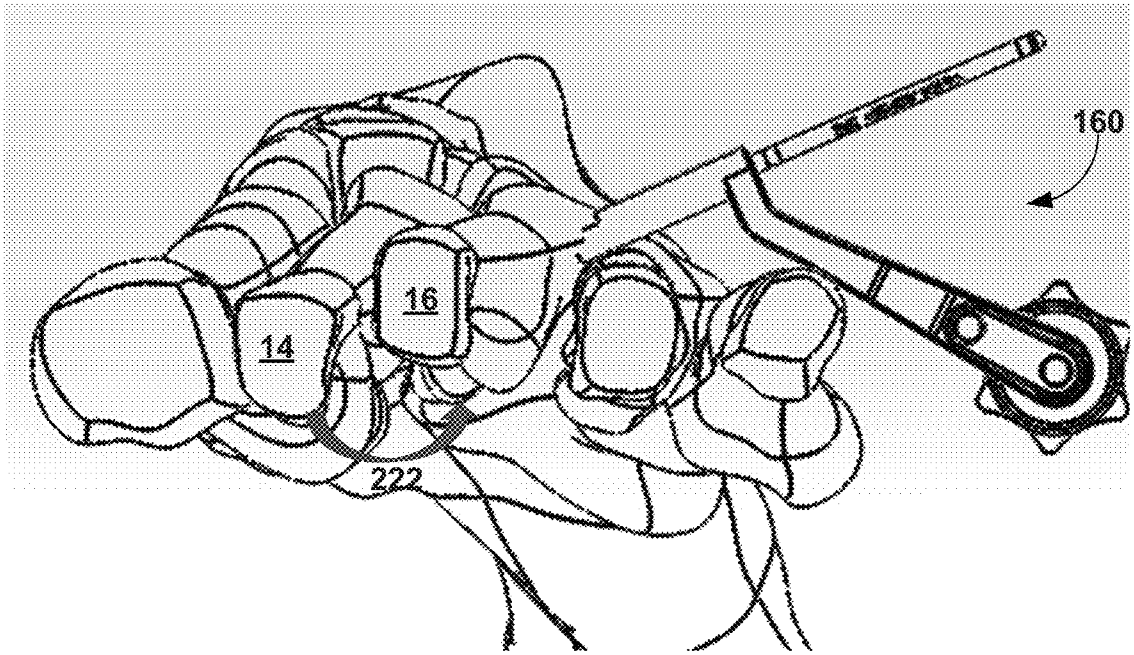
Figure 7D:
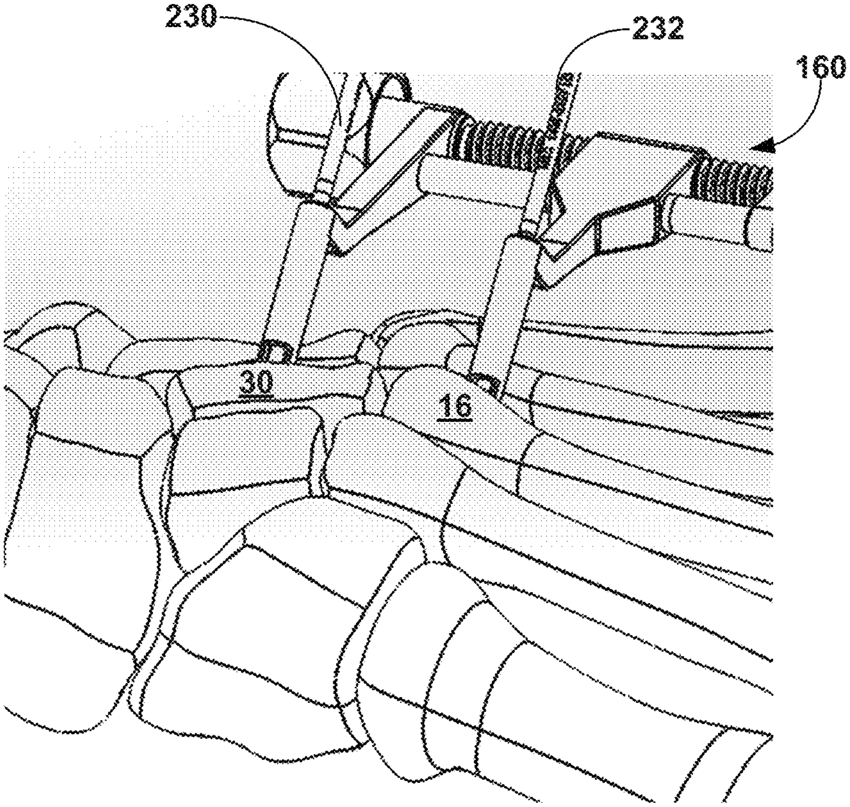

For example, with reference to FIG. 7B, the clinician may apply a laterally-directed force 220 in the traverse plane (e.g., to one or both of second metatarsal 14 and third metatarsal 16) to close the intermetatarsal angle(s) between one or more lesser metatarsals (e.g., between second metatarsal 14 and third metatarsal 16, between third metatarsal 16 and fourth metatarsal 18, and/or between fourth metatarsal 18 and fifth metatarsal 20). With reference to FIG. 7C, the clinician may also apply a rotational force to 222 (e.g., to one or both of second metatarsal 14 and third metatarsal 16), e.g., to rotate the base of one or both metatarsals. This rotational force can be done to bring the dorsal surfaces of one or both metatarsals into alignment with the dorsal surface of the corresponding opposed cuneiform (e.g., so the dorsal surfaces of the metatarsal and cuneiform are substantially coplanar within the sagittal plane). This can remove a potential step off between the dorsal surface of the base of the metatarsal and the dorsal surface of the opposed cuneiform. For example, FIG. 7D illustrates the dorsal surface of the base of third metatarsal 16 substantially aligned with the dorsal surface of the proximal end of lateral cuneiform 30. The clinician can apply the transverse plane correction force before, after, and/or concurring with applying the frontal plane correction force. The clinician may move one or both metatarsals in the sagittal plane through a separate movement or concurrent with applying the transverse plane and/or frontal plane-directed force.

Figure 7E:
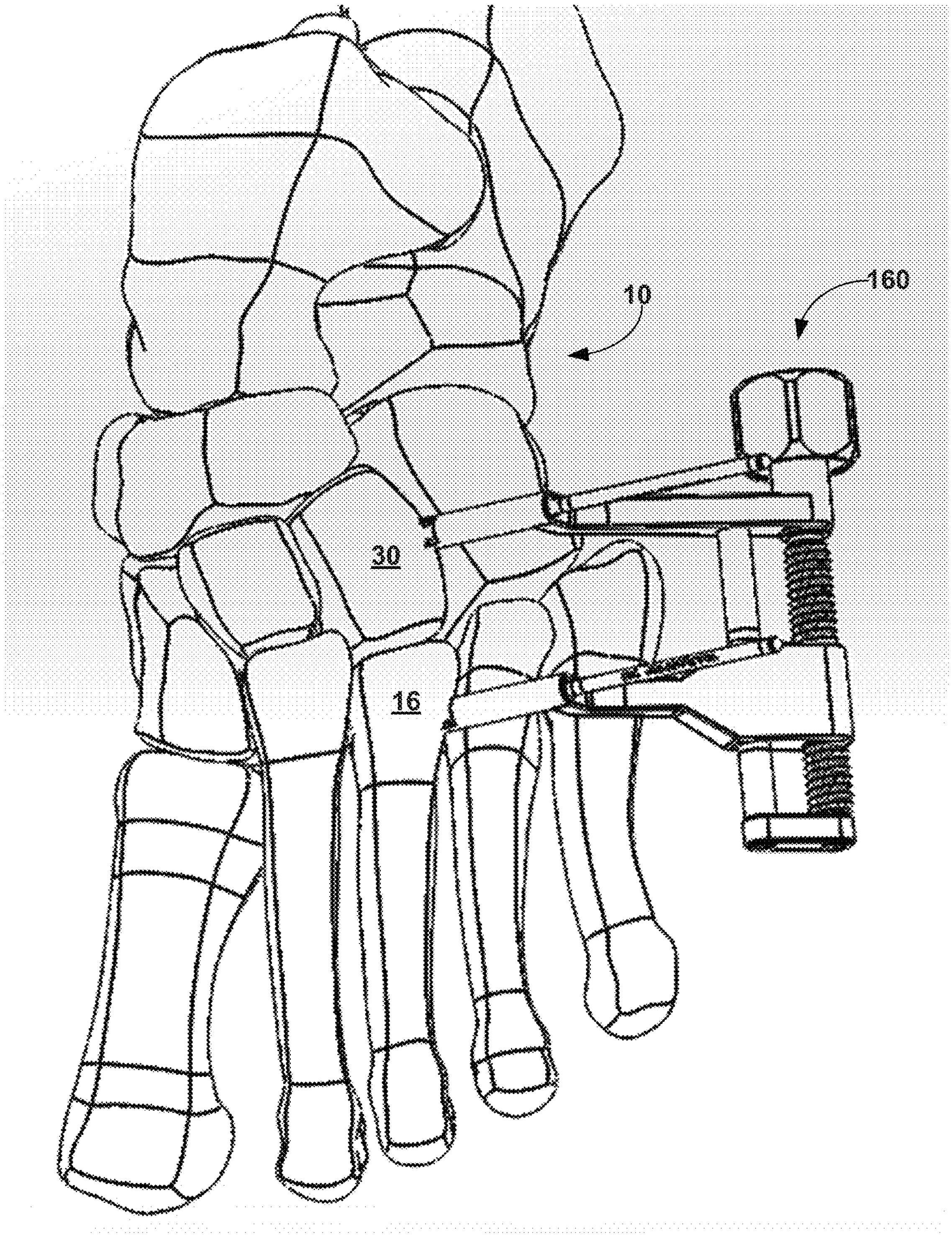

While holding manual compression, the clinician can insert a second pin 232 through second pin-receiving hole 170 into the underlying metatarsal (e.g., third metatarsal 16). This is illustrated in FIG. 7D. The clinician can then actuate actuator 166, finishing compression, as illustrated in FIG. 7E.

Compressor-distractor 160 in the examples of FIGS. 6A-6C and FIGS. 7A-7E has generally been illustrated and described as being positioned over first and second bones (e.g., lateral cuneiform 30 and third metatarsal 16, respectively), with first and second pins then being inserted through first pin-receiving hole 168 and second pin-receiving hole 170 to pin the compressor-distractor to the underlying bone portions. In practice, one or more pins may be inserted into the first and/or second bones and a compressor-distractor (e.g., compressor-distractor 160) then positioned over the pins (e.g., by sliding the compressor-distractor plantarly or downwardly over the pins) instead of inserting the one or more pins through a pin-receiving hole of the compressor-distractor into the underlying bone(s). In these applications, the clinician may utilize a pin guide to facilitate controlled positioning of the one or more pins into the one or more bones.

Figure 6D:
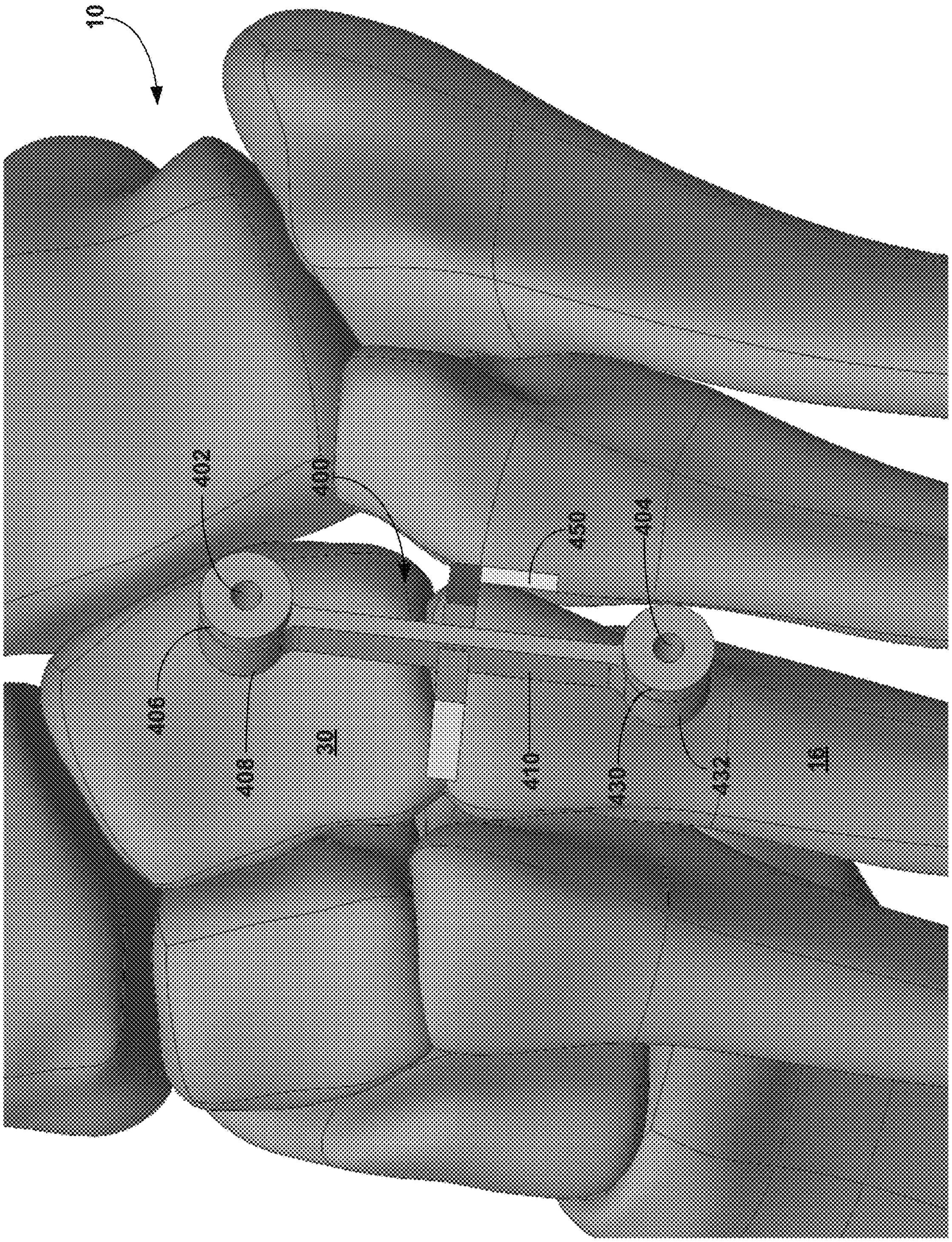
FIG. 6D is top view of an example pin guide that can be used to guide positioning of first and second pins into first and second bone portions, respectively.

FIG. 6D is top view of an example pin guide 400 that can be used to guide positioning of first and second pins into first and second bone portions, respectively. Pin guide 400 can have a body defining a first pin-receiving hole 402 and a second pin-receiving hole 404. The first pin-receiving hole 402 can receive a first pin, while the second pin-receiving hole 404 can receive a second pin. The first pin and the second pin can be inserted into different bones or bone portions being worked upon. For example, the first pin can be inserted through first pin-receiving hole 402 and into an underlying first bone portion, such as a bone on a proximal side of a TMT joint (e.g., a cuneiform or cuboid). In some implementations, the first bone is on the proximal side of a TMT joint of a lesser metatarsal and is one or more of intermediate cuneiform 28, lateral cuneiform 30, and cuboid 32. The second pin can be inserted through second pin-receiving hole 404 and into an underlying second bone portion, such as a bone on a distal side of a TMT joint (e.g., a metatarsal). In some implementations, the bone is on the distal side of a TMT joint of a lesser metatarsal and is one or more of second metatarsal 14, third metatarsal 16, fourth metatarsal 18, and fifth metatarsal 20. In FIG. 6D, first pin-receiving hole 402 is illustrated as being positioned over lateral cuneiform 30, and second pin-receiving hole 404 is illustrated as being positioned over third metatarsal 16.

Pin guide 400 can position first pin-receiving hole 402 and second pin-receiving hole 404 at locations corresponding to first pin-receiving hole 168 and second pin-receiving hole 170, respectively, of compressor-distractor 160. For example, pin guide 400 can be configured (e.g., sized and/or shaped) to position first pin-receiving hole 402 and second pin-receiving hole 404 at locations such that, when first and second pins are inserted through the respectively pin-receiving holes into underlying bones and the pin guide is subsequently removed, the pins are positioned at a spacing and orientation corresponding to the positioning and spacing of first pin-receiving hole 168 and second pin-receiving hole 170 of compressor-distractor 160. This can allow the clinician to then install compressor-distractor 160 down over the pins inserted into the underlying bone portions using pin guide 400.

Each feature described as a pin-receiving hole of pin guide 400 can be defined by a pin-receiving body having a length extending from a first end 406 to a second end 408. The two pin-receiving bodies defining first pin-receiving hole 402 and second pin-receiving hole 404 can be joined together by a bridge 410. The separation distance between first pin-receiving hole 402 and second pin-receiving hole 404 established by bridge 410 can correspond to any of the spacings between first pin-receiving hole 168 and second pin-receiving hole 170 of compressor-distractor 160. Further, first pin-receiving hole 402 and second pin-receiving hole 404 of pin guide 400 can have any of configurations (e.g., size and/or shape) described as being suitable for first pin-receiving hole 168 and second pin-receiving hole 170 of compressor-distractor 160.

The longitudinal axis of one or more pin-receiving holes (e.g., first pin-receiving hole 402) defined by pin guide 400 may be parallel to the longitudinal axis of one or more other pin-receiving holes (e.g., second pin-receiving hole 404) defined by this pin guide. This can position pins inserted through the respective pin-receiving holes parallel to each other. Additionally or alternative, the longitudinal axis of one or more pin-receiving holes (e.g., first pin-receiving hole 402) defined by pin guide 400 may be angled or skewed relative to the longitudinal axis of one or more other pin-receiving holes (e.g., second pin-receiving hole 404) defined by this pin guide. This can position pins inserted through the respective pin-receiving holes at a non-parallel angulation relative to each other.

Figure 6E:
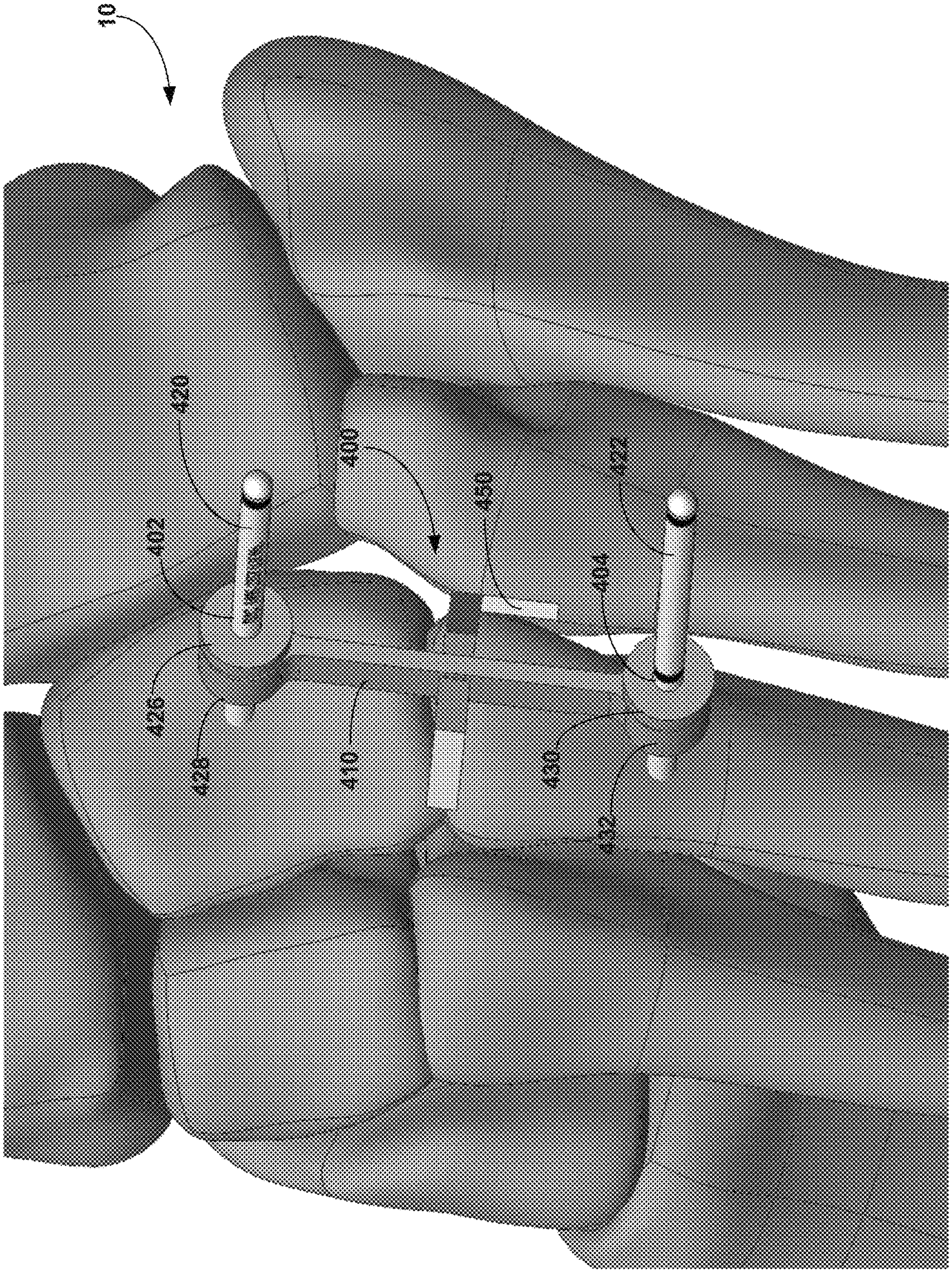
FIG. 6E is a top view of the example pin guide from FIG. 6D showing first and second pins 420, 422 inserted through a first pin-receiving hole and a second pin-receiving hole, respectively.

FIG. 6E is a top view of the example pin guide 400 from FIG. 6D showing first and second pins 420, 422 inserted through first pin-receiving hole 402 and second pin-receiving hole 404, respectively. First pin-receiving hole 402 and second pin-receiving hole 404 may be angled relative to each other to angle the first pin 420 and second pin 422 inserted therethrough relative to each other. For example, the longitudinal axis defined by each of the two pin-receiving holes may be angled relative to each other in the sagittal plane by an angle 424. Angle 424 may be measured between two linear pins (e.g., first pin 420 and second pin 422) inserted through respective receiving holes in the perspective of the sagittal plane. While the degree of angular offset between first pin-receiving hole 402 and second pin-receiving hole 404 may vary, in some examples, angle 424 may range from 5° to 12°, such as from 7° to 10°, or from 8 to 9°, or approximately 8.5°. The two pin-receiving holes may be offset in a direction that causes the metatarsal to rotate (e.g., downwardly or plantarly) in the sagittal plane as the compressor-distractor 160 is subsequently installed over the two angled pins.

For example, first pin-receiving hole 168 and second pin-receiving hole 170 of compressor-distractor 160 may be parallel to each other. After inserting first pin 420 and second pin 422 at an angle relative to each other using pin guide 400, the pin guide can be removed from the pins and the compressor-distractor installed over the pins. Compressor-distractor 160 can be inserted over the angled pins by threading the angled pins into the parallel pin-receiving holes of the compressor-distractor, thereby causing the pins to move from a substantially angled alignment to a substantially parallel alignment dictated by the angulation of the pin-receiving holes of the compressor-distractor. Compressor-distractor 160 may then be used to distract the bone portions into which the pins are inserted (e.g., by actuating the actuator to draw the bone portions away from each other) and/or compress the bone portions into which the pins are inserted (e.g., by actuating actuator to move the bone portions towards each other).

In some implementations when pin guide 400 is configured to position first pin 420 and second pin 422 at angles relative to each other, the pin guide may include one or more removable pin tubes. Each removable pin tube may be insertable into and removable from a corresponding pin-receiving body of pin guide 400 and can define the pin-receiving hole. For example, pin guide 400 may include a first pin tube 426 inserted into a first pin-receiving body 428 to define first pin-receiving hole 402 and a second pin tube 430 inserted into a second pin-receiving body 432 to define second pin-receiving hole 404. Each pin tube may be threaded about an exterior perimeter to be threadingly inserted into a corresponding pin-receiving body (e.g., by screwing the pin tube into the pin-receiving body). Alternatively, the pin tube may be inserted into a pin-receiving body without be affixed to the body and/or one or other mechanical fixation elements can be used to releasably attach the pin tube to the pin-receiving body.

Figure 6F:
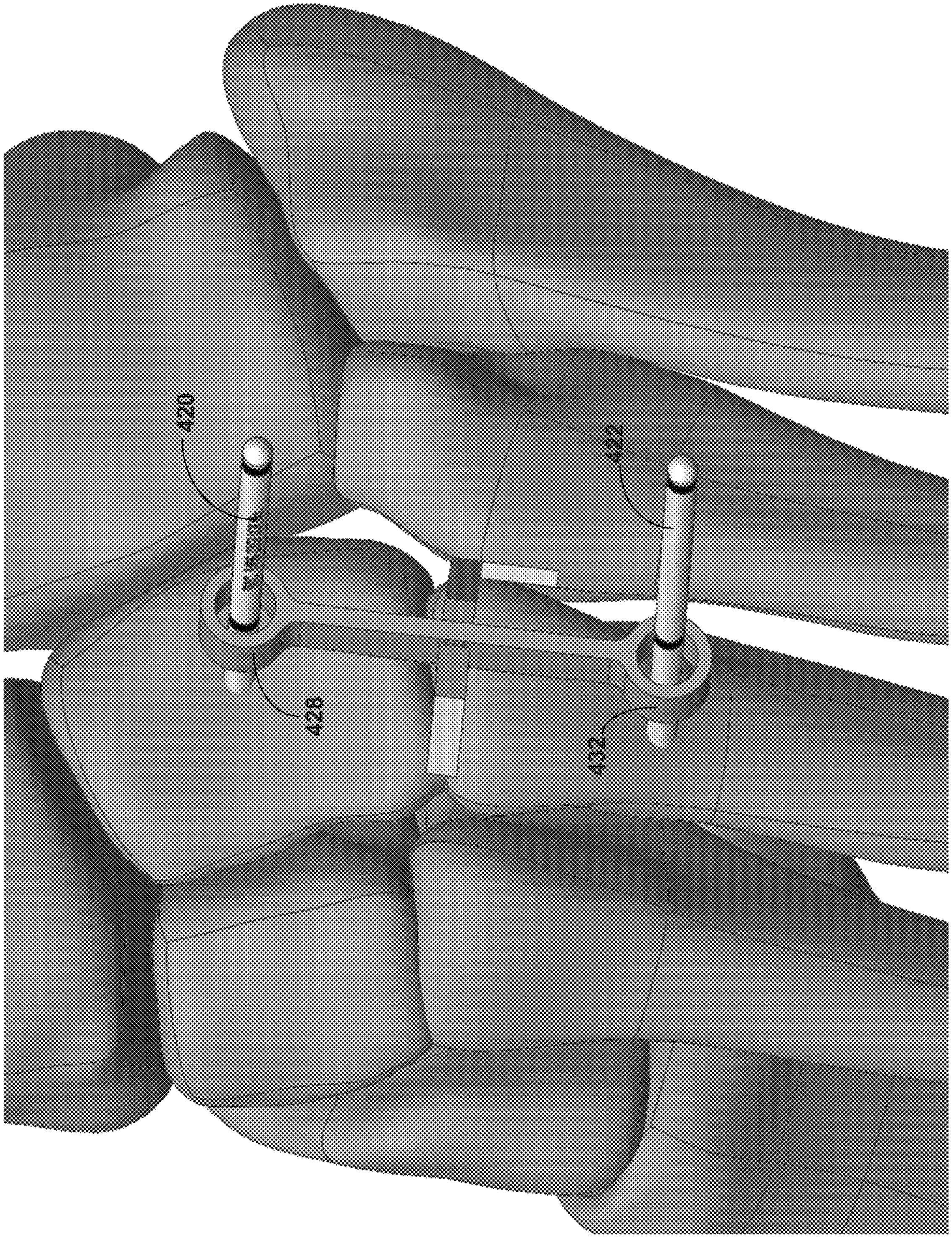
FIG. 6F is a top view of the example pin guide from FIG. 6E showing a first pin tube and a second pin tube removed from the corresponding pin receiving bodies.

In use, first pin 420 and second pin 422 can be inserted through first pin-receiving hole 402 and second pin-receiving hole 404, respectively, defined by the first pin tube 426 and second pin tube 430 into underlying bones. The first pin tube 426 and second pin tube 430 can then be removed from the first pin-receiving body 428 and the second pin-receiving body 432 over the pins (e.g., while leaving the pins inserted into the underlying bone portions). This can create a larger opening defined by first pin-receiving body 428 and second pin-receiving body 432 surrounding first pin 420 and second pin 422, respectively, than the smaller first pin-receiving hole 402 and second pin-receiving hole 404 defined by the corresponding pin tubes. For example, FIG. 6F is a top view of the example pin guide 400 from FIG. 6E showing first pin tube 426 and second pin tube 430 removed from the corresponding pin receiving bodies. This can configure pin guide 400 with larger cavities extending about first pin 420 and second pin 422, allowing the pin guide 400 to be removed of the angled pins, e.g., without substantially moving the relative positions of the pins when removing the pin guide.

To help facilitate the positioning of pin guide 400 over one or more bones into which one or more pins are to be inserted, the pin guide may include one or more locating features. The locating features may be insertable into a bone and/or a joint space between adjacent bones to provide anatomical reference locations for pin guide 400 relative to target anatomy of the foot. For example, pin guide 400 may include one or more pins and/or spacers 450 that are associated with the pin guide and used to help orient the pin guide. In the illustrated example of FIG. 6D-6F, pin guide 400 includes a spacer 450 positionable in an intermetatarsal space to orient the pin guide relative to target bones into which pins are to be inserted using the pin guide. Pin guide 400 can include any number and configuration of locating features as described in greater detail herein as being suitable for cut guide 150.

Figure 6G:
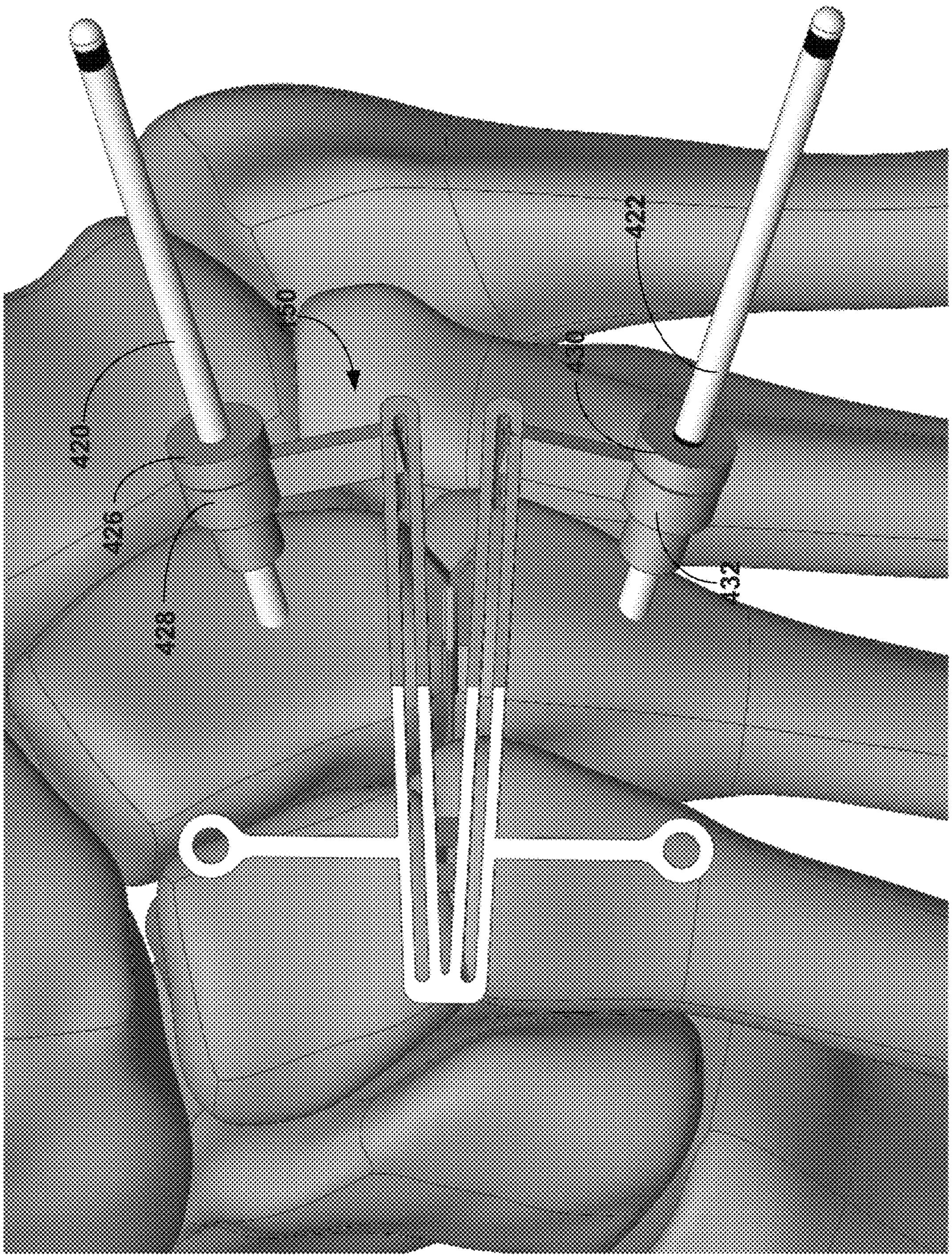
FIGS. 6G and 6H illustrate an example configuration of a cut guide configured with pin-receiving holes positioned and/or configured as described as being provided by an example pin guide.
Figure 6H:
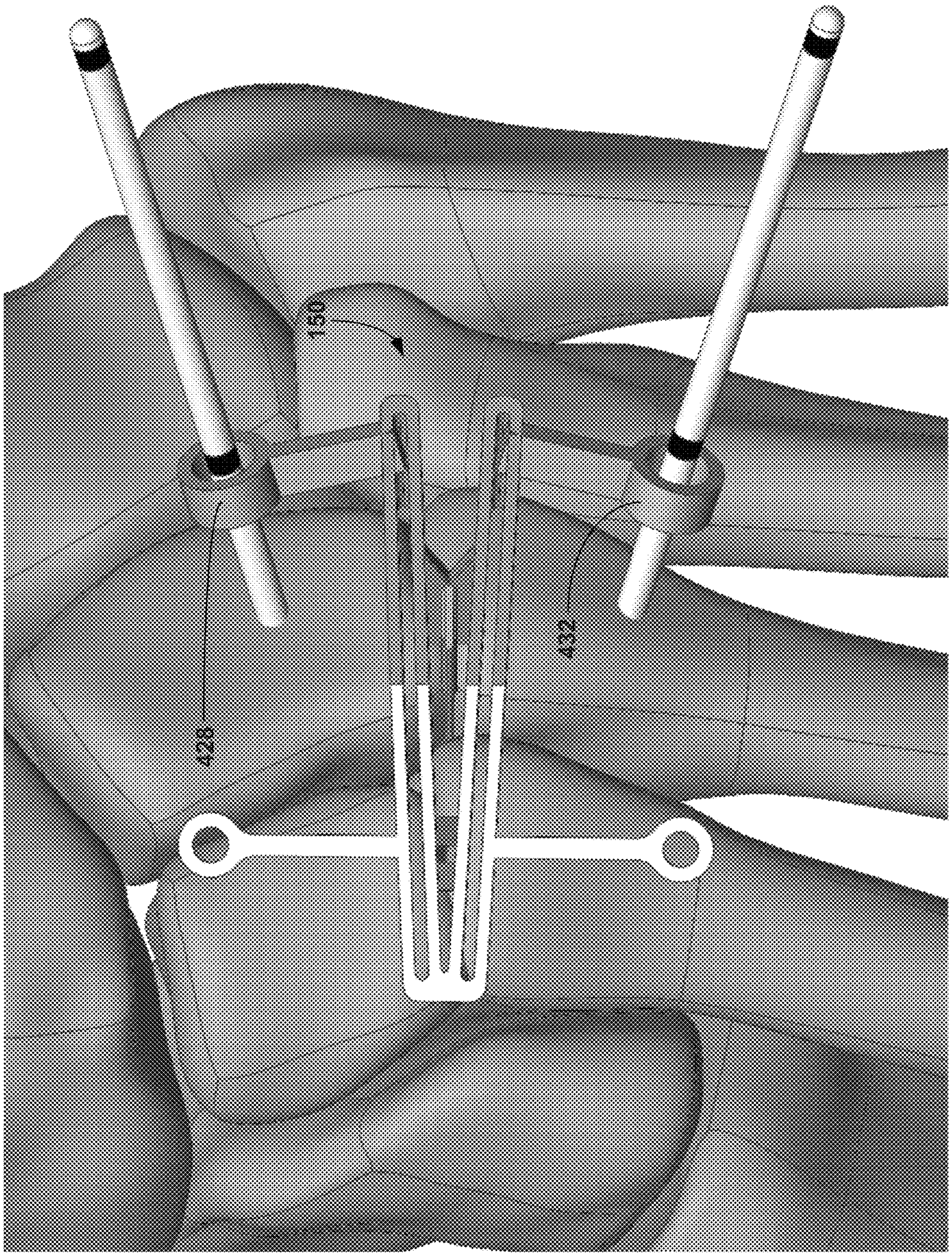

While pin guide 400 is illustrated as being a standalone device, any of the features and functionalities of pin guide 400 may be incorporated into a guide cut, such as any of the configurations of cut guide 150 described herein. For example, FIGS. 6G and 6H illustrate an example configuration of cut guide 150 configured with first pin-receiving hole 402 and second pin-receiving hole 404 positioned and/or configured as described as being provided by pin guide 400. In use, cut guide 150 can be pinned to underlying bones using first pin-receiving hole 402 and second pin-receiving hole 404 (and any other optional pin receiving holes/apertures) and used to prepare one or more bones. Cut guide 150 can then be removed from the underlying bones leaving first pin 420 and second pin 422 inserted into the bones. Compressor-distractor 160 can then be brought down over the pins as discussed herein.

With additional reference to FIG. 4, the example technique is illustrated as including a step of provisionally fixating the moved position of the second metatarsal and the third metatarsal (112). For example, after moving the second metatarsal and third metatarsal into a desired realigned position in one or more planes, such as the transverse plane (which may also involve moving the fourth metatarsal and fifth metatarsal), the clinician may optionally provisionally fixate the moved position. Provisional fixation can hold the moved position of one or more bones to facilitate subsequent surgical steps, such as application of one or more permanent fixation devices and/or the performance of additional surgical steps (e.g., first metatarsal realignment).

To provisionally fixate the moved position of the one or more bones, the clinician may insert one or more pins into and/or through a moved bone and into an adjacent bone. For example, the clinician may insert a pin through the second metatarsal and into an adjacent bone (e.g., a cuneiform) and/or insert a pin through the third metatarsal and into an adjacent bone. The pin may be in the form of a rod and/or a wire (K-wire), and may or may not be configured to apply compression across a joint between the bones in which the pin is inserted, e.g., by having an enlarged region of the pin that presses against the outer surface of the bone through which the tip of the pin is inserted, thereby applying compression.

Independent of whether the clinician deploys a provisional fixation device, the clinician may apply one or more permanent fixation devices to facilitate fusion of the second and third TMT joints following reduction of the metatarsus adduction angle (step 114 in FIG. 4). The one or more fixation devices can extend across the second and/or third TMT joints to secure and hold opposed bone ends together for fusion (and/or other TMT joint in instances in which a different TMT joint is prepared for fusion). For example, the clinician may apply a first fixation device across the second TMT joint and apply a second fixation device across the third TMT joint.

A bone fixation device may be any feature or combination of features that holds two bone portions in fixed relationship to each other to facilitate fusion of the bone portions during subsequent healing. Any one or more bone fixation devices that can be used include, but are not limited to, a bone screw (e.g., a compressing bone screw), a bone plate, a bone staple, an external fixator, an intramedullary implant, and/or combinations thereof. Depending on the type of bone fixation device selected, the bone fixation device may be attached to external surfaces of the bone portions being fixated or may be installed as an intramedullary device internal to the bone portions.

As briefly discussed above, a metatarsus adduction deformity may present with a hallux valgus misalignment in some patients. Accordingly, a clinician performing a metatarsus adduction correction procedure may also perform a hallux valgus correction on the patient undergoing treatment. In the example FIG. 4, the example technique is illustrated as including a first metatarsal realignment step (116). Although the technique of FIG. 4 illustrates the first metatarsal realignment being performed after reduction and permanent fixation of the second and third TMT joints, a different surgical order may be performed. For example, the first metatarsal may be realigned prior to moving a lesser metatarsal (e.g., the second and third metatarsals), or may be realigned after moving the lesser metatarsal (e.g., the second and third metatarsals) but prior to permanently fixating the lesser TMT joint(s).

While the order of the surgical procedure may vary, in some applications, it is useful to reposition one or more lesser metatarsals (e.g., second and/or third metatarsals) prior to correcting the alignment of the first metatarsal. By initially repositioning the lesser metatarsal, such as the second and third metatarsals (and, in some examples, also correcting the position of the fourth and fifth metatarsals), the clinician may be able to better anatomically realign the first metatarsal relative to the aligned lesser metatarsals. Correction of the alignment of one or more of the lesser metatarsals may change the extent of misalignment of the first metatarsal, which can then be further corrected during a subsequent first metatarsal realignment step.

To correct the alignment of first metatarsal 12, the clinician may surgically access the first TMT joint. Once accessed the clinician may prepare an end of first metatarsal 12 and an opposed end of medial cuneiform 26. The clinician may prepare the ends of the bones with or without cutting, as discussed above with respect to preparation of the ends of second metatarsal 14 and third metatarsal 16 (e.g., using any preparation technique discussed herein). In instances in which the clinician prepares one or more bone ends using a cutting instrument, the clinician may or may not utilize a cut guide to guide controlled cutting of the bone ends and/or a bone preparation template to indicate where bone preparation should be performed.

Either before or after preparing one or both ends of first metatarsal 12 and medial cuneiform 26, the clinician may move first metatarsal 12 in at least one plane (e.g., the transverse plane, the frontal plane) to close an intermetatarsal angle between the first metatarsal and second metatarsal 14. In some examples, the clinician moves the first metatarsal in multiple planes, such as the transverse plane and/or frontal plane and/or sagittal plane. The clinician may or may not utilize a bone positioning guide to facilitate movement of the first metatarsal relative to the second metatarsal and/or medial cuneiform. With the first metatarsal moved to a desired position, the clinician can optionally provisionally fixate the moved position of the first metatarsal and then permanently fixate the moved position using one or more bone fixation devices, such as those described above. Additional details on example first metatarsal realignment instruments and techniques that can be used are described in U.S. Pat. No. 9,622,805, issued Apr. 18, 2017 and entitled "BONE POSITIONING AND PREPARING GUIDE SYSTEMS AND METHODS."

While the technique of FIG. 4 has generally been described with reference to preparation of second TMT joint 36 and third TMT joint 38 and movement of both second metatarsal 14 and third metatarsal 16 (optionally in combination with movement of fourth metatarsal 18 and fifth metatarsal 20), the techniques and/or devices may be performed on single TMT joints and/or different TMT joints without departing from the scope of the disclosure. For example, the technique of FIG. 4 may be performed on a single lesser TMT joint, such as only the second TMT joint 36, only the third TMT joint 38, only the fourth TMT joint 40, or only the fifth TMT joint 42, in each case optionally in combination with preparation of the first TMT joint 34 and realignment of the first metatarsal. Other combinations of joint preparation are also possible.

Further, while example techniques are described herein generally in connection with realigning one or more bone in, for example, a lateral direction in a transverse plane, in some applications, the clinician may reposition perform a procedure according to the disclosure without realigning in such plane(s). For example, in the case of an arthritic joint, the clinician may prepare the end faces of the metatarsal and opposed cuneiform for fusion, e.g., by making parallel cuts across the faces of the ends of the bones. The clinician can then compress the prepared end faces of the bones together and apply fixation to promote fusion across the joint without otherwise repositioning one bone relative to another bone.

In some applications where the clinician prepares only a single lesser TMT joint for fusion (again, optionally as part of a procedure that also prepares the first TMT joint), the clinician may move the lesser metatarsal associated with that TMT joint in one or more planes, e.g., using devices and/or techniques discussed herein. Repositioning of the metatarsal associated with the lesser TMT joint being prepared may or may not also move one or more adjacent metatarsals to the lesser metatarsal being moved through ligamentous tissue. For example, if the clinician prepares second TMT joint 36 and moves second metatarsal 14, the repositioning of the second metatarsal may or may not cause realignment of third metatarsal 16, fourth metatarsal 18, and/or fifth metatarsal 20.

As discussed above, a bone realignment technique according to the disclosure may involve cutting an end of a cuneiform and/or an end of an opposed metatarsal. In such applications, the clinician may perform the cuts freehand or with the aid of one or more cut guides (also referred to herein interchangeably as a cutting guide). The use of a cut guide may facilitate more accurate and repeatable cuts patient-to-patient, promoting more consistent clinical outcomes across a range of patients an anatomical deformities. When a cut guide is used, the cut guide may generally define at least one guide surface positionable over a side of the bone to be cut, such as a dorsal side. The clinician can place a cutting instrument adjacent to, and optionally in contact with, the guide surface and translate the cutting instrument relative to the guide surface to perform a cut in a plane parallel to the guide surface. For example, the clinician may place the cutting instrument in contact with the guide surface and then translate the cutting instrument relative to the guide surface, e.g., plantarly into a bone and/or in a medial or lateral direction. The guide surface may bound movement of the cutting instrument to a desired direction of cutting.

Figure 8:
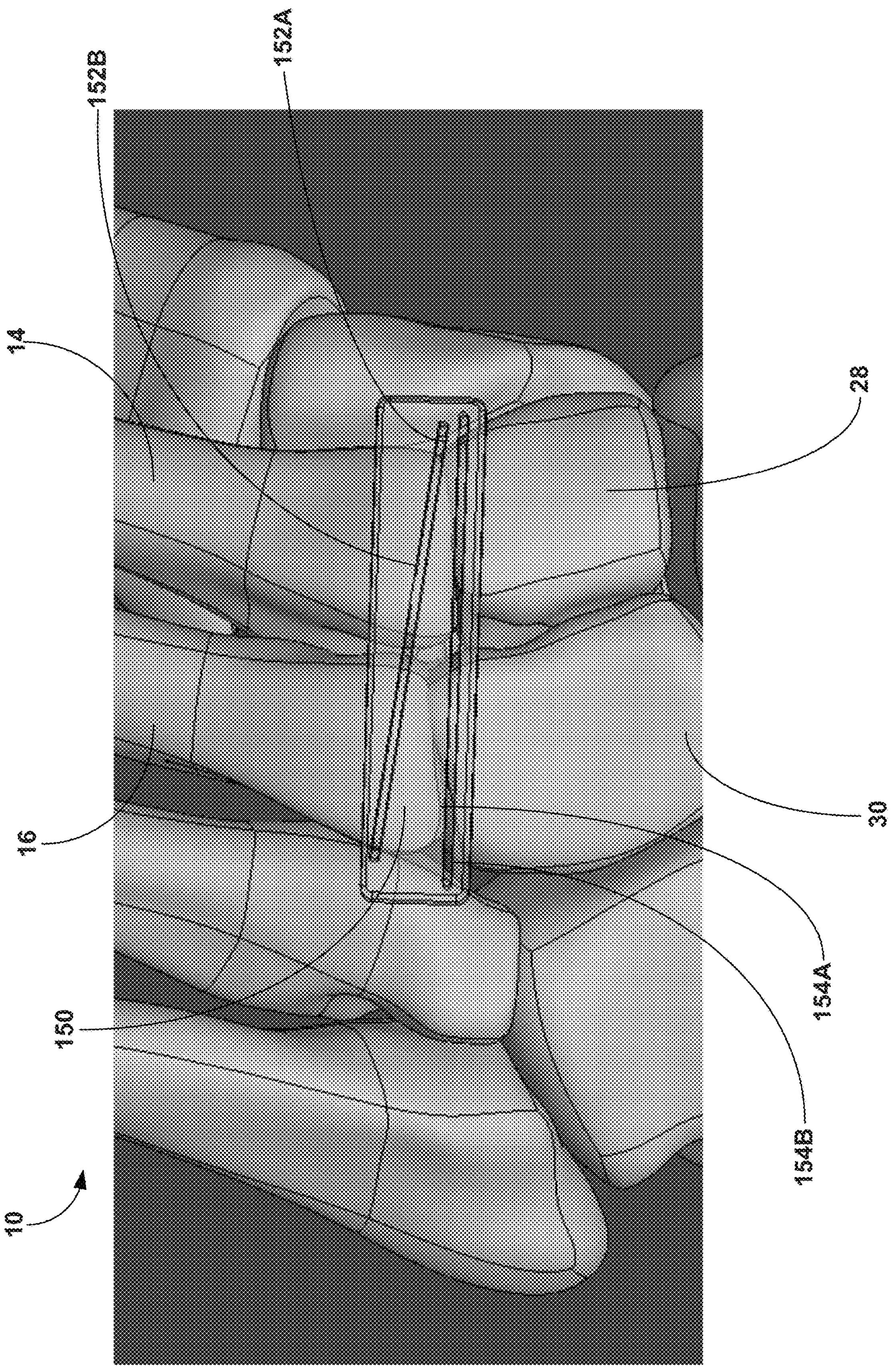
FIG. 8 is a top view of a foot showing the example cut guide introduced with respect to FIG. 5A.

FIG. 8 is a top view of foot 10 showing the example cut guide 150 introduced with respect to FIG. 5A above. Cut guide 150 includes at least one guide surface positionable over a dorsal side of a bone to be cut. For example, cut guide 150 includes a guide surface 152A positionable over a dorsal side of second metatarsal 14 and third metatarsal 16. Guide surface 152A can extend straight (e.g., parallel) or an angle in a dorsal to plantar direction (in other words, in the sagittal plane) and can guide the cutting tool in a direction defined by the guide surface. In use, the clinician can place a cutting tool in abutting relationship with guide surface 152A and advance the cutting tool relative to the guide surface to remove an end of the metatarsal being cut (e.g., second metatarsal 14 and/or third metatarsal 16).

In some examples, cut guide 150 defines a single guide surface. In other examples, cut guide 150 may include multiple guide surfaces, for example spaced apart from each other to define a cutting slot between the guide surfaces. In the illustrated example, cut guide 150 is shown having first metatarsal-side guide surface 152A and a second metatarsal-side guide surface 152B parallel to the first guide surface to define a cutting slot between the two guide surfaces. A clinician can insert a cutting tool, such as a saw blade, in the cutting slot to guide removal of a portion of the end of second metatarsal 14 and a portion of the end of third metatarsal 16.

As discussed above with respect to FIG. 4, a clinician may independently prepare one or more lesser metatarsals (e.g., second metatarsal 14 and third metatarsal 16) and/or may prepare the ends of one or more lesser metatarsals together, e.g., by making a continuous cut transecting two metatarsals. In applications where the clinician desires to make a continuous cut transecting the two metatarsals, cut guide 150 may be configured with a guide surface 152A (or pair of guide surfaces 152A, 152B as illustrated) extending across multiple metatarsals, such as both second metatarsal 14 and third metatarsal 16. For example, the guide surface may define a continuous guide surface extending from a medial-most side of the second metatarsal 14 to a lateral-most side of third metatarsal 16. This can allow the clinician to utilize the guide surface to cut through an entirety of the second and third metatarsals in the medial to lateral direction. When so configured, the guide surface (e.g., cutting slot) may be sized to terminate at the medial-most side of the second metatarsal 14 and/or the lateral-most side of third metatarsal 16 or may extend past such boundary locations. Oversizing the guide surface may allow cut guide 150 to be used on broader patient population set. However, oversizing the guide surface may require closer clinician attention when making one or more cuts utilizing the guide surface.

In FIG. 8, cut guide 150 is illustrated as also having a guide surface 154A positionable over a dorsal side of intermediate cuneiform 28 and lateral cuneiform 30. Guide surface 154A can extend straight (e.g., parallel) or an angle in a dorsal to plantar direction (in the sagittal plane) and can guide the cutting tool in a plane parallel to the guide surface. In use, the clinician can place a cutting tool in abutting relationship with guide surface 154A and advance the cutting tool relative to the guide surface to remove an end of an opposed cuneiform/cuboid bone, such as intermediate cuneiform 28 and lateral cuneiform 30.

As with the metatarsal-side guide surface 152A, the cuneiform-side guide surface 154A may define a single guide surface or may include multiple guide surfaces, for example spaced apart from each other to define a cutting slot between the guide surfaces. In the illustrated example, cut guide 150 is shown having first cuneiform-side guide surface 154A and a second cuneiform-side guide surface 154B parallel to the first guide surface to define a cutting slot between the two guide surfaces. A clinician can insert a cutting tool, such as a saw blade, in the cutting slot to guide removal of a portion of the end of intermediate cuneiform 28 and lateral cuneiform 30.

In some examples, the cuneiform-side guide surface 154A (or pair of guide surfaces 154A, 154B as illustrated) extends across both intermediate cuneiform 28 and lateral cuneiform 30. For example, the guide surface may define a continuous guide surface extending from a medial-most side of intermediate cuneiform 28 to a lateral-most side of lateral cuneiform 30. This can allow the clinician to utilize the guide surface to perform a continuous cut to cut an end portion of both the intermediate cuneiform and the lateral cuneiform. When so configured, the guide surface (e.g., cutting slot) may be sized to terminate at the medial-most side of intermediate cuneiform 28 and the lateral-most side of lateral cuneiform 30 or may extend past such boundary locations to be oversized.

In other examples, the cut guide is not configured with a continuous guide surface extending across intermediate cuneiform 28 and lateral cuneiform 30 but instead has a discontinuous guide surface, or two guide surfaces, separately positionable over each of the cuneiform and/or cuboid bones. When so configured, cut guide 150 may have a guide surface region positionable over each of multiple bones, such as intermediate cuneiforms 28 and lateral cuneiform 30, but a discontinuity or break between the guide surface regions that prevents a continuous cut from being made that transects both cuneiforms. One guide surface may extend from a medial to a lateral side of intermediate cuneiform 28, while another guide surface may extend from a medial to a lateral side of lateral cuneiform 30. A parallel and offset guide surface 154B may be provided to define a cutting slot, e.g., a cut slot over the intermediate cuneiform and/or lateral cuneiform.

While cut guide 150 is illustrated as having both a metatarsal-side guide surface 152A and a cuneiform-side guide surface 154A, in alternative implementations, the cut guide may be configured with a guide surface for only cutting one or more metatarsals and/or one or more cuneiform/cuboid bones. One or more separate cut guides may be utilized to cut the other of the metatarsal(s) or cuneiform(s). Alternatively, the clinician may perform cutting freehand or may perform a bone preparation step that does not involve cutting the bone(s).

Figure 9A:
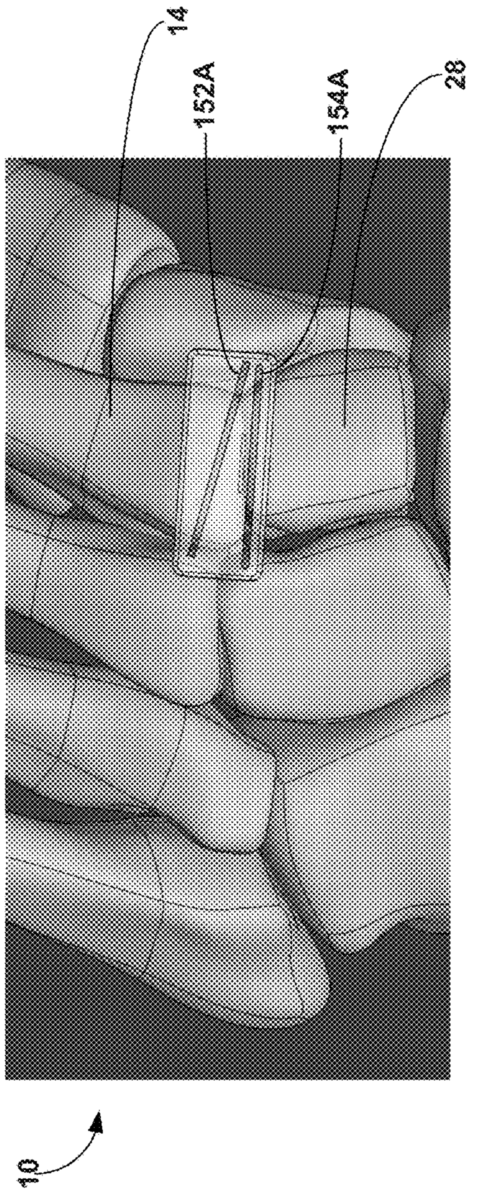
FIGS. 9A and 9B are top views of a foot showing another example configuration of a cut guide.
Figure 9B:
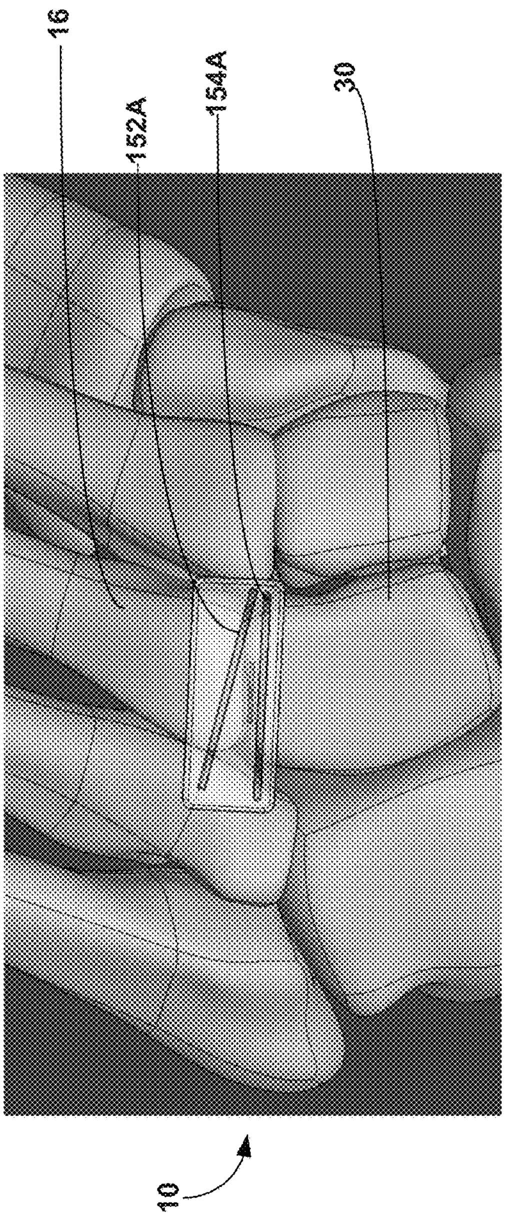

As still another example, cut guide may be configured to be positioned across a single TMT joint to cut a single metatarsal and/or cuneiform instead of being configured to be positioned across multiple metatarsals and/or cuneiforms. FIGS. 9A and 9B are top views of foot 10 showing an alternative configuration of cut guide 150 where the cut guide is configured (e.g., sized and/or shaped) to be positioned across the second TMT joint and the third TMT joint, respectively. A cut guide configured to be positioned across another lesser TMT joint (the fourth TMT joint, fifth TMT joint) can also be provided.

As shown in FIG. 9A, cut guide 150 has a metatarsal-side guide surface 152A (which is illustrated as a cutting slot) extending from a medial-most side of second metatarsal 14 to a lateral-most side of the metatarsal. The cut guide also has a cuneiform-side guide surface 154A (which is also illustrated as a cutting slot) extending from a medial-most side of intermediate cuneiform 28 to a lateral-most side of the cuneiform.

With reference to FIG. 9B, cut guide 150 is illustrated with a metatarsal-side guide surface 152A (which is illustrated as a cutting slot) extending from a medial-most side of third metatarsal 16 to a lateral-most side of the metatarsal. The cut guide also has a cuneiform-side guide surface 154A (which is also illustrated as a cutting slot) extending from a medial-most side of lateral cuneiform 30 to a lateral-most side of the cuneiform.

Cut guide 150 in FIGS. 9A and 9B may be the same cut guide that is moved between the second TMT joint to the third TMT joint. Alternatively, the clinician may have two identical cut guides 150 that are utilized on the different TMT joints. In still further applications, two different cut guides 150 may be provided that are configured differently for the second TMT joint in the third TMT joint, respectively. The cut guides may be configured differently by having different sizes and/or shapes, such as different angular orientations of guide surfaces.

In configurations where cut guide 150 has both a metatarsal-side guide surface and an opposed bone-side guide surface (e.g., cuneiform-side guide surface), the guide surfaces may be parallel to each other, angled relative to each other (e.g., to define a wedge-shaped region), or otherwise oriented relative to each other to achieve desired cut patterns. When using an angled guide surface arrangement, the relative angle between the two guide surfaces can define the size and shape of bone wedge removed utilizing cut guide 150. In some examples, the angle between the metatarsal-side guide surface and the cuneiform-side guide surface is fixed. In other words, the angle between the metatarsal-side guide surface and the cuneiform-side guide surface is set during the design and manufacturing of the cut guide and cannot be varied by the clinician. In these examples, the clinician may be provided with a system having a plurality of cut guides 150 (e.g., two, three, four, five, or more), where each cut guide defines different angles between guide surfaces. The clinician can select a cut guide with desired angle from the system of different guides based on the needs of the particular patient undergoing a procedure. In other examples, however, the angle between the metatarsal-side guide surface and the cuneiform-side guide surface may be adjustable. This can provide the clinician with flexibility to adjust the angular orientation between the metatarsal-side guide surface and the cuneiform-side guide surface for patient-specific anatomical considerations.

Figure 10A:
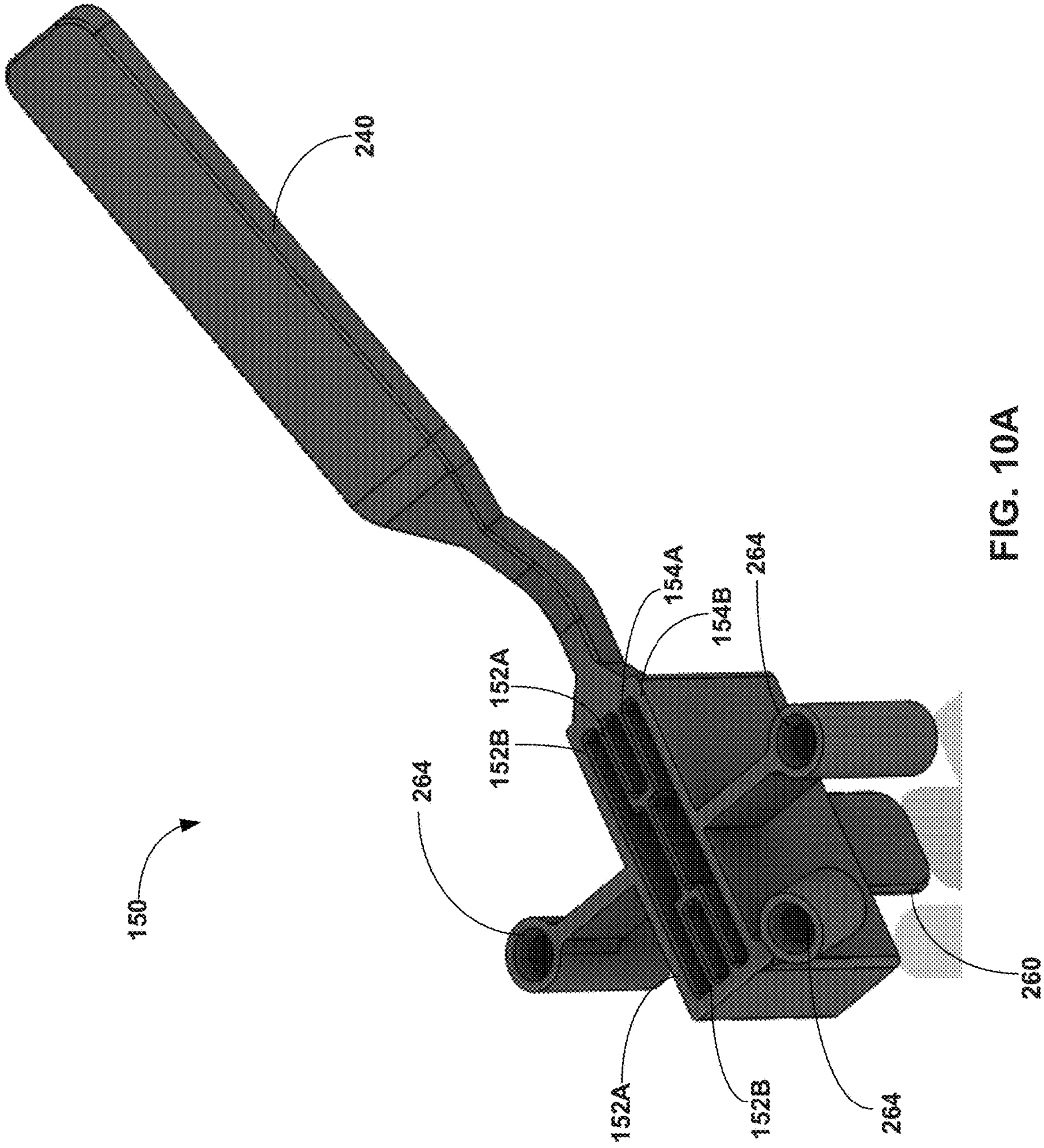
FIGS. 10A-10C are illustrations of an example configuration of a cut guide having guide surfaces that are parallel to each other.
Figure 10B:
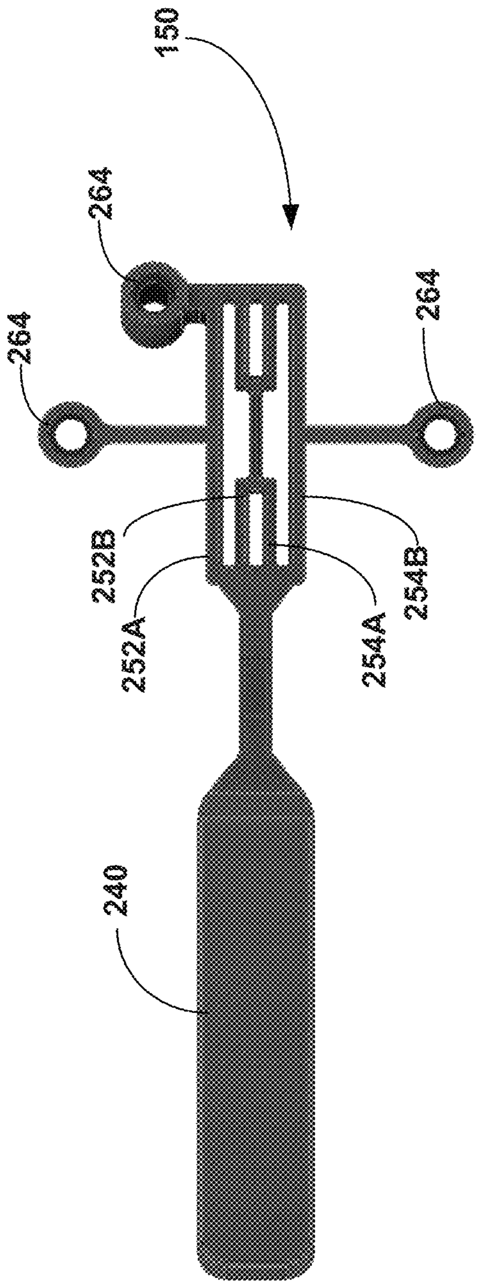
Figure 10C:
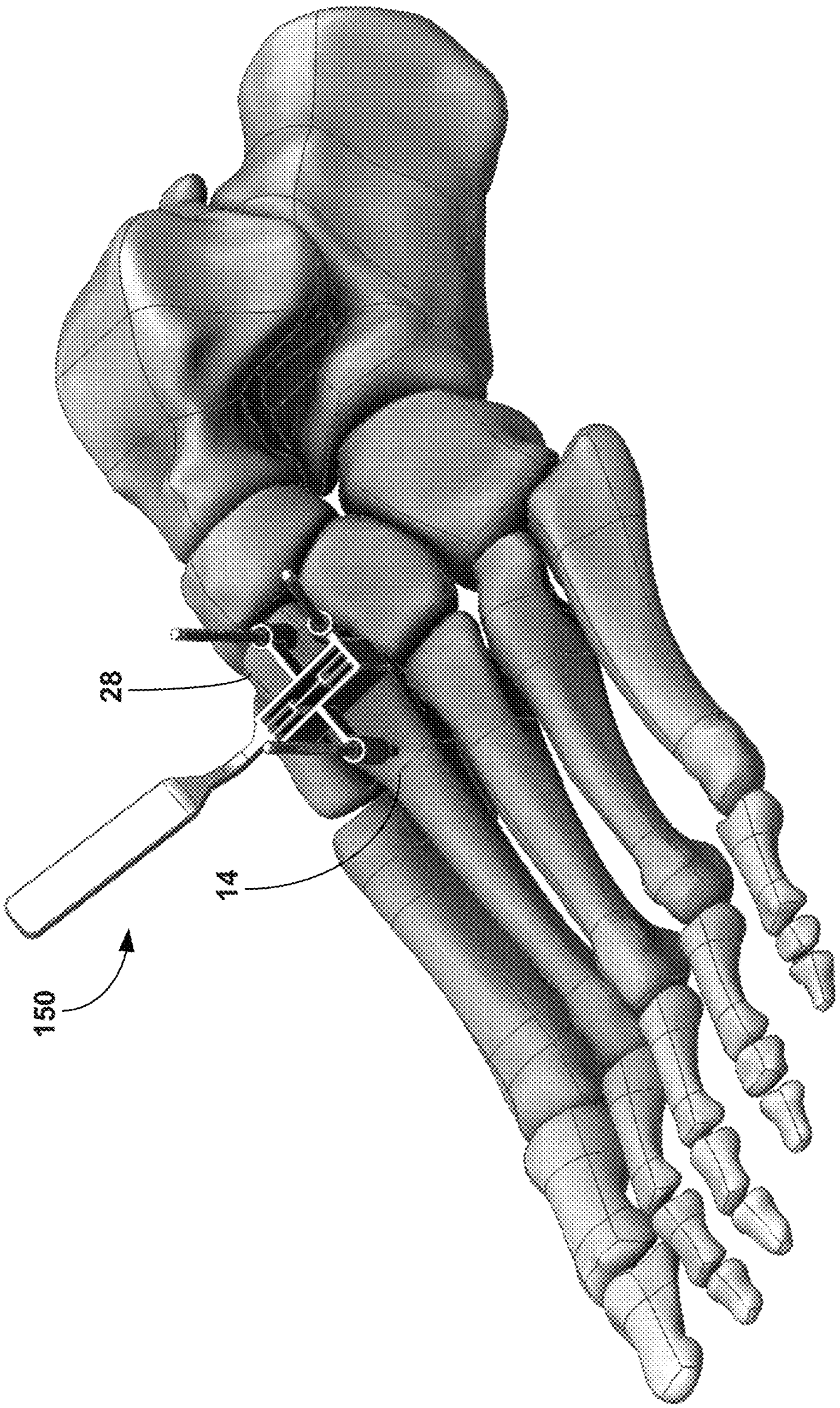

FIGS. 10A-10C are illustrations of an example configuration of cut guide 150 in which the cut guide is configured with both a metatarsal-side guide surface and an opposed bone-side guide surface (e.g., cuneiform-side guide surface), and the guide surfaces are parallel to each other. Cut guide 150 in this example is illustrated as being configured to be positioned across a single TMT joint to cut a single metatarsal and/or cuneiform. In other configurations of the illustrated configuration of cut guide 150, the cut guide can be configured to be positioned over multiple bones in a medial-to-lateral direction, as discussed above with respect to FIG. 8.

FIG. 10A is a perspective view and FIG. 10B is a top view, respectively, of an example configuration of cut guide 150 that includes parallel guide surfaces. As shown in these figures, cut guide 150 includes at least one guide surface positionable over a bone to be cut. For example, cut guide 150 may include a guide surface 152A positionable over a dorsal side of at least one metatarsal to be cut which, as illustrated in FIG. 10C, may be a lesser metatarsal such as second metatarsal 14. Cut guide 150 may also have a facing guide surface to provide a first metatarsal-side guide surface 152A and a second metatarsal-side guide surface 152B parallel to the first guide surface to define a cutting slot between the two guide surfaces.

Cut guide 150 can include a single guide surface (or single cutting slot) or may include multiple guide surfaces separated a distance from each other to be positioned on opposite sides of a joint (e.g., a TMT joint). For example, in FIGS. 10A and 10B, cut guide 150 is shown also having a guide surface 154A positionable over separate bone to be cut. Cut guide 150 may include a guide surface 152A positionable over a dorsal side of at least one cuneiform to be cut which, as illustrated, may be a lesser cuneiform such as intermediate cuneiform 28. Cut guide 150 may also have a facing guide surface to provide a first cuneiform-side guide surface 154A and a second cuneiform-side guide surface 154B parallel to the first guide surface to define a cutting slot between the two guide surfaces.

In the illustrated configuration of FIGS. 10A-10C, the guide surfaces are shown as extending parallel to each other in the transverse plane. In other words, there is a 0° angle between the metatarsal-side guide surfaces in the cuneiform-side guide surfaces. This configuration of cut guide 150 can form parallel cuts on opposed bone ends. This configuration may be useful, for example, for preparing an arthritic joint for fusion. Parallel cuts may be made on the ends of the opposed bones in the prepared bone faces compressed together (e.g., using compressor-distractor 160) for fixation and fusion.

In the illustrated configuration, cut guide 150 includes a handle 240 extending away from the body of the cut guide defining the one or more guide surfaces. Handle 240 is illustrated as extending upwardly and outwardly away from the body defining the guide surfaces although may extend in other directions. Any configuration of a cut guide herein may include a handle 240. Configuring cut guide 150 with handle 240 may be useful to help the clinician position the cut guide at a target location. In different applications, the clinician may hold cut guide over the target bone or bones to be cut using handle 240 while performing cutting and/or may insert one or more fixation pins through fixation holes 264 of the cut guide to hold the cut guide during cutting.

Additional details on example configurations of fixation holes 264 are discussed below. In the illustrated arrangement of FIGS. 10A-10C, cut guide 150 includes at least two parallel fixation holes 264 extending outwardly via arms from the body defining the at least one guide surface of the cut guide. Cut guide 150 is also illustrated at least one fixation hole 264 extending at a skewed angle relative to the parallel fixation holes. In the illustrated arrangement, the fixation hole extending at the skewed angle is attached directly to the body defining at least one guide surface. The fixation hole define the skewed angle may receive a fixation pin that, in use, extends in a dorsal-lateral direction (or a dorsal-medial direction) away from the bone portion being prepared.

Cut guide 150 in FIGS. 10A-10C it is also illustrated as including a spacer 260. Spacer 260 can be inserted into the joint space between the metatarsal and the opposed bone being prepared using cut guide 150. Spacer 260 can help orient the guide surfaces of the cut guide at appropriate positions relative to the joint space. Cut guide 150 can be configured with any type of locating feature (or without such a feature) as discussed herein.

Figure 11:
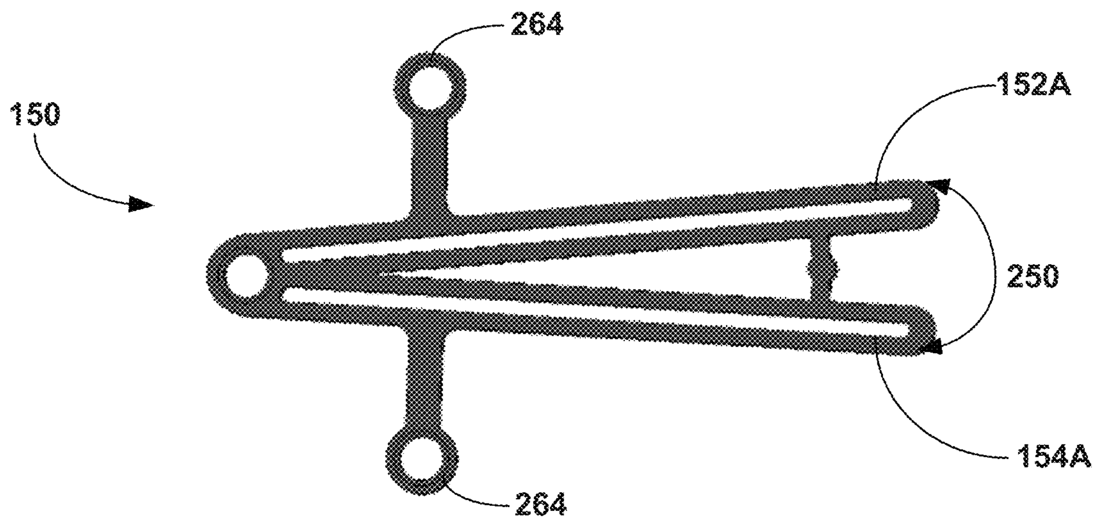
FIG. 11 is a top view of an example configuration of a cut guide in which an angle between a distal-most guide surface and a proximal-most guide surface of the guide is fixed.

FIG. 11 is a top view of an example configuration of cut guide 150 in which an angle 250 between a distal-most guide surface 152A of the cut guide (when positioned over a metatarsal) and a proximal-most guide surface 154A of the guide (when positioned over a cuneiform or cuboid) is fixed. For many clinical applications, angle 250 may be less than 75 degrees, such as less than 60 degrees, less than 45 degrees, less than 35 degrees, less than 20 degrees, less than 15 degrees, less than 10 degrees, or less than 5 degrees. For example, angle 250 may range from 1 degree to 20 degrees, such as from approximately 5 degrees to approximately 20 degrees, from approximately 5 degrees to approximately 10 degrees, or from approximately 6 to approximately 9 degrees. In other examples, angle 250 may be 0 degrees (providing parallel guide surfaces) to allow for reciprocal planing, e.g., on mild cases. Bone wedges cut and/or removed according to a surgical technique according to the disclosure may define angles within any of the forgoing angular limits (or yet different limits), whether or not cut using a cut guide according to the disclosure (e.g., including when cut freehand and/or with the aid of a bone preparation template). Further, any cut guide described herein having two guide surfaces angled relative to each other can implement any of the foregoing angles or angle ranges (or yet different limits).

To help facilitate positioning of cut guide 150 over one or more bones to be cut, the cut guide may include one or more locating features. The locating features may be insertable into a bone and/or a joint space between adjacent bones to provide anatomical reference locations for orienting cut guide 150 relative to the anatomy of the foot of the patient undergoing the clinical procedure. For example, cut guide 150 may include one or more pins and/or spacers that are associated with the cut guide and used to help orient the cut guide relative to the anatomy of the patient.

As used in the present disclosure, a locating pin associated with a cutting guide generally refers to a feature that is inserted into a bone and can be used to help position the cutting guide relative to a bone to be cut. By contrast, a spacer associated with the cutting guide generally refers to a feature that is inserted into a joint space between adjacent bones and can be used to help position the cutting guide relative to a bone to be cut. Each feature described as a locating pin or spacer may have any appropriate size and cross-sectional shape, including arcuate shapes (e.g., circular, oval), polygonal shapes (e.g., square, rectangular, T-shaped), and/or combinations of arcuate and polygonal shapes. The term locating feature encompasses both a locating pin and/or spacer. Each locating feature may have a shaft insertable into a bone and/or joint space.

When cut guide 150 includes one or more associated pins and/or spacers, such features can be integral with (e.g., permanently connected to) the body of the cut guide or can be detachable and separable from the cut guide. Configuring cut guide 150 to be used with at least one locating feature, e.g., spacer and/or pin that can be separately installed in a joint space between bones or in a bone, respectively, can be useful. When so configured, the spacer and/or pin may be installed independently of the cut guide into a bone structure and the cut guide then engaged with the inserted spacer and/or pin. For example, the cut guide may be slide down on the locating feature, attached to a side of the locating feature, or otherwise operatively connected to the locating feature. Once the cut guide is installed on the locating feature, the connection between the cut guide and locating feature may be fixed (e.g., preventing relative movement between the two features) or may be a relatively movable connection (e.g., allowing rotation or other relative movement between the two features). In either case, the spacer and/or pin can be used to identify an anatomical landmark for positioning cut guide 150 and the cut guide then engaged with the spacer and/or pin.

Cut guide 150 according to the disclosure can include any suitable number of locating features, which can be permanently affixed to and/or separable from the body of the cut guide. For example, cut guide 150 may include a single locating feature or multiple locating features (e.g., two, three, or more). When configured with one or multiple locating features, the one or more locating features may be arranged at different locations along the body of the cut guide.

In use, a cut guide (e.g., cut guide 150) having any configuration as described herein can be inserted over one or more bones to be cut, such as an end of a metatarsal to be cut (e.g., second metatarsal 14, third metatarsal 16) and/or an end of an opposed bone (e.g., intermediate cuneiform 28, lateral cuneiform 30). In practice, the clinician can make one or more incisions through the skin of the patient to expose the underlying bones to be cut. The clinician can retract the skin along the incision line to provide a wide an opening into which and/or over which cut guide 150 can be inserted. The clinician may utilize retractors the pull the skin in opposite directions along the incision line to expose the underlying bones and facilitate positioning of cut guide 150 over the bones. In practice, the skin may have a tendency to draw back to its original position along the incision line, potentially causing the skin to overlap the top surface of the bone cutting guide and thereby inhibit bone preparation using the cutting guide. Accordingly, cut guide 150 may include one or more tissue retraction cavities, which may be configured to capture retracted tissue and help retain the retracted tissue offset from the cut guide.

Figure 12A:
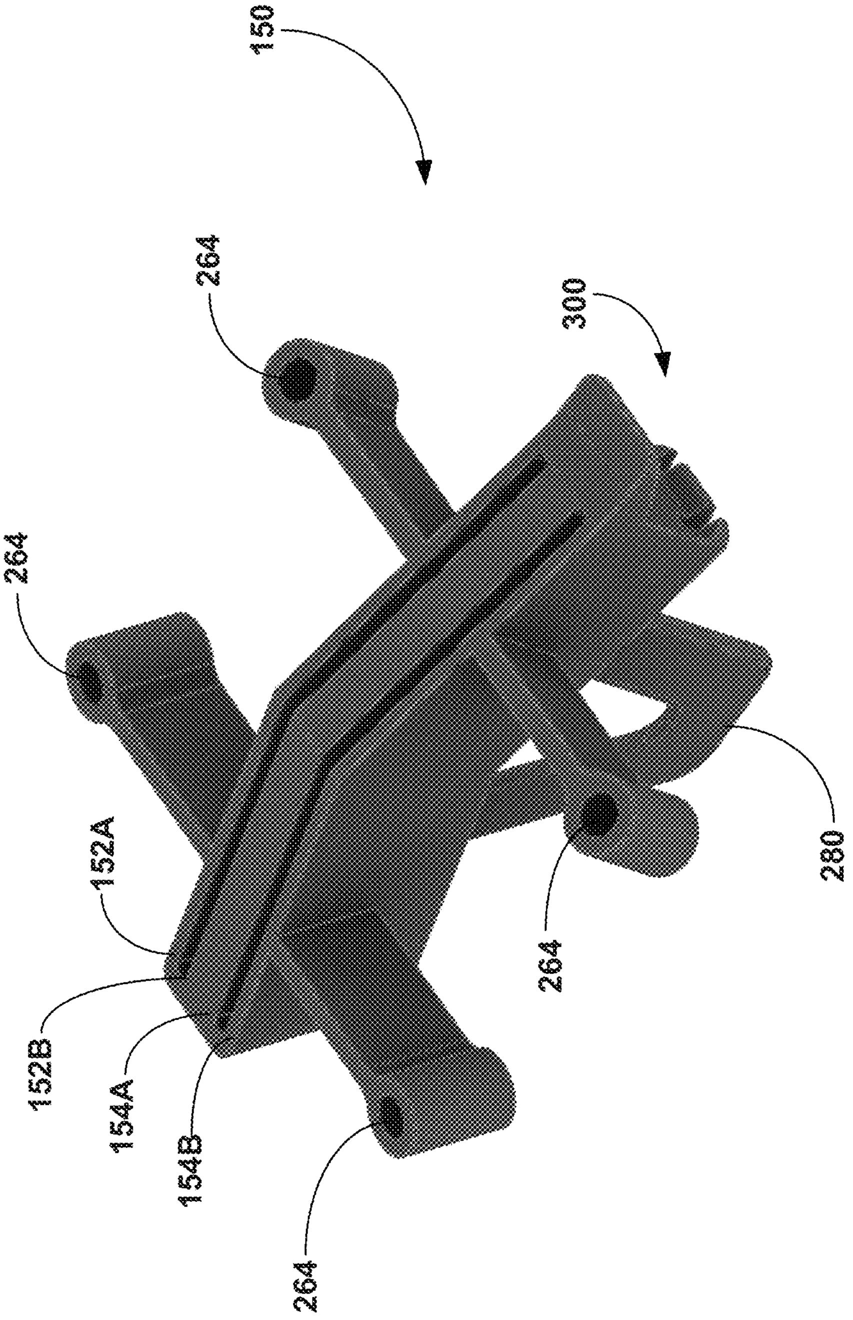
FIGS. 12A and 12B are perspective and side views, respectively, of an example cut guide that includes a tissue retraction cavity.
Figure 12B:
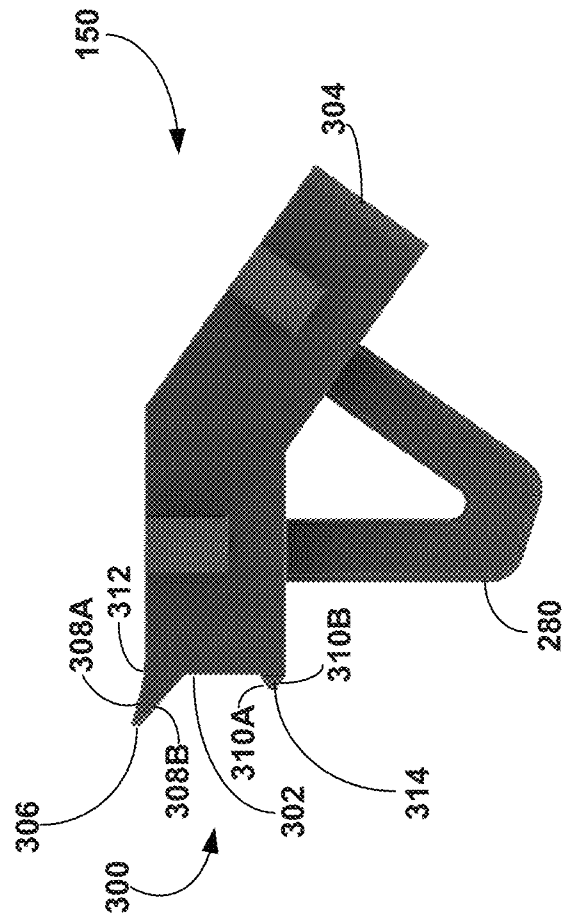

FIGS. 12A and 12B (collectively referred to as "FIG. 12") is a perspective view and a side view, respectively, of an example configuration of cut guide 150 that includes a tissue retraction cavity 300. As shown in FIG. 12, cut guide 150 includes at least one guide surface positionable over a bone to be cut. For example, cut guide 150 may include a guide surface 152A positionable over a dorsal side of at least one metatarsal to be cut which, in the illustrated configuration, is shown as an elongated guide surface configured to be positioned over both second metatarsal 14 and third metatarsal 16. Cut guide 150 may also have a facing guide surface to provide a first metatarsal-side guide surface 152A and a second metatarsal-side guide surface 152B parallel to the first guide surface to define a cutting slot between the two guide surfaces. Cut guide 150 in FIG. 12 can be configured as discussed in greater detail with respect to FIG. 13 below.

Cut guide 150 can include a single guide surface (or single cutting slot) or may include multiple guide surfaces separated a distance from each other to be positioned on opposite sides of a joint (e.g., a TMT joint). For example, in FIG. 12, cut guide 150 is shown also having a guide surface 154A positionable over separate bone to be cut. Cut guide 150 may include a guide surface 1524 positionable over a dorsal side of at least one cuneiform to be cut which, in the illustrated configuration, is shown as an elongated guide surface configured to be positioned over both intermediate cuneiform 28 and lateral cuneiform 30. Cut guide 150 may also have a facing guide surface to provide a first cuneiform-side guide surface 154A and a second cuneiform-side guide surface 154B parallel to the first guide surface to define a cutting slot between the two guide surfaces.

In the illustrated configuration of FIG. 12, the guide surfaces are shown as extending parallel to each other in the transverse plane. In other words, there is a 0° angle between the metatarsal-side guide surfaces in the cuneiform-side guide surfaces. This configuration of cut guide 150 can form parallel cuts on opposed bone ends. In other configurations, metatarsal-side guide surfaces can adopt different angles relative to the cuneiform-side guide surfaces, as discussed herein. Further, any guide surface of cut guide 150 can extend straight (e.g., parallel) or an angle (e.g., non-parallel) in a dorsal to plantar direction (in the sagittal plane).

As mentioned, cut guide 150 includes at least one tissue retraction cavity 300. Cut guide 150 can be configured to extend from a medial side 302 to a lateral side 304 (e.g., when the cut guide is positioned over bones to be cut extending in a medial to lateral direction on the foot). Cut guide 150 can include a tissue retraction cavity 300 on medial side 302 of the cut guide, on lateral side 304 of the cut guide, and/or on both sides of the cut guide. In the illustrated arrangement, cut guide 150 is shown as having a single tissue retraction cavity 300 on the medial side 302 of the cut guide.

Tissue retraction cavity 300 may be defined by a space on a side of cut guide 150 configured to receive and retain tissue (e.g., retracted along an incision line). For example, the body of material defining cut guide 150 may define an outer wall surface on medial side 302 and/or lateral side 304 of the cut guide. Cut guide 150 may include a projection 306 extending outwardly relative to the sidewall. The projection may define a top surface 308A and a bottom surface 308B (e.g., plantar-facing surface). Tissue retraction cavity 300 may be defined as the space bounded by the outer side wall of the cut guide (e.g., outer wall surface of medial side 302 and/or lateral side 304) and bottom surface 308B of the projection.

In some implementations, projection 306 may be positioned comparatively high (e.g., in the dorsal-to-plantar direction) along the overall height of the sidewall of the cut guide, e.g., thereby forming tissue retraction cavity 300 under the projection. For example, projection 306 may be in the uppermost half of the overall height 310 of the cut guide sidewall, such as the uppermost quarter, or the uppermost fifth. In some examples, projection 306 is co-linear with or extends angularly above the top edge 312 of the sidewall bounding tissue retraction cavity 300. In the illustrated configuration, for instance, projection 306 projects upwardly (e.g., dorsally) and outwardly away from the sidewall such that the owner most edge of the projection extends above the top edge 312 of the portion of the sidewall bounding tissue retraction cavity 300. For example, projection 306 may extend an acute angle relative to the sidewall, at a 90° angle relative to the sidewall, or, as illustrated, at an obtuse angle relative to the sidewall. For example, the intersection angle between projection 306 and the sidewall may range from 75° to 155°, such as from 90° to 145°, or from 100° to 135°.

Cut guide 150 may include a single projection 306 bounding tissue retraction cavity 300 or may be configured with multiple projections spaced from each other in defining the tissue retraction cavity between the spaced projections. For example, cut guide 150 may include a second projection 314 that is spaced from the first projection 306. Second projection 314 may be spaced from the first projection, e.g., when cut guide 150 is positioned on a dorsal side of the foot. Second projection 314 can define a top surface 316A (e.g., dorsal-facing surface) and a bottom surface 316. Tissue retraction cavity 300 may be defined as the space bounded by the outer side wall of the cut guide (e.g., outer wall surface of medial side 302 and/or lateral side 304), the bottom surface 308B of the first projection 306, and the top surface 316A of the second projection 314. It should be appreciated that reference to top and bottom are intended to imply relative positioning and do not require any specific orientation with respect to gravity unless otherwise stated.

Second projection 314 may extend outwardly relative to the sidewall at any of the angles discussed with respect is first projection 306. Second projection 314 may extend out from the sidewall the same distance as first projection 306, a greater distance than the first projection, or a shorter distance than the first projection. For example, as illustrated, second projection 314 extends outwardly from the sidewall a shorter distance than first projection 306. This configuration can be helpful to position second projection 314 under the edge of the retracted skin. In use, second projection 314 can be positioned under the retracted skin along the edge of the cut skin, first projection 306 can be positioned over the retracted skin along the edge of the cut skin, and the retracted skin can be retained in an offset position from the top surface of the cut guide through which a cutting instrument is inserted in tissue retraction space 300.

In some configurations, each feature described as a projection extends outwardly from the outer surface of the adjacent sidewall a distance of at least 1 mm, such as at least 2 mm, at least 3 mm, at least 4 mm, or at least 5 mm. For example, one or both of first projection 306 and second projection 314 may extend out a distance ranging from 0.5 mm to 10 mm, such as from 1 mm to 5 mm, 1 mm to 3 mm, 2 mm to 7 mm, or 2 mm to 5 mm. the distance between bottom surface 308B and top surface 316B may be at least 2 mm, such as at least 5 mm, or at least 10 mm. For example, the distance may range from 2 mm to 50 mm, such as from 5 mm to 25 mm.

Figure 12C:
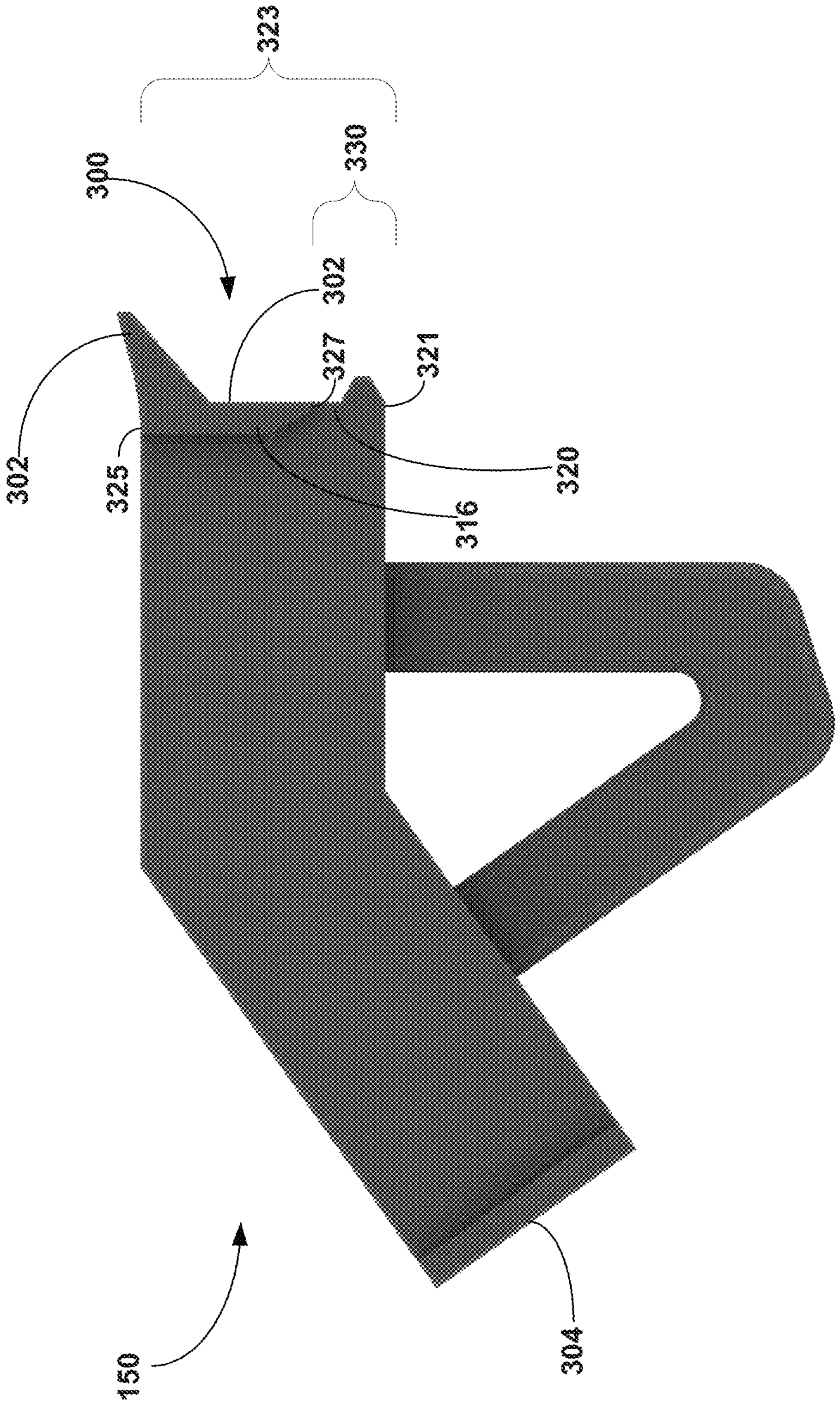
FIG. 12C is a side sectional view of an example cut guide that includes an under cut sidewall.

Any cut guide described herein can have partial or full length wall surfaces. FIG. 12C is a side sectional view of cut guide 150 illustrating an example partial wall cutout configuration. In particular, the sidewall (which can be the medial sidewall and/or lateral sidewall) is illustrated as including a solid region 316 and a cutout 320. For example, cut guide 150 may include a cutout 320 on a lower portion of a sidewall (e.g., medial) bounding a medial extent of a guide surface of the cutting guide. In use, the clinician can advance a cutting instrument along a guide surface, e.g., between a medial sidewall and a lateral sidewall, to cut one or more bones. Upon reaching a sidewall with a lower cutout, the clinician may rotate the cutting instrument through the cutout and under an upper portion of the sidewall bounding the cutout. This can allow the clinician to optionally extend the range of cutting beyond the sidewall(s) of the bone cutting guide. This may be useful, e.g., if the sidewall of the bone cutting guide is positioned slightly offset to an underlying bone and the clinician desires to cut under the sidewall of the bone cutting guide to complete cutting through underlying bone.

For instance, in the example of FIG. 12C, medial side 302 of cut guide 150 is illustrated as having cutout 320. In particular, cut guide 150 is illustrated as having a sidewall 302 having a sidewall cutout 320 extending from bottom end of the side wall downwardly to a bottom-most end 321 (e.g., planar end) of the cut guide. Sidewall cutout 320 can be aligned with a guide surface (e.g., slot) defined by cut guide 150. When configured with multiple guide surfaces, cut guide 150 may include multiple sidewall cutouts (e.g., each configured as described with respect to sidewall cutout 320), with each cutout being aligned with a respective guide surface and/or slot.

The sidewall 302 can define a height 323 measured from a top end 325 of the cut guide to a bottom-most end 321 of the cut guide. Sidewall cutout 320 can also define a height 330 measured from the bottom end 327 of the solid portion 316 of sidewall 302 to the bottom-most end 321 of the cut guide 150. In some implementations, the height 330 of sidewall cutout 320 is less than 50% of the overall height 323 of sidewall 302, such as less than 40%, less than 30%, less than 25%, or less than 20%. For example, the height 330 of sidewall cutout 320 may be within a range from 10% to 50% of the overall height 323 of sidewall 320, such as from 20% to 40%. The height 330 of sidewall cutout 320 may be sufficiently large to allow a bone preparation instrument to advance to a desired location under the sidewall. However, the height 330 of sidewall cutout 320 may be sufficiently small to restrict the angle at which the bone preparation instrument can be advanced under the sidewall (e.g., to help prevent unintended cutting).

In some examples, the terminal end 327 of the solid portion 316 of sidewall 302 is angled where the sidewall bounds sidewall cutout 320. Angulation of the terminal end can help when angularly aligning a bone preparation instrument relative to the sidewall within the sidewall cutout. For example, as shown in FIGS. 12C, solid portion 316 of sidewall 302 can define a lower end or edge 327 bounding sidewall cutout 320, and the lower edge can be angled outwardly.

As noted, cut guide 150 can be configured to extend from a medial side 302 to a lateral side 304 (e.g., when the cut guide is positioned over bones to be cut extending in a medial to lateral direction on the foot). Cut guide 150 can include one or more sidewall cutouts on medial sidewall 302 of the cut guide, on lateral sidewall 304 of the cut guide, and/or on both sides of the cut guide.

With reference to FIGS. 10-12, cut guide 150 may include one or more fixation holes 264 that allow the cut guide to be provisionally fixated to an underlying bone. The one or more fixation holes may be configured to receive a fixation pin. In use, the clinician can install cut guide 150 over one or more bones to be cut and/or adjust an orientation of the one or more guide surfaces of the cut guide until such one or more guide surfaces are appropriately positioned relative to the portions of bone to be cut. Depending on the configuration of cut guide 150, the clinician may further adjust the relative angle 250 between the guide surfaces. In either case, once cut guide 150 is appropriately positioned relative to the bones to be cut, clinician may insert a pin through each of the one or more fixation holes 264 into an underlying bone. The one or more fixation pins installed through fixation holes 264 can secure and hold cut guide 150 at a desired position for the clinician to subsequently utilize the cut guide to guide movement of a cutting instrument.

In some examples, cut guide 150 includes at least two parallel fixation holes 264, such as two holes positioned to be placed on the dorsal side of two different bones separated by a joint (e.g., a metatarsal and opposed cuneiform). In use, a clinician can insert fixation pins through the two holes to attach the cut guide to the metatarsal and cuneiform, respectively. The clinician may remove the cut guide after use while leaving the parallel pins in position (e.g., by sliding the cut guide up off the parallel pins). The clinician may then insert a second instrument having two parallel fixation holes back down over the parallel fixation pins still remaining in the bones. For example, the clinician may insert a bone positioner and/or compressor back down over the parallel fixation pins. The clinician can then apply a force through the pins using the instrument to move the bones. In addition to or in lieu of providing two parallel fixation holes, cut guide 150 may define one or more fixation holes that are angled (at a non-zero degree angle) or otherwise skewed relative to one or more (e.g., two parallel) fixation holes.

In some configurations, the position of one or more (optionally all) of the fixation holes 264 defined by cut guide 150 are fixedly (e.g., non-movably) located relative to the body of the cut guide. In practice, however, the location of patient's bone surface to a fixation hole 264 defined by a cut guide may vary depending on the anatomy of the patient and extent of the patient's bone deformity. For these and other reasons, cut guide 150 can be configured with one or more adjustable fixation holes 264. A fixation hole may be adjustable in that the fixation hole may be movable relative to a length and/or width of the body of cut guide 150 and/or rotatable to adjust the orientation of the fixation hole relative to the orientation of one or more guide surfaces defined by the cut guide.

Figure 13:
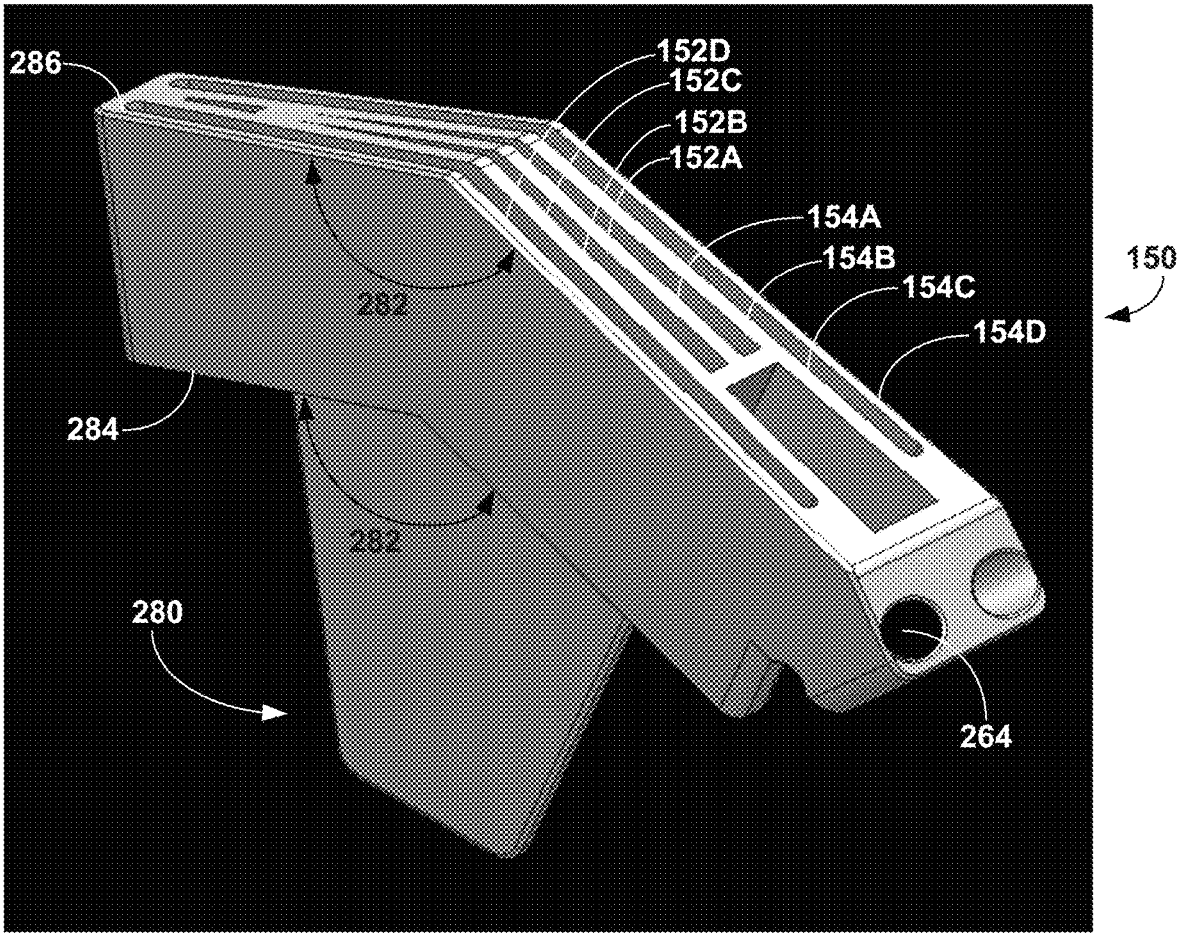
FIG. 13 is perspective view of an example cut guide with associated locating feature.

Cut guide 150 can have a variety of different configurations, as discussed above. For example, cut guide 150 can have one or more associated locating features (e.g., pins and/or spacers), each of which can be permanently affixed to or separable from the body of the cut guide. The pin(s) and/or spacer(s) can function as a locating feature insertable into a bone and/or a joint space between adjacent bones, respectively, to provide anatomical reference locations for orienting cut guide 150 relative to the anatomy of the foot of the patient undergoing the clinical procedure. FIG. 13 is perspective view of another example implementation of cut guide 150 with associated locating feature 280, which is illustrated as a spacer in the form of a keel. Spacer 280 can be permanently affixed to, or detachably couplable to, cut guide 150. Spacer 280 can be configured (e.g., sized and/or shaped) to be positioned in one or more joint spaces, such as bridging across multiple joint spaces of one or more bones to be cut.

As discussed above, cut guide 150 can include one or more guide surfaces configured to extend across multiple bones to be cut, such as across second metatarsal 14 and third metatarsal 16 and/or across intermediate cuneiform 28 and lateral cuneiform 30. Accordingly, spacer 280 may be configured to be positionable at least partially within multiple joint spaces, such as at least partially within the second tarsometatarsal joint space (between second metatarsal 14 and intermediate cuneiform 28) and also at least partially within the third tarsometatarsal joint space (between third metatarsal 16 and lateral cuneiform 30). Spacer 280 can bridge across the intermetatarsal space between second metatarsal 14 and third metatarsal 16. Configuring spacer 280 to be simultaneously positionable in two tarsometatarsal joint spaces can be useful to properly align cut guide 150 relative to bones to be cut on either side of both joint spaces.

Figure 14:
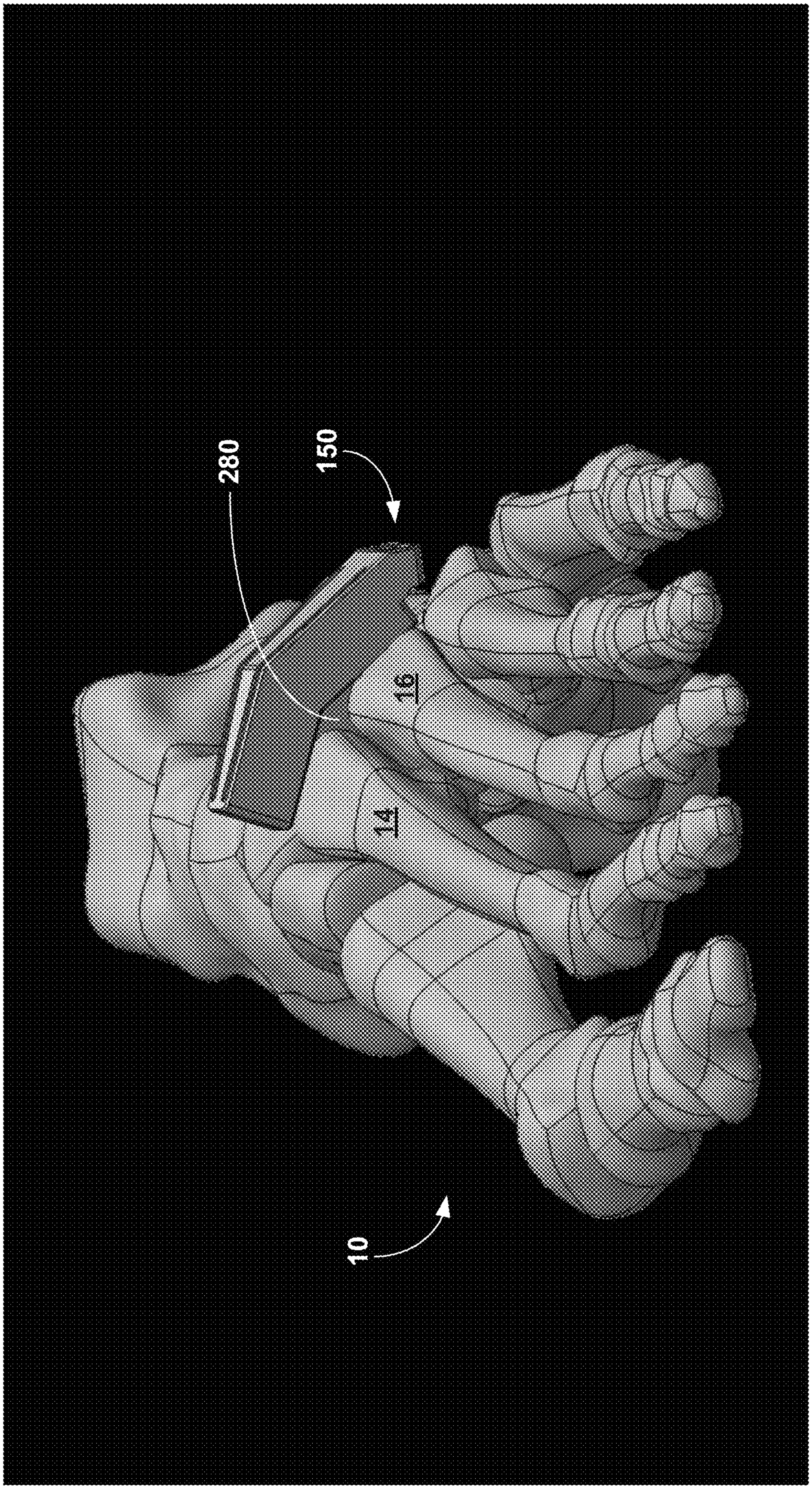
FIG. 14 is a front perspective view of a foot showing the cut guide of FIG. 13 positioned over a dorsal side of one or more bones to be cut.

FIG. 14 is a front perspective view of foot 10 showing cut guide 150 positioned over a dorsal side of one or more bones to be cut with spacer 280 inserted (plantarly) into two tarsometatarsal joint spaces. In particular, in the illustrated example, spacer 280 is positioned at least partially within the second tarsometatarsal joint space and the third tarsometatarsal joint space, with the spacer bridging across the intermetatarsal space between second metatarsal 14 and third metatarsal 16. In some examples, spacer 280 is configured to contact at least a medial quarter of the end face of second metatarsal 14 and the opposed end face of intermediate cuneiform 28, such as at least a medial half, or the full end face of the second metatarsal and the intermediate cuneiform. Additionally or alternatively, spacer 280 can be configured to contact at least a lateral quarter of the end face of third metatarsal 16 and the opposed end face of lateral cuneiform 30, such as at least a lateral half, or the full end face of the third metatarsal and the lateral cuneiform. Spacer 280 can bridge across the intermetatarsal space between the two tarsometatarsal joint spaces.

With further reference to FIG. 13, cut guide 150 includes at least one guide surface positionable over a dorsal side of a bone to be cut. In the illustrated example of FIG. 19, cut guide 150 includes a first metatarsal-side guide surface 152A and a second metatarsal-side guide surface 152B parallel to the first guide surface to define a cutting slot between the two guide surfaces. The cut guide also includes a third metatarsal-side guide surface 152C and a fourth metatarsal-side guide surface 152D parallel to the third guide surface to define a second cutting slot between the two guide surfaces. The second cutting slot is positioned distally of the first cutting slot.

In addition, cut guide 150 in FIG. 13 includes a first cuneiform-side guide surface 154A and a second cuneiform-side guide surface 154B parallel to the first guide surface to define a cutting slot between the two guide surfaces. The cut guide also includes a third cuneiform-side guide surface 154C and a fourth cuneiform-side guide surface 154D parallel to the third guide surface to define a second cutting slot between the two guide surfaces. The second cuneiform-side cutting slot is positioned proximally of the first cuneiform-side cutting slot. Cut guide 150 can have a different number or arrangement of guide surfaces, as discussed above.

Configuring cut guide 150 with multiple guide surfaces (e.g., cutting slots) offset (e.g., proximally or distally) from each other can be useful to provide the clinician with flexibility in selecting the amount of bone to remove. The clinician can select one of multiple parallel guide surfaces (e.g., two, three, four, or more guide surfaces) based on the desired amount of bone to be removed and guide a cutting instrument along the selected guide surface to remove the desired amount of bone. Configuring cut guide 150 with multiple guide surface can also be useful to allow revision cuts. For example, after the clinician removes an initial amount of bone using one guide surface, the clinician may decide that additional bone removal is appropriate to achieve the desired correction. Accordingly, the clinician may reuse the same cut guide, selecting a different guide surface farther along the length of the bone to remove an additional portion of bone. Any configuration of cut guide 150 described herein can include multiple guide surfaces (e.g., cutting slots) spaced from each other (e.g., proximally and/or distally), which may or may not be parallel aligned to each other, to facilitate removing different amounts of bone depending on the specific guide surface selected by the clinician.

With reference to FIG. 13, cut guide 150 may be configured with a continuous guide surface configured to extend across two bones to be cut (e.g., from a medial-most side of the second metatarsal 14 to a lateral-most side of third metatarsal 16) or may have a discontinuous guide surface with separate portions configured to be positioned over separate bones to be cut. In either case, cut guide 150 may define a non-zero degree angle 282 between the portion of one or more guide surfaces configured to be positioned over a medial bone to be cut (e.g., second metatarsal 14, intermediate cuneiform 28) and the portion of one or more guide surfaces configured to be positioned over a lateral bone to be cut (e.g., third metatarsal 16, lateral cuneiform 30). Angling the medial and lateral portions of cut guide 150 relative to each other may be useful to orient the guide surface(s) defined by the guide relative to the anatomical contour of the foot, e.g., as illustrated in FIG. 14. In some examples, cut guide 150 defines an angle 282 between a guide surface to be positioned over a medial bone and a guide surface to be positioned over an adjacent lateral bone ranging from 90 to 179 degrees, such as from 110 to 175 degrees, from 125 to 170 degrees, or from 135 to 165 degrees.

When cut guide 150 is configured with an angled shape between medial and lateral portions of the cut guide, both the plantar side of the cut guide (e.g., bone contacting surface of the cut guide) and the dorsal side of the cut guide (e.g., outward facing side of the cut guide) may be angled. For example, FIG. 13 illustrates both the bone contacting side 284 of cut guide 150 and the outward facing side 286 of the cut guide being angled at substantially the same angle 282. This arrangement may be useful so the bone contacting side 284 of cut guide 150 conforms to the profile of the underlying bones and this profile is observable to the clinician through the mirrored profile on the outward facing side 286 of the cut guide. In other examples, however, one or both sides 284, 286 of the cut guide may be straight (e.g., non-angled) or the bone contacting side 284 may be angled at a different degree of angulation than the outward facing side 286 of the cut guide.

While cut guide 150 may define a sharp transition between the different planes defining the bone facing surfaces and/or outward facing surfaces of the cut guide, in other examples, the cut guide may define a curved bone facing surface and/or outward facing surface to affect the transition between the different planes defined by the bones. For example, the bone facing surface 284 of cut guide 150 may define a curved profile that positions the bone facing surface in contact with the dorsal surfaces of the underlying bones. The outward facing surface 286 may or may not mirror the curved bone facing surface.

In practice, angling and/or curving the outward facing surface 286 of cut guide 150 can be useful so the lateral portion of the cut guide is offset plantarly relative to the medial portion of the cut guide. This may help the clinician visualize the sagittal plane offset between the second and third metatarsals. For example, the clinician may be instructed to move the cutting instrument perpendicular to the outward facing surface of cutting guide 150, resulting in an angular reorientation of the cutting instrument as the instrument moves to the angled lateral portion of the cutting guide. This can help prevent the clinician from inadvertently cutting into the adjacent fourth metatarsal.

Figure 15:
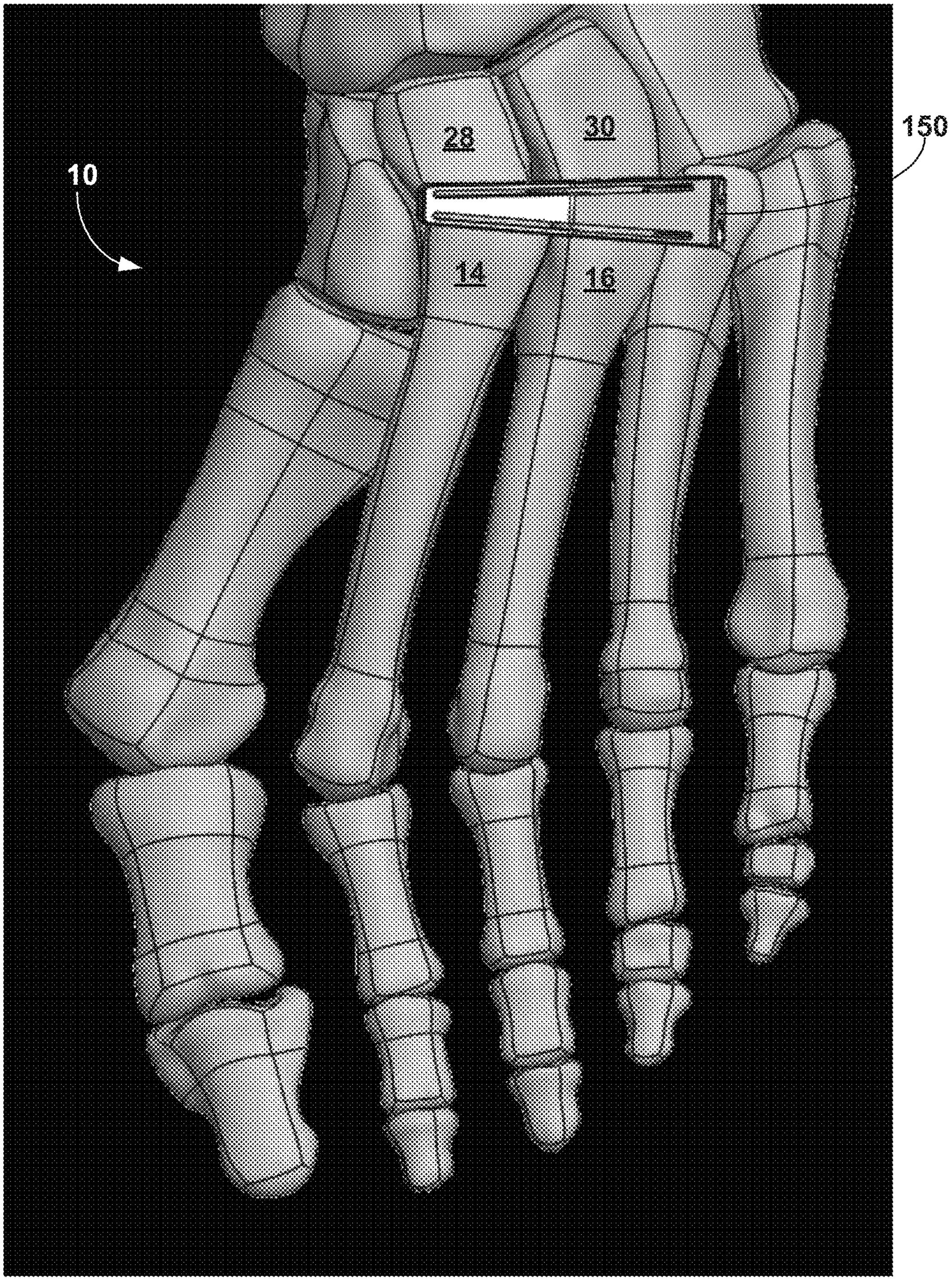
FIG. 15 is a top view of the foot with engaged cut guide of FIG. 14.

In use, spacer 280 can be positioned at least partially within two different and adjacent joint spaces, where each joint space separates two opposed bone ends. This can orient the one or more guide surfaces of cutting guide 150 over the dorsal surfaces of adjacent bone ends to be cut. FIG. 15 is a top view of foot 10 illustrating an example configuration of cutting guide 150 positioned over adjacent bone ends to be cut, with spacer 280 inserted into adjacent joint spaces defined by the bone ends to be cut. Cutting guide 150 in FIG. 15 is illustrated as having a single cuneiform-side cutting slot and a single metatarsal-side cutting slot, although can have different designs as discussed above, such as only have a single slot that can be reversibly positioned over the metatarsal and cuneiform.

In general, spacer 280 may extend from a first end attached to, or attachable to, cut guide 150 to a second end insertable plantarly into adjacent joint spaces. In some examples, such as the example of FIG. 13, spacer 280 may taper in width (e.g., the distance the spacer spans across the adjacent joint spaces) and/or thickness from the first end to the second end. In other examples, spacer 280 may have a constant width and/or thickness over the length of the spacer.

In FIG. 13, spacer 280 is illustrated as a block insertable into adjacent tarsometatarsal joint spaces, with the spacer block spanning between the two tarsometatarsal joint spaces. In some examples, spacer 280 defines a rim of material with a void or open space in the inner portion (e.g., middle) of the spacer, as illustrated in the configuration of FIG. 12. This configuration may be useful to help ease insertion of spacer 280 into the joint space(s) and/or facilitate cleaning and sterilization of the spacer portion of the cut guide after use.

While the foregoing description of cut guide 150 and associated locating feature(s) has generally focused on a configuration for positioning over the second tarsometatarsal joint and the third tarsometatarsal joint, the cut guide can be configured to cut any tarsometatarsal joint or combination of joints. For example, cut guide 150 and associated locating feature(s) (when used) can be configured for positioning one or more guide surfaces over one or more bone ends defining the third tarsometatarsal joint and fourth tarsometatarsal joint, or the fourth tarsometatarsal joint and fifth tarsometatarsal joint, instead of the second and third tarsometatarsal joints. Accordingly, discussion of instruments and techniques for preparing an end of second metatarsal 14 and/or and end of intermediate cuneiform 28 (and/or an end of third metatarsal 16 and/or an end of lateral cuneiform 30) should be understood to apply equally to other lesser tarsometatarsal joint spaces and/or other bone ends.

Reference to a metatarsal-side and cuneiform-side for any device herein (e.g., bone positioner, cut guide) is intended to describe relative positions and orientations of features where the device crosses a TMT joint with a metatarsal on one side and a cuneiform on another side. Where the device is deployed across two different bones, such as the fourth metatarsal and the cuboid bone or yet other two bones or bone portions (e.g., two bone portions separated by a joint), the terminology can be changed based on that anatomy.

Various examples have been described. These and other examples are within the scope of the following claims.

The invention claimed is:

1. A method comprising:

positioning a first pin-receiving hole of a first engagement arm of a compressor-distractor over a first bone portion that is one of an intermediate cuneiform, a lateral cuneiform, and a cuboid, the first engagement arm having a first straight portion defining the first pin-receiving hole and extending dorsally and laterally from the first bone portion and a first angled portion extending plantarly and laterally from the first straight portion;

positioning a second pin-receiving hole of a second engagement arm of the compressor-distractor over at second bone portion that is one of second metatarsal, a third metatarsal, a fourth metatarsal, or a fifth metatarsal, the second engagement arm having a second straight portion defining the second pin-receiving hole and extending dorsally and laterally from the second bone portion and a second angled portion extending plantarly and laterally from the second straight portion;

inserting a first pin through the first pin-receiving hole and into the underlying first bone portion;

inserting a second pin through the second pin-receiving hole and into the underlying second bone portion; and actuating the compressor-distractor to adjust a separation distance between the first bone portion and the second bone portion.

2. The method of claim 1, wherein the compressor-distractor comprises a rail, and actuating the compressor-distractor comprises moving the second engagement arm along the rail relative to the first engagement arm.

3. The method of claim 1, wherein:

the first straight portion and the second straight portion each have a length that is greater than 10 mm; and the first angled portion and the second angled portion each have a length that is greater than 20 mm.

4. The method of claim 1, wherein positioning the first pin-receiving hole of the first engagement arm over the first bone portion and positioning the second pin-receiving hole of the second engagement arm over the second bone portion comprising positioning the first straight portion and the second straight portion at an angle ranging from 50 degrees to 85 degrees with respect to a sagittal plane.

5. The method of claim 1, wherein:

the first angled portion extends at a first acute angle relative to a longitudinal axis defined by the first pin-receiving hole;

the second angled portion extends at a second acute angle relative to a longitudinal axis defined by the second pin-receiving hole; and the first acute angle and the second acute angle each range from 35 degrees to 65 degrees.

6. The method of claim 5, wherein the first acute angle and the second acute angle are each fixed angles.

7. The method of claim 1, wherein inserting the first pin through the first pin-receiving hole and into the underlying first bone portion comprises inserting the first pin after inserting the second pin through the second pin-receiving hole and into the underlying second bone portion.

8. The method of claim 1, wherein the first bone portion is the lateral cuneiform and the second bone portion is the third metatarsal.

9. The method of claim 8, further comprising:

cutting an end of at least one of the second metatarsal and the intermediate cuneiform to create an opening between the end of the second metatarsal and the intermediate cuneiform;

cutting an end of at least one of the third metatarsal and the lateral cuneiform to create an opening between the end of the third metatarsal and the lateral cuneiform;

moving the second metatarsal and the third metatarsal in at least one plane; and fixating a moved position of the second metatarsal and the third metatarsal.

10. The method of claim 9, wherein moving the second metatarsal and the third metatarsal comprises:

inserting the first pin into the first pin-receiving hole and the underlying lateral cuneiform;

manually moving the second metatarsal and the third metatarsal in both a transverse plane and a frontal plane; and subsequently inserting the second pin into the second pin-receiving hole and the underlying third metatarsal.

11. The method of claim 9, wherein actuating the compressor-distractor to adjust a separation distance between the first bone portion and the second bone portion results in moving the second metatarsal and the third metatarsal in at least one plane.

12. The method of claim 9, further comprising:

preparing an end of the other of the second metatarsal and the intermediate cuneiform; and preparing an end of the other of the third metatarsal and the lateral cuneiform.

13. The method of claim 9, wherein:

cutting the end of at least one of the second metatarsal and the intermediate cuneiform to create the opening comprises cutting the end of at least one of the second metatarsal and the intermediate cuneiform to create a wedge-shaped opening; and cutting the end of at least one of the third metatarsal and the lateral cuneiform to create the opening comprises cutting the end of at least one of the third metatarsal and the lateral cuneiform to create a wedge-shaped opening.

14. The method of claim 9, wherein fixating the moved position of the second metatarsal and the third metatarsal comprises:

applying at least one fixation device across a second tarsal-metatarsal joint between the second metatarsal and the intermediate cuneiform, and applying at least one fixation device across a third tarsal-metatarsal joint between the third metatarsal and the lateral cuneiform.

* * * * *